(12) United States Patent
Waldraff et al.

(10) Patent No.: US 7,855,166 B2
(45) Date of Patent: Dec. 21, 2010

(54) SULFONYLAMINO(THIO)CARBONYL COMPOUNDS

(75) Inventors: Christian Waldraff, Bad Vilbel (DE); Hansjörg Dietrich, Hofheim (DE); Heinz Kehne, Hofheim (DE); Martin Hills, Idstein (DE); Thomas Auler, Leichlingen (DE); Klaus-Helmut Müller, Düsseldorf (DE); Dieter Feucht, Eschborn (DE)

(73) Assignee: Bayer Cropscience GmbH, Frankfurt (DE)

( * ) Notice: Subject to any disclaimer, the term of this patent is extended or adjusted under 35 U.S.C. 154(b) by 396 days.

(21) Appl. No.: 11/410,295

(22) Filed: Apr. 25, 2006

(65) Prior Publication Data

US 2006/0258536 A1  Nov. 16, 2006

(30) Foreign Application Priority Data

Apr. 28, 2005 (EP) .................................. 05009271

(51) Int. Cl.
*A01N 43/653* (2006.01)
*C07D 249/12* (2006.01)

(52) U.S. Cl. ..................... 504/273; 548/263.2; 558/413
(58) Field of Classification Search ................. 504/273; 548/263.2; 558/413
See application file for complete search history.

(56) References Cited

U.S. PATENT DOCUMENTS

| | | | |
|---|---|---|---|
| 5,057,144 A | 10/1991 | Daum et al. | |
| 5,061,311 A | 10/1991 | Findeisen et al. | |
| 5,085,684 A | 2/1992 | Müller et al. | |
| 5,238,910 A | 8/1993 | Müller et al. | |
| 5,252,540 A | 10/1993 | Heistracher et al. | |
| 5,256,632 A | 10/1993 | Wolf et al. | |
| 5,300,480 A | 4/1994 | Haas et al. | |
| 5,324,710 A | 6/1994 | Ort et al. | |
| 5,463,081 A | 10/1995 | Ort et al. | |
| 5,534,486 A | 7/1996 | Müller et al. | |
| 5,552,369 A | 9/1996 | Findeisen et al. | |
| 5,610,121 A | 3/1997 | Riebel et al. | |
| 5,861,358 A | 1/1999 | Findeisen et al. | |
| 5,972,844 A | 10/1999 | Müller et al. | |
| 6,180,567 B1 | 1/2001 | Müller et al. | |
| 6,200,931 B1 | 3/2001 | Müller et al. | |
| 6,200,934 B1 | 3/2001 | Müller et al. | |
| 6,251,831 B1* | 6/2001 | Muller et al. ................ 504/273 |
| 6,451,737 B1 | 9/2002 | Gesing et al. | |
| 6,525,211 B1* | 2/2003 | Muller et al. ................ 558/413 |
| 6,677,277 B1 | 1/2004 | Schallner et al. | |

FOREIGN PATENT DOCUMENTS

| | | |
|---|---|---|
| CA | 2 333 068 A1 | 12/1999 |
| CA | 2 189 698 C | 5/2003 |
| DE | 39 34081 A1 | 4/1991 |
| DE | 40 29 753 A1 | 3/1992 |
| DE | 41 10 795 A1 | 10/1992 |
| DE | 195 40 737 A1 | 5/1997 |
| DE | 196 15 900 A1 | 10/1997 |
| DE | 196 21 685 A1 | 12/1997 |
| DE | 196 32 945 A1 | 2/1998 |
| DE | 198 23 131 A1 | 11/1999 |
| DE | 101 17 673 A1 | 10/2002 |
| EP | 0 283 876 A2 | 9/1988 |
| EP | 0 341 489 A1 | 11/1989 |
| EP | 0 422 469 A2 | 4/1991 |
| EP | 0 425 948 A2 | 5/1991 |
| EP | 0 431 291 A2 | 6/1991 |
| EP | 0 507 171 A1 | 10/1992 |
| EP | 0 534 266 A1 | 3/1993 |
| EP | 0 569 810 A1 | 11/1993 |
| WO | WO 91/06541 A1 | 5/1991 |
| WO | WO 92/13845 A1 | 8/1992 |
| WO | WO 93/24482 A1 | 12/1993 |
| WO | WO 94/08979 A1 | 4/1994 |
| WO | WO 95/27703 A1 | 10/1995 |
| WO | WO 96/22982 A1 | 8/1996 |
| WO | WO 97/03056 A1 | 1/1997 |
| WO | WO 97/16449 A1 | 5/1997 |
| WO | WO 97/32861 A1 | 9/1997 |
| WO | WO 97/32876 A1 | 9/1997 |

OTHER PUBLICATIONS

Patini et al., Chem. Rev., 1996, vol. 96, No. 8, p. 3148.*
http://en.wikipedia.org/wiki/Species, published 2010, p. 3 in particular.*
Dialog File 351, Accession No. 8410452, WPI English language abstract of DE 196 15 900 A1 (Document FP23 listed on accompanying PTO/SB/08A), Published Oct. 23, 1997.
English language translation of DE 101 17 673 A1, 94 pages (Document FP28 listed on accompanying PTO/SB/08A), published Oct. 10, 2002.
International Search Report for International Application No. PCT/EP2006/003565, mailed Jul. 6, 2006, European Patent Office, NL.

* cited by examiner

*Primary Examiner*—Susannah Chung
(74) *Attorney, Agent, or Firm*—Sterne, Kessler, Goldstein & Fox P.L.L.C.

(57) ABSTRACT

Sulfonylamino(thio)carbonyl compounds are used to control unwanted plants or to regulate growth in plants. Sulfonylamino(thio)carbonyl compounds are applied to plants, the seed or the area on which the plants are growing to control the growth of such plants.

10 Claims, No Drawings

SULFONYLAMINO(THIO)CARBONYL COMPOUNDS

It is known that substituted sulfonylamino(thio)carbonyl compounds may possess herbicidal properties. These compounds are, for example, phenyl derivatives with single or multiple substitution (e.g., EP 283876, EP 341489, EP 422469, EP 425948, EP 431291, EP 507171, EP 534266, EP 569810, WO 93/24482, WO 94/08979, WO 95/27703, WO 96/22982, WO 97/03056, WO 97/16449, WO 97/32876, DE 03934081, DE 04029753, DE 04110795, DE 10117673, DE 19540737, DE 19615900, DE 19621685, DE 19632945, DE 19823131). The effect of these compounds, however, is not satisfactory in every respect.

Specific iodine-substituted phenylsulfonylamino(thio)carbonyl compounds have now surprisingly been found which are suitable with particular advantage as herbicides or plant growth regulators.

The present invention accordingly provides compounds of the formula (I) and/or salts thereof,

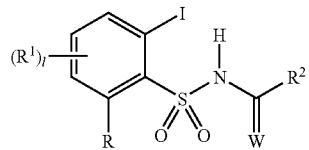

in which

R is a hydrocarbon radical or hydrocarbonoxy radical, preferably a radical from the group consisting of alkyl, alkenyl, alkynyl, cycloalkyl, cycloalkenyl, cycloalkynyl, alkoxy, alkenyloxy, alkynyloxy, cycloalkyloxy, cycloalkenyloxy, aryl and aryloxy, which is unsubstituted or substituted and inclusive of substituents has 1 to 30 carbon atoms, preferably 1 to 20 carbon atoms, or R is a heterocyclyl radical or heterocyclyloxy radical which is unsubstituted or substituted, or R is a hydrogen atom, halogen or a radical $C(O)R^3$, $OC(O)R^3$, $S(O)_nR^3$, $OS(O)_nR^3$, OH, CN, $NO_2$, $NH_2$, $SF_5$, $NR^4R^5$ or $Si(R^6)_3$, where n is 0, 1 or 2, $R^1$ independently at each occurrence is halogen, OH, SH, a carbon-free, nitrogen-containing radical or a carbon-containing radical having 1 to 30 carbon atoms, preferably 1 to 20 carbon atoms, l is 0, 1, 2 or 3, preferably 0, 1 or 2, more preferably 0 to 1, very preferably 0, $R^2$ is a substituted or unsubstituted heterocyclyl radical having 5 ring members, of which preferably at least one is oxygen, sulfur or nitrogen and one to four further ring members may be nitrogen, $R^3$ is a hydrocarbon radical or hydrocarbonoxy radical, preferably a radical from the group consisting of alkyl, alkenyl, alkynyl, cycloalkyl, cycloalkenyl, cycloalkynyl, alkoxy, alkenyloxy, alkynyloxy, cycloalkyloxy, cycloalkenyloxy, aryl and aryloxy, which is unsubstituted or substituted and inclusive of substituents has 1 to 30 carbon atoms, preferably 1 to 20 carbon atoms, or $R^3$ is a heterocyclyl radical or heterocyclyloxy radical which is unsubstituted substituted, or $R^3$ is a hydrogen atom, CN or $NR^4R^5$ ist, $R^4$ is a group of the formula $R^0$-$Q^0$-, in which $R^0$ is a hydrogen atom, an acyl radical, a hydrocarbon radical or a heterocyclyl radical, each of the last-mentioned two radicals being unsubstituted or substituted and inclusive of substituents having 1 to 30 carbon atoms, preferably 1 to 20 carbon atoms, and $Q^0$ is a direct bond or a divalent group of the formula —O— or —N($R^\#$)—, $R^\#$ being a hydrogen atom, an acyl radical or a hydrocarbon radical and the last-mentioned radical being unsubstituted or substituted and inclusive of substituents having 1 to 30 carbon atoms, preferably 1 to 20 carbon atoms, or or $R^0$ and $R^\#$ form with one another a nitrogen-containing heterocyclic ring, $R^5$ is a hydrogen atom, an acyl radical, a hydrocarbon radical or a heterocyclyl radical, each of the last-mentioned two radicals being unsubstituted or substituted and inclusive of substituents having 1 to 30 carbon atoms, preferably 1 to 20 carbon atoms, or $R^4$ and $R^5$ form with one another a nitrogen-containing heterocyclic ring, $R^6$ is a hydrocarbon radical which is unsubstituted or substituted and inclusive of substituents has 1 to 30 carbon atoms, preferably 1 to 20 carbon atoms, preferably ($C_1$-$C_4$) alkyl or ($C_6$-$C_{10}$)aryl, and W is an oxygen atom or a sulfur atom.

The compounds of the formula (I) may form salts, examples being those in which the hydrogen of the —$SO_2$—NH— group is replaced by an agriculturally suitable cation. These salts are, for example, metal salts, especially alkali metal salts or alkaline earth metal salts, particularly sodium and potassium salts, or else ammonium salts or salts with organic amines. Formation of salts may likewise take place by addition of an acid onto basic groups, such as amino and alkylamino. Suitable acids for this purpose are strong organic and inorganic acids, such as HCl, HBr, $H_2SO_4$ or $HNO_3$, for example.

Carbon-containing radicals are organic radicals which contain at least one carbon atom, preferably 1 to 30 carbon atoms, more preferably 1 to 20 carbon atoms, and also at least one atom of one or more other elements of the Periodic Table of the Elements, such as H, Si, N, P, O, S, F, Cl, Br or I. Examples of carbon-containing radicals are unsubstituted or substituted hydrocarbon radicals, which may be attached to the parent structure directly or via a heteroatom such as N, S, P or O, unsubstituted or substituted heterocyclyl radicals which may be attached to the parent structure directly or via a heteroatom such as N, S, P or O, carbon-containing acyl radicals or cyano.

In formula (I) and all subsequent formulae the carbon-containing radicals such as alkyl, alkoxy, haloalkyl, haloalkoxy, alkylamino and alkylthio and also the corresponding unsaturated and/or substituted radicals in the carbon skeleton are in each case linear or branched. Unless specifically indicated, for these radicals the lower carbon frameworks, with 1 to 6 carbon atoms or, in the case of unsaturated groups, with 2 to 6 carbon atoms, for example, are preferred. Alkyl radicals, both alone and in composite definitions such as alkoxy, haloalkyl, etc., are for example methyl, ethyl, n-propyl or isopropyl, n-butyl, isobutyl, tert-butyl or 2-butyl, pentyls, hexyls, such as n-hexyl, isohexyl, and 1,3-dimethylbutyl, heptyls, such as n-heptyl, 1-methylhexyl and 1,4-dimethylpentyl; alkenyl and alkynyl radicals have the definition of the possible unsaturated radicals corresponding to the alkyl radicals; alkenyl is for example allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is for example propargyl, but-2-yn-1-yl, but-3-yn-1-yl, and 1-methylbut-3-yn-1-yl.

Alkenyl in the form $(C_3-C_4)$alkenyl, $(C_3-C_5)$alkenyl, $(C_3-C_6)$alkenyl, $(C_3-C_8)$alkenyl or $(C_3-C_{12})$alkenyl is preferably an alkenyl radical having 3 to 4, 3 to 5, 3 to 6, 3 to 8 or 3 to 12 carbon atoms, respectively, in which the double bond is not at the carbon atom joined to the remainder of the molecule of the compound (I) ("yl" position). Similar comments apply to $(C_3-C_4)$alkynyl etc., $(C_3-C_4)$alkenyloxy etc., and $(C_3-C_4)$alkynyloxy etc.

Cycloalkyl is a carbocyclic, saturated ring system having preferably 3-8 carbon atoms, e.g., cyclopropyl, cyclobutyl, cyclopentyl or cyclohexyl.

Carbon-free, nitrogen-containing radicals are radicals which contain preferably 1 to 10 nitrogen atoms, more preferably 1 or 2 nitrogen atoms, and additionally, preferably, one or more atoms of one or more non-carbon elements of the Periodic Table of the Elements, such as H, O or S. Examples of carbon-free, nitrogen-containing radicals are $NH_2$, $NO_2$, NHOH, NO, NH—$NH_2$ or $N_3$.

Halogen is for example fluorine, chlorine, bromine or iodine. Haloalkyl, -alkenyl and -alkynyl are alkyl, alkenyl or alkynyl, respectively, each of which is fully or partly substituted by halogen, preferably by fluorine, chlorine and/or bromine, in particular by fluorine or chlorine, examples being $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$ and $OCH_2CH_2Cl$; similar comments apply to haloalkenyl and other halogen-substituted radicals.

A hydrocarbon radical is a linear, branched or cyclic, saturated or unsaturated, aliphatic or aromatic hydrocarbon radical, e.g., alkyl, alkenyl, alkynyl, cycloalkyl, cycloalkenyl or aryl; aryl is a monocyclic, bicyclic or polycyclic aromatic system, examples being phenyl, naphthyl, tetrahydronaphthyl, indenyl, indanyl, pentalenyl, fluorenyl and the like, preferably phenyl;

a hydrocarbon radical is preferably alkyl, alkenyl or alkynyl having up to 12 carbon atoms or cycloalkyl having 3, 4, 5, 6 or 7 ring atoms, or phenyl.

A heterocyclic radical or ring (heterocyclyl) can be saturated, unsaturated or heteroaromatic and unsubstituted or substituted; it contains preferably one or more heteroatoms in the ring, preferably from the group N, O and S; preferably it is an aliphatic heterocyclyl radical having 3 to 7 ring atoms or a heteroaromatic radical having 5 or 6 ring atoms, and contains 1, 2 or 3 heteroatoms. The heterocyclic radical may be, for example, a heteroaromatic radical or ring (heteroaryl), such as a monocyclic, bicyclic or polycyclic aromatic system in which at least one ring contains one or more heteroatoms, examples being pyridyl, pyrimidinyl, pyridazinyl, pyrazinyl, triazinyl, thienyl, thiazolyl, oxazolyl, furyl, pyrrolyl, pyrazolyl and imidazolyl, or is a partly or fully hydrogenated radical such as oxiranyl, oxetanyl, pyrrolidyl, piperidyl, piperazinyl, dioxolanyl, morpholinyl or tetrahydrofuryl. Suitable substituents for a substituted heterocyclic radical are the substituents specified later on below, and oxo as well. The oxo group may also occur on the ring heteroatoms, which can exist in different oxidation states, in the case of N and S, for example.

Substituted radicals, such as substituted hydrocarbon radicals, e.g., substituted alkyl, alkenyl, alkynyl, aryl, phenyl, and benzyl, or substituted heterocyclyl or heteroaryl, are for example a substituted radical derived from the unsubstituted parent structure, the substituents being, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl, and, in the case of cyclic radicals, alkyl and haloalkyl as well, and also unsaturated aliphatic radicals corresponding to the stated saturated, hydrocarbon-containing radicals, such as alkenyl, alkynyl, alkenyloxy, alkynyloxy etc. In the case of radicals containing carbon atoms preference is given to those having 1 to 4 carbon atoms, particularly 1 or 2 carbon atoms. Preference is generally given to substituents from the group consisting of halogen, such as fluorine and chlorine $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro, and cyano. Particular preference here is given to the substituents methyl, methoxy, and chlorine. Optionally substituted phenyl is preferably phenyl which is unsubstituted or is substituted one or more times, preferably up to three times, by identical or different radicals from the group consisting of halogen, $(C_1-C_4)$alkyl, $(C_1-C_4)$alkoxy, $(C_1-C_4)$haloalkyl, $(C_1-C_4)$haloalkoxy, and nitro, examples being o-, m- and p-tolyl, dimethylphenyls, 2-, 3- and 4-chlorophenyl, 2-, 3- and 4-trifluoro- and -trichlorophenyl, 2,4-, 3,5-, 2,5-, and 2,3-dichlorophenyl, and o-, m- and p-methoxyphenyl.

Monosubstituted or disubstituted amino is a chemically stable radical from the group of substituted amino radicals, which are N-substituted by, for example, one radical or two identical or different radicals from the group consisting of alkyl, alkoxy, acyl and aryl; preferably monoalkylamino, dialkylamino, acylamino, arylamino, N-alkyl-N-arylamino, and N-heterocycles; preference is given here to alkyl radicals having 1 to 4 carbon atoms; aryl here is preferably phenyl or substituted phenyl; acyl is subject to the definition given later on below, preferably formyl, $(C_1-C_4)$alkylcarbonyl or $(C_1-C_4)$alkylsulfonyl. Similar comments apply to substituted hydroxylamino or hydrazino.

An acyl radical is the radical of an organic acid formed formally by elimination of an OH group from the organic acid, such as the radical of a carboxylic acid and radicals of acids derived therefrom, such as of thiocarboxylic acid, optionally N-substituted iminocarboxylic acids, or the radicals of carbonic monoesters, or optionally N-substituted carbamic acids, sulfonic acids, sulfinic acids, phosphonic acids or phosphinic acids.

An acyl radical is preferably formyl or aliphatic acyl from the group CO—$R^x$, CS—$R^x$, CO—$OR^x$, CS—$OR^x$, CS—$SR^x$, $SOR^Y$ or $SO_2R^Y$, where $R^x$ and $R^Y$ are each a $C_1-C_{10}$ hydrocarbon radical which is unsubstituted or substituted, or aminocarbonyl or aminosulfonyl, the two last-mentioned radicals being unsubstituted, N-monosubstituted or N,N-disubstituted.

Acyl is for example formyl, haloalkylcarbonyl, alkylcarbonyl such as $(C_1-C_4)$alkylcarbonyl, phenylcarbonyl, it being possible for the phenyl ring to be substituted, for example as indicated above for phenyl, or alkyloxycarbonyl, phenyloxycarbonyl, benzyloxycarbonyl, alkylsulfonyl, alkylsulfinyl, N-alkyl-1-iminoalkyl, and other radicals of organic acids.

The invention also provides all stereoisomers that are embraced by formula (I), and mixtures thereof. Such compounds of the formula (I) contain one or more asymmetric carbon atoms or else double bonds, which are not indicated separately in the general formula (I). The possible stereoisomers, defined by their specific three-dimensional form, such as enantiomers, diastereomers, Z-isomers, and E isomers, are all embraced by the formula (I) and may be obtained by customary methods from mixtures of the stereoisomers, or else prepared by stereoselective reactions in combination with the use of stereochemically pure starting materials.

The above examples of radicals or radical ranges which are subsumed under the general terms such as "alkyl", "acyl", "substituted radicals", etc., do not constitute a complete enumeration. The general terms also embrace the definitions, given later on below, of radical ranges in groups of preferred compounds, especially radical ranges which embrace specific radicals from the tabular examples.

Preferred compounds of the invention, of the formula (I), and/or salts thereof are those in which R is $(C_1-C_6)$alkyl, $(C_2-C_6)$alkenyl, $(C_2-C_6)$alkynyl, $(C_3-C_6)$cycloalkyl, $(C_3-C_6)$cycloalkenyl, $(C_3-C_6)$cycloalkynyl, $(C_1-C_6)$alkyloxy, $(C_2-C_6)$alkenyloxy, $(C_2-C_6)$alkynyloxy, $(C_3-C_6)$cycloalkyloxy, phenyl, phenyloxy, H, F, Cl, Br, I, OH, CN, $NO_2$, $NH_2$, $SF_5$, $C(O)R^3$, $Si((C_1-C_6)alkyl)_3$, $N((C_1-C_6)alkyl)_2$, $NH(C_1-C_6)$alkyl, $N((C_2-C_6)alkenyl)_2$, $NH(C_2-C_6)$alkenyl, $N((C_2-C_6)alkynyl)_2$, $NH(C_2-C_6)$alkynyl, $NH((C_3-C_6)cycloalkyl)_2$, $NH(C_3-C_6)$cycloalkyl, $N(C_1-C_6)alkyl(C_3-C_6)$cycloalkyl, $N(C_1-C_6)$alkyl $C(O)R^3$, $NHC(O)R^3$, $N(C_1-C_6)$alkyl $S(O)_nR^3$, $NHS(O)_nR^3$, $S(O)_n(C_1-C_4)$alkyl, $S(O)_n(C_3-C_6)$cycloalkyl, $S(O)_n(C_1-C_6)$alkenyl, $S(O)_n(C_1-C_6)$alkynyl, $S(O)_nNHR^3$, $S(O)_nN(C_1-C_6)$alkyl $R^3$, $OSO_2(C_1-C_6)$alkyl, $OSO_2(C_3-C_6)$cycloalkyl, $OSO_2(C_1-C_6)$alkenyl, $OSO_2(C_1-C_6)$alkynyl, $OS(O)_n$phenyl, $OSO_2N((C_1-C_6)alkyl)_2$, $OSO_2NH(C_1-C_6)$alkyl, $OSO_2N((C_3-C_6)cycloalkyl)_2$, $OSO_2NH(C_3-C_6)$cycloalkyl, $OSO_2N((C_2-C_6)alkenyl)_2$, $OSO_2NH(C_2-C_6)$alkenyl, $OSO_2N((C_2-C_6)alkynyl)_2$, $OSO_2NH(C_2-C_6)$alkynyl, $OC(O)R^3$ or heterocyclyl, the stated radicals alkyl, alkenyl, alkynyl, cycloalkyl, cycloalkenyl, cycloalkynyl, alkyloxy, alkenyloxy, alkynyloxy, cycloalkoxy, phenyl, phenyloxy and heterocyclyl being unsubstituted or substituted, e.g., by one or more radicals from the group consisting of halogen, CN, $(C_1-C_6)$alkyl, $(C_2-C_6)$alkenyl, $(C_2-C_6)$alkynyl, $(C_1-C_6)$alkoxy, $(C_3-C_6)$cycloalkyl, phenyl, phenyloxy, and heterocyclyloxy, with the two last-mentioned radicals possible being substituted one or more times by radicals from the group consisting of halogen, CN, methyl, methoxy, trifluoromethyl, and trifluoromethoxy, n is 0, 1 or 2, and $R^3$ is H, $(C_1-C_6)$alkyl, $(C_2-C_6)$alkenyl, $(C_2-C_6)$alkynyl, $(C_3-C_6)$cycloalkyl, $(C_1-C_6)$alkyloxy, $(C_2-C_6)$alkenyloxy, $(C_2-C_6)$alkynyloxy, $(C_3-C_6)$-cycloalkyloxy, phenyl, heterocyclyl, CN, $NH(C_1-C_6)$alkyl or $N((C_1-C_6)alkyl)_2$, the stated radicals alkyl, alkenyl, alkynyl, cycloalkyl, alkyloxy, alkenyloxy, alkynyloxy, cycloalkyloxy, phenyl, and heterocyclyl being unsubstituted or substituted, e.g., by one or more radicals from the group consisting of halogen, CN, $(C_1-C_6)$akyl, $(C_1-C_6)$alkenyl, $(C_1-C_6)$alkynyl, and $(C_1-C_6)$alkyloxy, $R^1$ independently at each occurrence is $(C_1-C_6)$alkyl, $(C_1-C_6)$haloalkyl, $(C_1-C_6)$alkyloxy, $(C_1-C_6)$haloalkoxy or halogen, I is 0, 1 or 2, preferably 0 or 1, more preferably 0, $R^2$ is in each case optionally substituted heterocyclyl, preferably of the following formulae

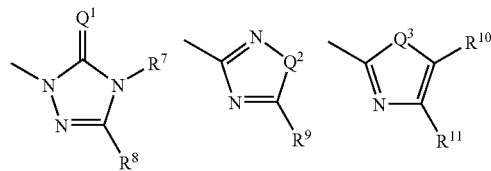

in which $Q^1$, $Q^2$ and $Q^3$ are each oxygen or sulfur, and $R^7$ is hydrogen, hydroxy, amino, cyano, is $(C_2-C_{10})$alkylideneamino, is $(C_1-C_6)$alkyl optionally substituted by fluorine, chlorine, bromine, cyano, $(C_1-C_4)$alkoxy, $(C_1-C_4)$alkyl-carbonyl or $(C_1-C_4)$alkoxycarbonyl, is $(C_2-C_6)$alkenyl or $(C_2-C_6)$alkynyl each of which is optionally substituted by fluorine, chlorine and/or bromine, is $(C_1-C_6)$alkoxy, $(C_1-C_6)$alkylamino or $(C_1-C_6)$alkyl-carbonylamino, each of which is optionally substituted by fluorine, chlorine, bromine, cyano, $(C_1-C_4)$alkoxy or $(C_1-C_4)$alkoxy-carbonyl, is $(C_3-C_6)$alkenyloxy, is $di((C_1-C_4)alkyl$(amino), is $(C_3-C_6)$cycloalkyl, $(C_3-C_6)$cycloalkylamino or $(C_3-C_6)$cycloalkyl-$(C_1-C_4)$alkyl, each of which is optionally substituted by fluorine, chlorine, bromine, cyano and/or $(C_1-C_4)$alkyl, or is phenyl or phenyl-$(C_1-C_4)$alkyl each of which is optionally substituted by fluorine, chlorine, bromine, cyano, nitro, $(C_1-C_4)$alkyl, trifluoromethyl and/or $(C_1-C_4)$alkoxy, $R^8$ is hydrogen, hydroxy, mercapto, amino, cyano, fluorine, chlorine, bromine, iodine, is $(C_1-C_6)$alkyl optionally substituted by fluorine, chlorine, bromine, cyano, $(C_1-C_4)$alkoxy, $(C_1-C_4)$alkyl-carbonyl or $(C_1-C_4)$alkoxy-carbonyl, is $(C_2-C_6)$alkenyl or $(C_2-C_6)$alkynyl each of which is optionally substituted by fluorine, chlorine and/or bromine, is $(C_1-C_6)$alkoxy, $(C_1-C_6)$alkylthio, $(C_1-C_6)$alkylamino or $(C_1-C_6)$alkyl-carbonylamino each of which is optionally substituted by fluorine, chlorine, cyano $(C_1-C_4)$alkoxy or $(C_1-C_4)$alkoxycarbonyl, is $(C_3-C_6)$alkenyloxy, $(C_3-C_6)$alkynyloxy, $(C_3-C_6)$alkenylthio, $(C_3-C_6)$alkynylthio, $(C_3-C_6)$alkenylamino or $(C_3-C_6)$alkynylamino, is $di((C_1-C_4)alkyl)$amino, is aziridino, pyrrolidino, piperidino or morpholino each of which is optionally substituted by methyl and/or ethyl, is $(C_3-C_6)$cycloalkyl, $(C_5-C_6)$cycloalkenyl, $(C_3-C_6)$cycloalkyloxy, $(C_3-C_6)$cycloalkylthio, $(C_3-C_6)$cycloalkylamino, $(C_3-C_6)$cycloalkyl-$(C_1-C_4)$alkyl, $(C_3-C_6)$cycloalkyl-$(C_1-C_4)$alkoxy, $(C_3-C_6)$cycloalkyl-$(C_1-C_4)$alkylthio or $(C_3-C_6)$cycloalkyl-$(C_1-C_4)$alkylamino, each of which is optionally substituted by fluorine, chlorine, bromine, cyano and/or $(C_1-C_4)$alkyl, or is phenyl, phenyl-$(C_1-C_4)$alkyl, phenoxy, phenyl-$(C_1-C_4)$alkoxy, phenylthio, phenyl-$(C_1-C_4)$alkylthio, phenylamino or phenyl-$(C_1-C_4)$alkylamino each of which is optionally substituted by fluorine, chlorine, bromine, cyano, nitro, $(C_1-C_4)$alkyl, trifluoromethyl, $(C_1-C_4)$alkoxy and/or $(C_1-C_4)$alkoxycarbonyl, or $R^7$ and $R^8$ together are optionally branched alkanediyl having 3 to 11 carbon atoms, and additionally $R^9$, $R^{10}$ and $R^{11}$ are identical or different and are hydrogen, cyano, fluorine, chlorine, bromine, or are alkyl, alkenyl, alkynyl, alkoxy, alkenyloxy, alkynyloxy, alkylthio, alkenylthio, alkynylthio, alkylsulfinyl or alkylsulfonyl having in each case up to 6 carbon atoms, or are cycloalkyl having 3 to 6 carbon atoms and being optionally substituted by cyano, fluorine, chlorine, bromine or $(C_1-C_4)$alkyl, and W is an oxygen atom.

Particularly preferred compounds of the formula (I) and/or salts thereof are those in which R is $(C_1-C_4)$alkyl, $(C_2-C_4)$alkenyl, $(C_2-C_4)$alkynyl, $(C_3-C_6)$cycloalkyl, $(C_1-C_4)$alkyloxy, $(C_2-C_4)$alkenyloxy, $(C_2-C_4)$alkynyloxy, $(C_3-C_6)$cycloalkyloxy, phenyl, phenyloxy, H, F, Cl, Br, I, $C(O)R^3$, CN, $NO_2$, $NH_2$, $N((C_1-C_4)alkyl)_2$, $NH(C_1-C_4)$alkyl, $NH(C_2-C_4)$alkenyl, $NH(C_2-C_4)$alkynyl, $NH(C_3-C_6)$cycloalkyl, $N(C_1-C_4)alkyl(C_3-C_6)$cycloalkyl, $S(C_1-C_4)$alkyl, $S(C_2-C_4)$alkenyl, $S(C_2-C_4)$alkynyl, $S(C_3-C_6)$cycloalkyl, $S(O)(C_1-C_4)$alkyl, $S(O)(C_1-C_4)$alkenyl, $S(O)(C_2-C_4)$alkynyl, $S(O)(C_3-C_6)$cycloalkyl, $SO_2(C_1-C_4)$alkyl, $SO_2(C_2-C_4)$alkenyl, $SO_2(C_2-C_4)$alkynyl, $SO_2(C_3-C_6)$cycloalkyl, $SO_2NH(C_1-C_4)$alkyl, $SO_2N((C_1-C_4)alkyl)_2$, $SO_2NH(C_3-C_6)$cycloalkyl, $OSO_2(C_1-C_4)$alkyl, $OSO_2NH(C_1-C_4)$alkyl, $OSO_2N((C_1-C_4)alkyl)_2$ or $NHC(O)R^3$, $NHSO_2R^3$, $OC(O)R^3$, $R^3$ being H, $(C_1-C_4)$alkyl, ($C_2$-$C_4$)alkenyl, ($C_2$-$C_4$)alkynyl, ($C_3$-$C_6$)cycloalkyl, ($C_1$-$C_4$)alkyloxy, ($C_2$-$C_4$)alkenyloxy, ($C_2$-$C_4$)alkynyloxy, ($C_3$-$C_6$)cycloalkyloxy, ($C_1$-$C_4$)haloalkyl, $NH(C_1$-$C_4)$alkyl or $N((C_1$-$C_4)$alkyl$)_2$, the stated radicals alkyl, alkenyl, alkynyl, cycloalkyl, alkyloxy, alkenyloxy, alkynyloxy, cycloalkyloxy, phenyl and phenyloxy being unsubstituted or substituted by, for example, one or more radicals, preferably one, two or three radicals, from the group consisting of halogen (F, Cl, Br, I), ($C_1$-$C_4$)alkyl, ($C_1$-$C_4$)alkyloxy, ($C_1$-$C_4$)haloalkyl($C_1$-$C_4$)haloalkyloxy and ($C_3$-$C_6$)cycloalkyl, $R^1$ is halogen (F, Cl, Br, I), ($C_1$-$C_4$)alkyl, ($C_1$-$C_4$)alkyloxy, ($C_1$-$C_4$)haloalkyl or ($C_1$-$C_4$)haloalkyloxy, l is 0 or 1, preferably 0, $R^2$ is in each case optionally substituted heterocyclyl, preferably of the following formulae

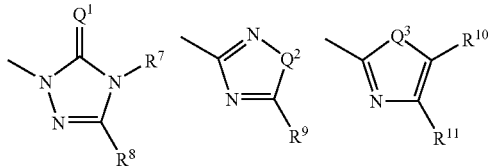

in which $Q^1$, $Q^2$ and $Q^3$ are each oxygen or sulfur and $R^7$ is hydrogen, hydroxy, amino, is ($C_3$-$C_8$)alkylideneamino, is methyl, ethyl, n-propyl or isopropyl, n-butyl, isobutyl, sec-butyl or tert-butyl in each case optionally substituted by fluorine, chlorine, cyano, methoxy or ethoxy, is propenyl, butenyl, propynyl or butynyl in each case optionally substituted by fluorine, chlorine or bromine, is methoxy, ethoxy, n-propoxy or isopropoxy, n-butoxy, isobutoxy, sec-butoxy or tert-butoxy, methylamino, ethylamino, n-propylamino or isopropylamino, n-butylamino, isobutylamino, sec-butylamino or tert-butylamino, in each case optionally substituted by fluorine, chlorine, cyano, methoxy or ethoxy, is propenyloxy or butenyloxy, is dimethylamino or diethylamino, is cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl in each case optionally substituted by fluorine, chlorine, methyl and/or ethyl, or is phenyl or benzyl in each case optionally substituted by fluorine, chlorine, methyl, trifluoromethyl and/or methoxy, $R^8$ is hydrogen, hydroxy, mercapto, amino, fluorine, chlorine, bromine, is methyl, ethyl, n-propyl or isopropyl, n-butyl, isobutyl, sec-butyl or tert-butyl in each case optionally substituted by fluorine, chlorine, cyano, methoxy or ethoxy, is ethenyl, propenyl, butenyl, propynyl or butynyl in each case optionally substituted by fluorine, chlorine or bromine, is methoxy, ethoxy, n-propoxy or isopropoxy, n-butoxy, isobutoxy, sec-butoxy or tert-butoxy, methylthio, ethylthio, n-propylthio or isopropylthio, n-butylthio, isobutylthio, sec-butylthio or tert-butylthio, methylamino, ethylamino, n-propylamino or isopropylamino, n-butylamino, isobutylamino, sec-butylamino or tert-butylamino, in each case optionally substituted by fluorine, chlorine, cyano, methoxy or ethoxy, is propenyloxy, butenyloxy, propynyloxy, butynyloxy, propenylthio, propadienylthio, butenylthio, propynylthio, butynylthio, propenylamino, butenylamino, propynylamino or butynylamino, is dimethylamino, diethylamino or dipropylamino, is cyclopropyl cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropyl methyl, cyclobutyl methyl, cyclopentyl methyl, cyclohexyl methyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino in each case optionally substituted by fluorine, chlorine, methyl and/or ethyl, or is phenyl, benzyl, phenoxy, benzyloxy, phenylthio, benzylthio, phenylamino or benzylamino in each case optionally substituted by fluorine, chlorine, methyl, trifluoromethyl, methoxy and/or methoxycarbonyl, or $R^7$ and $R^8$ together are optionally branched alkanediyl having 3 to 11 carbon atoms, and additionally $R^9$, $R^{10}$ and $R^{11}$ are identical or different and are hydrogen, cyano, fluorine, chlorine, bromine, or are methyl, ethyl, n-propyl or isopropyl, n-butyl, isobutyl, sec-butyl or tert-butyl, propenyl, butenyl, propynyl, butynyl, methoxy, ethoxy, n-propoxy or isopropoxy, n-butoxy, isobutoxy, sec-butoxy or tert-butoxy, propenyloxy, butenyloxy, propynyloxy, butynyloxy, methylthio, ethylthio, n-propylthio or isopropylthio, n-butylthio, isobutylthio, sec-butylthio or tert-butylthio, propenylthio, butenylthio, propynylthio, butynylthio, methylsulfinyl, ethylsulfinyl, methylsulfonyl or ethylsulfonyl, each of which is optionally substituted by fluorine, chlorine, methoxy or ethoxy, or are cyclopropyl, and W is a hydrogen atom.

Especially preferred compounds of the invention, of the formula (I), and/or salts thereof, are those in which R is $CH_3$, $CH_2CH_3$, $(CH_2)_2CH_3$, $CH(CH_3)_2$, $C(CH_3)_3$, $CH=CH_2$, $C\equiv CH$, $CH_2CH=CH_2$, $CH_2C\equiv CH$, cyclopropyl, phenyl, H, F, Cl, Br, I, CN, $NO_2$, $NH_2$, $CH_2OCH_3$, $CF_3$, $CHF_2$, $C(O)H$, $C(O)CH_3$, $C(O)CH_2CH_3$, $C(O)OCH_3$, $C(O)OCH_2CH_3$, $NHCH_3$, $N(CH_3)_2$, NH-cyclopropyl, $N(CH_3)$-cyclopropyl, $NHC(O)H$, $NHC(O)CH_3$, $NHC(O)OCH_3$, $NHSO_2CH_3$, $NHSO_2CF_3$, $NHSO_2CHF_2$, $OCH_3$, $OCH_2CH_3$, $O(CH_2)_2CH_3$, $OCH(CH_3)_2$, $O(CH_2)_3CH_3$, $OCH_2CH(CH_3)_2$, $OCH(CH_3)CH_2CH_3$, $OC(CH_3)_3$, $OCH=CH_2$, $OC\equiv CH$, $OCH_2CH=CH_2$, $OCH_2C\equiv CH$, O-cyclopropyl, $OCH_2$-cyclopropyl, $O(CH_2)_2Cl$, $O(CH_2)_3Cl$, $OCH_2OCH_3$, Ophenyl, $OCH_2$phenyl, $OCF_3$, $OCHF_2$, $OCH_2F$, $OCH_2CF_3$, $OCH_2CHF_2$, $OCH(CH_3)CF_3$, $OCH_2CF_2CF_3$, $SCH_3$, $SCH_2CH_3$, $S(O)CH_3$, $S(O)CH_2CH_3$, $SO_2CH_3$, $SO_2CH_2CH_3$, $SO_2NHCH_3$, $SO_2N(CH_3)_2$, $SO_2NHCF_3$, $SO_2NHCHF_2$, $OSO_2CH_3$, $OSO_2CF_3$, $OSO_2CHF_2$, $OSO_2N(CH_3)_2$, $OSO_2NHCF_3$, $OSO_2NHCHF_2$, $OC(O)H$, $OC(O)CH_3$, $OC(O)OCH_3$, $OC(O)N(CH_3)_2$, l is 0, $R^2$ is optionally substituted triazolinyl, preferably of the following formula

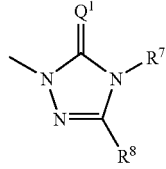

in which $Q^1$ is oxygen or sulfur, and $R^7$ is methyl, ethyl, n-propyl or isopropyl each of which is optionally substituted by fluorine, chlorine, cyano, methoxy or ethoxy, is propenyl or propynyl, is methoxy, ethoxy, n-propoxy or isopropoxy, or is cyclopropyl, $R^8$ is hydrogen, chlorine, brome, is methyl, ethyl, n-propyl or isopropyl each of which is optionally substituted by fluorine, chlorine, cyano, methoxy or ethoxy, is propenyl or propynyl each of which is optionally substituted by fluorine and/or chlorine, is methoxy, ethoxy, n-propoxy or isopropoxy, methylthio, ethylthio, n-propylthio or isopropylthio, each of which is optionally substituted by fluorine, chlorine, cyano, methoxy or ethoxy, or is propenyloxy or cyclopropyl, and W is oxygen.

Particular preference is also given to compounds of the invention of the formula (I) and salts thereof which contain a combination of radicals from the preferred compounds specified above, and to those which contain individual or multiple radicals from the compounds listed in table 1 of this description.

The present invention also provides processes for preparing the compounds of the invention of the formula (I) and/or salts thereof, comprising (a) reacting an aminosulfonyl compound of the formula (II)

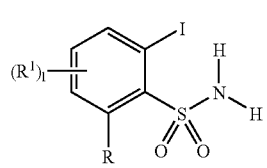
(II)

with a (thio)carboxylic acid derivative of the formula (III)

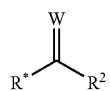
(III)

in which $R^*$ is halogen or an unsubstituted or substituted $(C_1-C_{20})$ hydrocarbonoxy radical, such as unsubstituted or substituted alkoxy, aryloxy, aralkoxy or alkylaryloxy, preferred substituents for the four last-mentioned radicals being halogen, $(C_1-C_4)$alkyl, $(C_1-C_4)$alkyloxy and $(C_1-C_4)$haloalkyl, $R^*$ preferably being fluorine, chlorine, bromine, $(C_1-C_6)$alkoxy, $(C_6-C_{10})$aryloxy, $(C_6-C_{10})$aryl $(C_1-C_6)$alkoxy or $(C_1-C_6)$alkyl$(C_6-C_{10})$aryloxy, optionally in the presence of a reaction auxiliary, in particular an acid acceptor, and optionally in the presence of a diluent, or (b) reacting a sulfonyliso(thio)cyanate of the formula (IV)

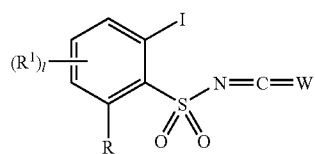
(IV)

with a heterocyclyl compound of the formula (V)

H—$R^2$ (V)

optionally in the presence of a reaction auxiliary and optionally in the presence of a diluent, or (c) reacting a halosulfonyl compound of the formula (VI)

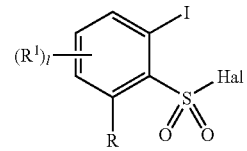
(VI)

with a heterocyclyl compound of the formula (V)

H—$R^2$ (V)

and a metal (thio)cyanate of the formula (VII)

MWCN (VII)

in which

M is a cation, such as an ammonium cation or alkali metal cation, preferably a sodium or potassium ion, and W is an oxygen atom or a sulfur atom, optionally in the presence of a reaction auxiliary and optionally in the presence of a diluent, or (d) reacting a halosulfonyl compound of the formula (VI)

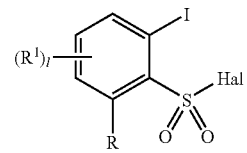
(VI)

with a (thio)carboxamide of the formula (VIII).

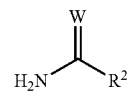
(VIII)

optionally in the presence of a reaction auxiliary, in particular an acid acceptor, and optionally in the presence of a diluent, or (e) reacting a sulfonylamino(thio)carbonyl compound of the formula (IX)

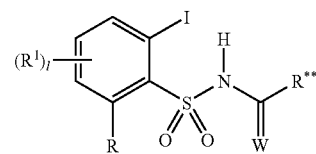
(IX)

in which

R** is halogen or an unsubstituted or substituted ($C_1$-$C_{20}$) hydrocarbonoxy radical such as unsubstituted or substituted alkoxy, aryloxy, aralkoxy or alkylaryloxy, preferred substituents for the four last-mentioned radicals being halogen, ($C_1$-$C_4$)alkyl, ($C_1$-$C_4$)alkyloxy and ($C_1$-$C_4$)haloalkyl, R* preferably being fluorine, chlorine, bromine, ($C_1$-$C_6$)alkoxy, ($C_6$-$C_{10}$)aryloxy, ($C_6$-$C_{10}$)aryl ($C_1$-$C_6$) alkoxy or ($C_1$-$C_6$)alkyl($C_6$-$C_{10}$)aryloxy, with a heterocyclyl compound of the formula (V)

optionally in the presence of reaction auxiliary, in particular an acid acceptor, and optionally in the presence of a diluent, and optionally converting the compound of the formula (I) obtained by process (a), (b), (c), (d) or (e) into a salt by customary methods, the radicals, groups, and indices R, $R^1$, $R^2$, W and I in the formulae (II)-(IX) being defined as in formula (I), and also the same ranges of preference applying as indicated for formula (I).

The reaction of the compounds of the formula (II) and (III) in accordance with version a) takes place preferably under base catalysis in an inert organic solvent, such as dichloromethane, acetonitrile, dioxane or THF, at temperatures between 0° C. and the boiling point of the solvent, preferably at room temperature (cf. DE 19621685). The base used comprises, for example, organic amine bases, such as 1,8-diazabicyclo[5.4.0]undec-7-ene (DBU), alkali metal tert-butoxides, such as NaO-t-$C_4H_9$, or alkali metal hydroxides, such as NaOH, particularly when R*=(substituted) aryloxy (cf. EP 44 807), or trialkylaluminum such as trimethylaluminum or triethylaluminum, the latter in particular when R* is alkyloxy (cf. EP 166 516). The respective base is used, for example, in the range from 1 to 3 mole equivalents, based on the compound of formula (II) (scheme 0).

Scheme 0

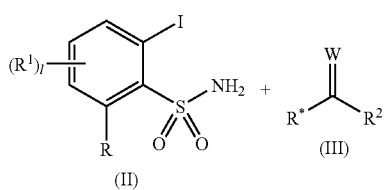

The sulfonamides of the formula (II), the compounds of the formulae (IV), (VI) and (IX), and the compounds of the formula (XIV) described below are new compounds, which, like their preparation and their use for preparing compounds of the formula (I) and/or salts thereof, are provided by the present invention.

The compounds of the formula (II) can be obtained, for example, as shown in schemes 1 to 8 below.

Scheme 1

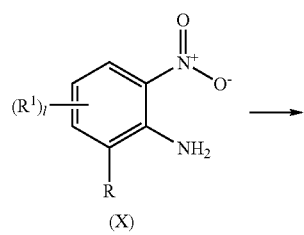

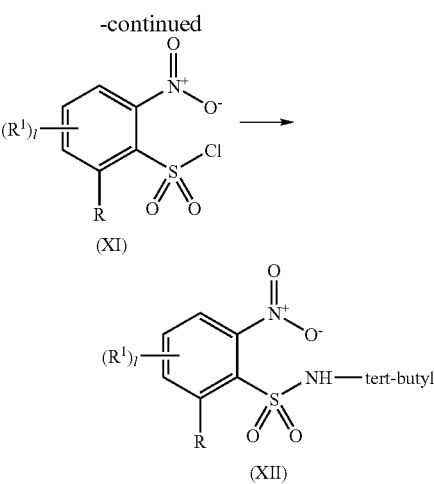

Starting from commercially available compounds of the formula (X) it is possible, such as by diazotizing the amino group with an alkali metal nitrite, e.g., sodium nitrite, in the presence of hydrochloric acid at temperatures between −10° C. and 10° C., and by subsequent exchange of the resulting diazo group with, for example, sulfur dioxide in the presence of a diluent, such as dichloromethane, 1,2-dichloroethane or acetic acid, and in the presence of a catalyst, such as copper(I) chloride and/or copper(II) chloride, at temperatures between −10° C. and 50° C., to obtain the compounds of the formula (XI) (cf. Meerwein, Chem. Ber. 1957, 90, 841) (scheme 1).

By treating sulfochlorides of the formula (XI) with tert-butylamine it is possible to obtain sulfonamides of the formula (XII). The formation of sulfonamide is carried out in, for example, inert solvents, such as dichloromethane, tetrahydrofuran (THF), dioxane, toluene or dimethylformamide (DMF), at temperatures between −70° C. up to the boiling point of the solvent used, preferably at 25° C. The amount of amine employed here is preferably 1.5-2.5 equivalents based on the sulfochloride used.

Scheme 2

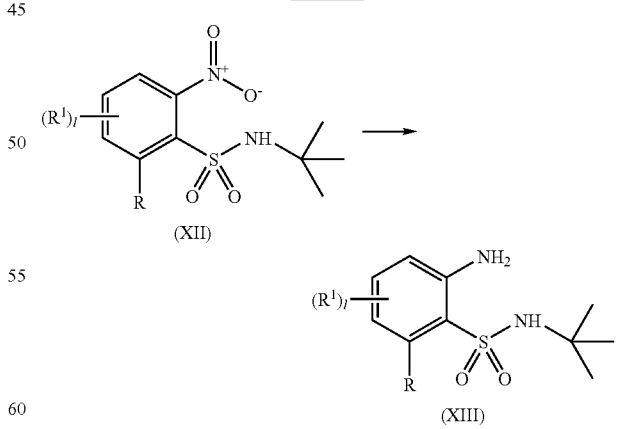

The reduction of the nitro compounds (XII) to the amines of the formula (XIII) takes place in the same way as by known methods (in this regard cf. Houben-Weyl, "Methoden der Organischen Chemie", 4th ed., vol. XI/1 p. 360 ff., Thieme Verlag Stuttgart, 1957) (Scheme 2).

Scheme 3

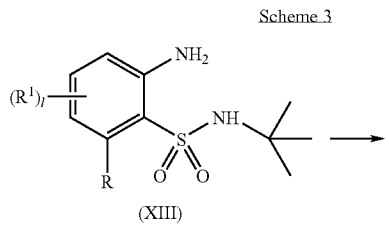

(XIII)

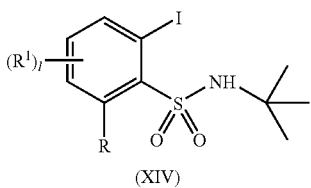

(XIV)

The compounds of the formula (XIII) can be diazotized under customary conditions for diazotization reactions and then converted into compounds of the formula (XIV). By way of example the diazotization takes place in the presence of the acid $H^+X^-$, where $X^-$ is preferably $Cl^-$, $I^-$ or $HSO_4^-$, in aqueous solution, optionally with the use of an organic solvent which is inert under the reaction conditions, using a nitrite. Diazotization is carried out with, for example, an alkali metal nitrite such as $NaNO_2$ (sodium nitrite) in amounts of 1.0-1.2 mol of nitrite, preferably 1.01-1.05 mol of nitrite, per mole of the compound of the formula (XIII). Suitable acids include mineral acids or strong organic acids, preference being given to hydrochloric acid or sulfuric acid. The solvent is water or a mixture of water with an organic solvent which is inert under the reaction conditions. The reaction temperature is generally between −5° C. and 50° C., preferably 10° C. to 20° C. (scheme 3).

The reaction of the resultant diazonium salts to give the aryl iodides of the formula (XIV) takes place in general without isolation and is carried out in the same aqueous or aqueous-organic solvent or solvent mixture as the diazotization. In the course of the reaction the diazonium group is replaced by the iodine atom, either by the anion of the diazonium salt (if in the acid $X^-$=$I^-$) or (if $X^-$ is not $I^-$) by reaction with added iodide, e.g., alkali metal iodide, preferably sodium iodide or potassium iodide. The amount of iodide here is for example 1.1 to 1.5 mol of iodide per mole of the compound of the formula (XIII) originally employed. The reaction temperature here runs in general to 10° C. to 40° C., preferably 15° C. to 30° C. (in this regard cf., e.g., DE 19625831 and Bioorg. Med. Chem. 2004, 12, 2079) (scheme 3).

Scheme 4

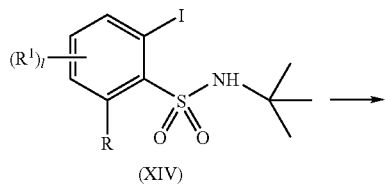

(XIV)

-continued

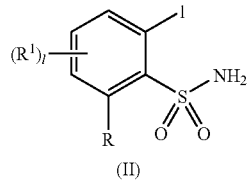

(II)

The elimination of the tert-butyl protective group in the compounds of the formula (XIV) to form the sulfonamides of the formula (II) is accomplished by, for example, treatment with a strong acid (see WO 89/10921). Examples of suitable strong acids include mineral acids, such as $H_2SO_4$ or HCl, or strong organic acids, such as trifluoroacetic acid. The reaction takes place at, for example, temperatures from −20° C. up to the respective reflux temperature of the reaction mixture, preferably at 0° C. to 40° C. The reaction can be carried out in bulk (without solvent) or else in an inert solvent, such as dichloromethane or trichloromethane (scheme 4).

Certain sulfonamides of the formula ((II) are known: 5-amino-2-iodobenzenesulfonamide [477932-67-5] (WO 2002098424); 2-iodo-4-methoxybenzenesulfonamide [342411-62-5] (Nippon Kagaku Kaishi 1978, (2), 259); (2E)-N-{2-[3-(aminosulfonyl)-4-iodophenyl]ethyl}-3-(2, 4-dimethoxyphenyl)acrylamide [308336-46-1] (DE 19923086); 5-(2-aminoethyl)-2-iodobenzenesulfonamide [308336-44-9] (DE 19923086); N-{2-[3-(aminosulfonyl)-4-iodophenyl]ethyl}-2,2,2-trifluoroacetamide [308336-43-8] (DE 19923086, DE 10054482, DE 10054481); 5-bromo-2-iodobenzenesulfonamide [273208-19-8]; 5-chloro-2-iodobenzenesulfonamide [273208-17-6]; 4-bromo-2-iodobenzenesulfonamide [273208-14-3]; 2-iodo-4-(trifluoromethyl)benzenesulfonamide [273208-12-1]; 2-iodo-4,5-dimethylbenzenesulfonamide [273208-09-6]; 4-chloro-2-iodobenzenesulfonamide [271796-28-2] (WO 2002003978, WO 2001660553); N-{2-[3-(aminosulfonyl)-4-iodophenyl]ethyl}-5-chloro-2-methoxybenzamide [254974-16-8](J. Med. Chem. 2001, 44-1085, DE 19832009); 2-iodo-5-methylbenzenesulfonamide [200060-22-6]; 2-amino-6-iodobenzenesulfonamide [153439-32-8](WO 9321171, WO 9321170); ethyl{[2-(aminosulfonyl)-3-iodophenyl]amino}(oxo)acetate [153439-30-6] (WO9321171); methyl 2-(aminosulfonyl)-3-iodobenzoate [144550-90-3] (WO 9213845); methyl 3-(aminosulfonyl)-4-iodobenzoate [144550-86-7] (WO 9213845); isopropyl 3-(aminosulfonyl)-2-iodobenzoate [144550-85-6] (WO 9213845); propyl 3-(aminosulfonyl)-2-iodobenzoate [144550-84-5] (WO 9213845); ethyl 3-(aminosulfonyl)-2-iodobenzoate [144550-81-2] (WO 9213845); methyl 3-(aminosulfonyl)-2-iodobenzoate [144550-75-4] (WO 9213845); N-[4-(aminosulfonyi)-2,3-diiodophenyl]acetamide [118427-12-6] (HU 44481); 4-amino-2,3-diiodobenzenesulfonamide [118427-08-0] (HU 44481); 4-amino-2,5-diiodobenzenesulfonamide [118427-07-9] (HU 44481); 4-amino-2,6-diiodobenzenesulfonamide [100377-04-6] (HU 44481); 2-iodo-3,5-dimethylbenzenesulfonamide [100377-04-6] (J. Chem. Soc., Abstr. 1956, 3668); 4-iodobenzene-1,3-disulfonamide [91425-72-8] (GB 93228); 4-amino-6-iodobenzene-1,3-disulfonamide [89891-29-2] (e.g., J. Pharm. Sci. 1997, 86, 631); 3-(aminosulfonyl)-4-iodobenzoic acid [82608-96-6] (FR 2493702, JP 57081411); 2-iodobenzenesulfonamide [53730-99-7] (e.g., WO 2002003978, EP 96002); 5-{[(1E)-(dimethylamino)methylene]amino}-2,4-diiodobenzenesulfonamide [22184-83-4] (Ces.-Slov. Farm. 1968, 17-272); 5-amino-2,4-diiodobenzenesulfonamide [22184-81-2] (Ces.-Slov. Farm. 1968, 17-272).

Certain sulfonyliso(thio)cyanates of the formula (IV) are known:
methyl 2-iodo-3-(isocyanatosulfonyl)benzoate [144550-98-1] (WO 9213845); ethyl 2-iodo-3-(isocyanatosulfonyl) benzoate [144550-93-6] (WO 9213845); propyl 2-iodo-3-(isocyanatosulfonyl)benzoate [144550-92-5] (WO 9213845); isopropyl 2-iodo-3-(isocyanatosulfonyl)benzoate [144550-91-4] (WO 9213845); methyl 3-iodo-2-(isocyanatosulfonyl)benzoate [144550-83-4] (WO 9213845).

Certain sulfonyl halides of the formula (VI) are known:
2,4-diiodobenzenesulfonyl chloride [686350-22-1] (Dok. Akad. Nauk SSR 1954, 99, 995); 3-(chlorosulfonyl)-4-iodobenzoic acid [402934-49-0] (Ind. J. Heterocycl. Chem. 2001, 11, 79; (R)-3-chloro-2-iodo-4-[(3,3,3-trifluoro-2-hydroxy-2-methylpropanoyl)amino]benzenesulfonyl chloride [329901-78-2] (WO 2001017956, WO 2001017955); methyl 3-(chlorosulfonyl)-2-iodobenzoate [144550-99-2] (WO 9213845); ethyl 3-(chlorosulfonyl)-2-iodobenzoate [144550-80-1] (WO 9213845); 5-(chlorosulfonyl)-2,4,6-triiodoisophthaloyl dichloride [135466-77-2](FR 2649698); 5-chloro-2-iodobenzenesulfonyl chloride [124866-38-2] (FR 2626000); 4-(acetylamino)-2,3-diiodobenzenesulfonyl chloride [118427-11-5] (HU 44481); 2-iodo-3,5-dimethylbenzenesulfonyl chloride [98545-86-9] (J. Chem. Soc. Abstr. 1956, 3668); 2-iodobenzenesulfonyl chloride [63059-29-0] (e.g., J. Med. Chem. 2005, 48, 353, EP 516392).

Certain tert-butylaminosulfonyl compounds of the formula (XIV) are known: N-(tert-butyl)-4-chloro-2-iodobenzenesulfonamide [271796-71-5]; N-(tert-butyl)-2-iodobenzenesulfonamide [146720-72-1] (EP 516392); methyl 3-[(tert-butylamino)sulfonyl]-2-iodobenzoate [144550-74-3] (WO 9213845).

Of the compounds of the formula (II), it is preferred to exclude those in which R is H and I is 1 or 2 and $R^1$ independently at each occurrence is one or more of the radicals $NH_2$, halogen, $CH_3$, $CF_3$, $CO_2H$, $CO_2(C_1$-$C_3)$alkyl, $SO_2NH_2$, $OCH_3$, $NHC(O)CH_3$, $N=CHN(CH_3)_2$, $(CH_2)_2NH_2$ or $(CH_2)_2NHC(O)CF_3$;
R is H and I is 0;
R is $NH_2$ and I is 0;
R is $NHC(O)CO_2CH_2CH_3$ and I is 0;
R is $CO_2CH_3$ and I is 0, and also the compounds (2E)-N-{2-[3-(aminosulfonyl)-4-iodophenyl]ethyl}-3-(2,4-dimethoxyphenyl)acrylamide and N-{2-[3-(aminosulfonyl)-4-iodophenyl]ethyl}-5-chloro-2-methoxybenzamide.

Of the compounds of the formula (IV) it is preferred to exclude those in which W is O or S and R is H, I is 1, and $R^1$ is $CO_2(C_1$-$C_3)$alkyl;
W is O or S and R is $CO_2(C_1$-$C_3)$alkyl, and I is 0.

Of the compounds of the formula (VI) it is preferred to exclude those in which Hal is Cl and R is H, I is 1 or 2, and $R^1$ independently at each occurrence is one or more halogen, $CH_3$, $CO_2H$, $CO_2(C_1$-$C_3)$alkyl or $NHC(O)CH_3$ radicals;
Hal is Cl and R is H, and I is 0, and also the compounds (R)-3-chloro-2-iodo-4-[(3,3,3-trifluoro-2-hydroxy-2-methylpropanoyl)amino]-benzenesulfonyl chloride and 5-chlorosulfonyl-2,4,6-triiodoisophthaloyl dichloride.

Of the compounds of the formula (XIV) it is preferred to exclude those in which R is H and I is 0 or 1 and $R^1$ is halogen or $CO_2(C_1$-$C_3)$alkyl.

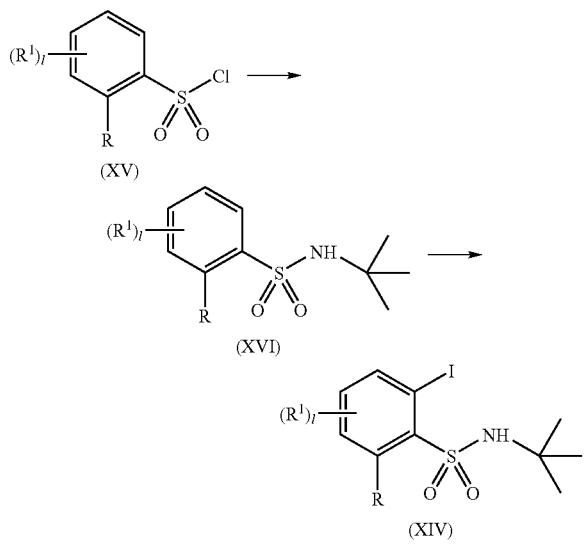

Substituted tert-butylaminosulfonyl compounds of the formula (XIV) can also be obtained by metalating compounds of the formula (XVI)—that is, replacing the hydrogen atom ortho to the $SO_2NH$-tert-butyl group in the compound of the formula (XVI) by a metal atom—said compounds (XIV) being obtainable by reacting commercially available sulfochlorides of the formula (XV) with tert-butylamine (see scheme 1) (sulfochlorides of the formula (XV) can also be prepared by diazotizing the corresponding amino compounds and subsequently sulfochlorinating the diazo products as indicated in scheme 1), the metallization being carried out using an organometallic compound, such as alkyl- or aryllithium, preferably n- or sec-butyllithium in hexane, optionally in the presence of a (further) inert diluent, such as tetrahydrofuran, and under an inert gas atmosphere, such as under argon or nitrogen, at temperatures between –70° C. and 20° C., and then, following metallization, reacting the product with iodine in the same reaction medium at temperatures between –100° C. and 40° C., preferably between –70° C. and 20° C., so as to replace the metal atom by iodine (scheme 5) (in this context see also: V. Snieckus et al., J. Org. Chem. 2001, 66, 3662 and Synlett 2000, (9), 1294).

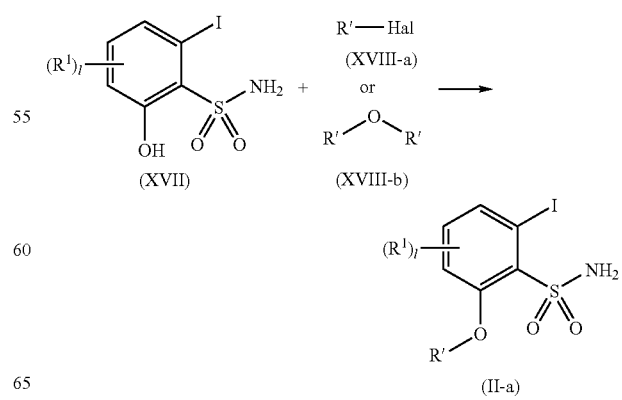

Specific sulfonamides of the formula (II-a) with R'=hydrocarbon radical such as alkyl, heterocyclyl radical, CO—$R^3$ or $S(O)_n$—$R^3$ can be prepared by reacting hydroxybenezenesulfonamides of the formula (XVII) with compounds of the formula (XVIII-a or XVIII-b), in which case one or more reaction auxiliaries may be used. In the compounds of the formula (XVIII-a) employed in this reaction the radical R' is for example a hydrocarbon radical such as alkyl, a heterocyclyl radical, CO—$R^3$ or $S(O)_n R^3$, and Hal is halogen, with alkyl, halogen, n and $R^3$ being as defined in formula (I). In the compounds of the formula (XVIII-b) R' may in particular be CO—$R^3$ or $S(O)_n R^3$. Examples of suitable reaction auxiliaries include the customary acidic acceptors such as organic or inorganic bases. These include, preferably, alkali metal compounds or alkaline earth metal compounds, such as the acetates, amides, carbonates, hydrogencarbonates, hydrides, hydroxides, or alkanoates of alkali metals or alkaline earth metals—mention may be made in particular here of potassium carbonate, cesium carbonate, lithium hydroxide, sodium hydroxide, and sodium ethoxide—and also basic organic nitrogen compounds, such as triethylamine, ethyldiisopropylamine, alkyl-substituted pyridines, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

Suitable solvents include not only water but also, in particular, inert organic solvents. These include, in particular, benzene, toluene, xylene, dichloromethane, chloroform, diethyl ether, dioxane, tetrahydrofuran, acetone, acetonitrile, N,N-dimethylformamide, N-methylpyrrolidone or ethyl acetate. The reaction temperatures range between 0° C. and the reflux temperature of the solvent used, preferably between 10° C. and 120° C. (scheme 6) (in this context cf. also WO 02/072560).

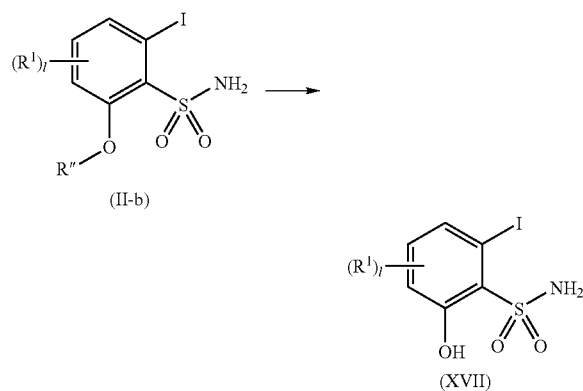

Hydroxybenzenesulfonamides of the formula (XVII) can be obtained, for example, from the ortho-alkoxy-substituted benzenesulfonamides of the formula (II-b) (obtainable, for example, by the reactions of schemes 1-6), it being possible for R" to be, in particular, ($C_1$-$C_4$)alkyl. For this purpose it is possible to treat the alkoxy compound of the formula (II-b) with a Lewis acid, preferably boron trihalides, such as $BBr_3$, in an inert solvent such as dichloromethane, dichloroethane or chloroform, preferably dichloromethane or dichloroethane. The reaction temperature is generally between –30° C. and the reflux temperature of the solvent, preferably from 0° C. to 40° C. (scheme 7) (see for example EP044807 and WO 97/03056).

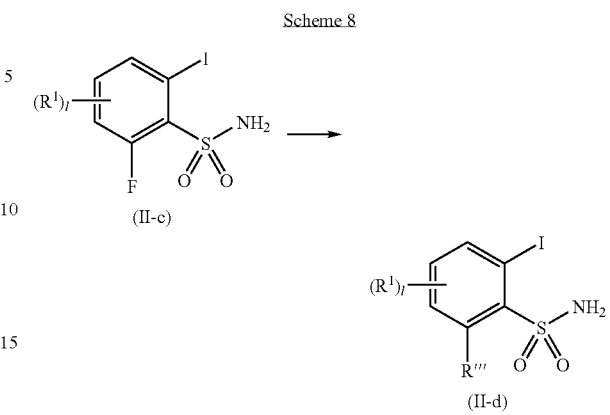

Benzenesulfonamides of the formula (II-d) can be obtained by exchanging the fluorine atom in the ortho-fluorobenzenesulfonamide of the formula (II-c) (obtainable, for example, by the reactions of schemes 1-6) by reaction with nuclophiles of the general formula R'''. R''' can be, in particular, alkyloxy, cycloalkoxy, alkenyloxy, alkynyloxy, aryloxy, heterocyclyloxy, alkylthio, alkenylthio, alkynylthio, arylthio, heterocyclylthio, N(alkyl)$_2$, NHalkyl, N(alkenyl)$_2$, NHalkenyl, N(alkynyl)$_2$, NHalkynyl, NHaryl, NHheterocyclyl or NH$_2$, it being possible for all said radicals (apart from the last one) to be substituted or unsubstituted. In the context of this reaction it is also possible for one or more reaction auxiliaries to be employed, such as the typical acid acceptors, such as organic or inorganic bases. These include, preferably, alkali metal compounds or alkaline earth metal compounds, such as acetates, amides, carbonates, hydrogencarbonates, hydrides, hydroxides, or alkanoates of alkali metals or alkaline earth metals—mention may be made in particular here of potassium carbonate, cesium carbonate, lithium hydroxide, sodium hydroxide, and sodium ethoxide, and especially sodium hydride—and also basic organic nitrogen compounds, such as triethylamine, ethyldiisopropylamine, alkyl-substituted pyridines, 1,4-diazabicyclo[2.2.2]octane (DABCO), 1,5-diazabicyclo[4.3.0]non-5-ene (DBN) or 1,8-diazabicyclo[5.4.0]undec-7-ene (DBU). Suitable solvents include not only water but also, in particular, inert organic solvents. These include, in particular, benzene, toluene, xylene, dichloromethane, chloroform, diethyl ether, dioxane, tetrahydrofuran, acetone, acetonitrile, N,N-dimethylformamide, N-methylpyrrolidone or ethyl acetate, among which particular emphasis may be given to diethyl ether, dioxane, and tetrahydrofuran. The reaction temperature is generally between –20° C. and the reflux temperature of the solvent used, in particular between 0° C. and the reflux temperature of the solvent used.

Besides the purely thermal conduct of the reaction, it is also possible to accelerate the reaction using microwave energy. For this purpose it is possible to use a commercially available microwave apparatus designed for chemical use. The reactions in this case are carried out in general at temperatures between 20° C. and 200° C., preferably between 40° C. and 170° C., and with an energy output of between 20 and 200 watts, preferably between 50 and 180 watts, for a reaction time of between 2 min and 60 min, preferably between 5 min and 45 min.

Benzenesulfonamides of the formula (II-d) with R'''=alkylthio, alkenylthio, alkynylthio, arylthio or heterocyclylthio can be converted into the corresponding sulfoxides or sulfones in analogy to reactions known from the literature, by treatment with oxidizing agent, preferably metachloroperbenzoic acid, hydrogen peroxide, sodium metaperiodate or Oxone (cf., e.g., "Reactions of Organosulfur Compounds"; Academic Press, New York, 1978, p. 16).

The (thio)carboxylic acid derivatives of the formula (III) used as starting materials in process a) of the invention for preparing compounds of the formula (I) are known and/or can be prepared by methods which are known per se (cf. EP 459244, EP 341489, EP 422469, EP 425948, EP 431291, EP 507171, EP 534266).

The sulfonyliso(thio)cyanates of the formula (IV) of the invention that are used in process b) of the invention for preparing compounds of the formula (I) can be prepared by methods known per se from the sulfonamides of the formula (II) of the invention (cf. DE 3208189, EP 23422, EP 64322, EP 44807, EP 216504). The aryl sulfonyliso(thio)cyanates are obtained with phosgene or thiophosgene, respectively, optionally in the presence of an alkyl isocyanate, such as butyl isocyanate, optionally in the presence of a reaction auxiliary, such as diazabicyclo[2.2.2]octane, and in the presence of a diluent, such as toluene, xylene or chlorobenzene, carrying out reaction at temperatures between 80° C. and 150° C. and following the reaction by distillative removal of the volatile components under reduced pressure.

The heterocyclyl compounds of the formula (V) used in processes b), c) and e) of the invention for preparing the compounds of the formula (I) are known and/or can be prepared by methods which are known per se (cf. EP 341489, EP 422469, EP 425948, EP 431291, EP 507171, EP 534266).

The sulfonyl halides of the formula (VI) used in processes c) and d) of the invention for preparing the compounds of the formula (I) can be prepared by a variety of methods known from the literature, such as i) oxidative chlorination of thioether (Recl. Trav. Chim. Pays-Bas 1982, 101, 91, ii) diazotization of aromatic amines with sodium nitrite in hydrochloric acid, followed by reaction of the resulting diazonium salt with sulfur dioxide and copper chloride (J. Org. Chem. 1960, 1824), iii) heteroatom-controlled lithiation, followed by sulfonylation (EP 73562; Org. React. 1979, 26, I), iv) Newman rearrangement and subsequent oxidative chlorination (U.S. Pat. No. 5,157,119), v) reaction of a sulfonamide of the formula (II) with thienyl chloride (Bull. Kor. Chem. Soc. 1994, 15, 323).

In one embodiment of process c) the reaction mixture obtained by reacting the sulfonyl halide (VI) with a (thio)cyanate is used directly for coupling with a heterocyclyl compound of the formula (V) for the synthesis of the compound of the formula (I) (in this context cf. WO 2003 091228 and U.S. Pat. No. 5,550,238).

The (thio)carbamides of the formula (VIII) for use in process d) of the invention for preparing the compounds of the formula (I) are known and/or can be prepared by methods which are known per se (cf. EP 45924).

The sulfonylamino(thio)carbonyl compounds of the formula (IX) used in process e) of the invention for preparing compounds of the formula (I) are prepared in analogy to reactions which are known per se (cf. EP 120 814). Alternatively the sulfonyliso(thio)cyanates of the formula (IV) can also be converted into the carbamates of the formula (IX) in a straightforward reaction in an inert solvent, preferably diethyl ether or dichloromethane, using phenol, for example.

The processes a), b), c), d) and e) of the invention for preparing the compounds of the formula (I) are preferably carried out using diluents. Suitable diluents in this context include, in particular, inert organic solvents, examples being aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene und o-dichlorobenzene, ethers such as diethyl ether and dibutyl ether, glycol dimethyl ether and diglycol dimethyl ether, tetrahydrofuran, and dioxane, ketones such as acetone, methyl ethyl ketone, methyl isopropyl ketone and methyl isobutyl ketone, esters such as methyl acetate and ethyl acetate, nitriles such as acetonitrile and propionitrile, amides, such as dimethylformamide, dimethylacetamide and N-methylpyrrolidone and also dimethyl sulfoxide, tetramethylene sulfone, and hexamethylphosphoramide.

Reaction auxiliaries which can be used for processes a), b), c), d) and e) of the invention include, for example, Lewis acids or acid acceptors which can be employed for reactions of this kind. Preferential suitability is possessed by acid acceptors, examples being alkali metal hydroxides, such as sodium hydroxide and potassium hydroxide, alkaline earth metal hydroxides, such as calcium hydroxide, alkali metal carbonates and alkali metal alkoxides, such as sodium carbonate and potassium carbonate, sodium tert-butoxide and potassium tert-butoxide and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo[4.3.0]non-5-ene (DBN), 1,8-diazabicyclo[5.4.0]-undec-7-en (DBU) and 1,4-diazabicyclo[2.2.2]octane (DABCO).

The reaction temperatures in processes a), b), c), d), and e) of the invention can be varied within a relatively wide range. It is usual to operate at temperatures between −20° C. and +150° C., preferably at temperatures between 0° C. and +100° C.

Processes a), b), c), d), and e) of the invention are generally carried out under atmospheric pressure. It is also possible, though, to operate under increased or reduced pressure.

Processes a), b), c), d), and e) of the invention are carried out using the respectively required starting materials in amounts which in general are approximately equimolar. It is also possible, though, to use one of the respectively employed components in a relatively large excess. The reactions are optionally carried out in a suitable diluent in the presence of a reaction auxiliary, such as an acid acceptor, and the reaction mixture is stirred at the respectively required temperature for a number of hours. Work up is accomplished, for processes a), b), c), d), and e) of the invention, by customary methods in each case (cf. the cited references).

The salts of the compounds of the formula (I) are prepared preferably in inert polar solvents, such as water, methanol or acetone, at temperatures from 0° C. to 100° C. Examples of suitable bases for preparing the salts of the invention are alkali metal carbonates, such as potassium carbonate, alkali metal hydroxides and alkaline earth metal hydroxides, such as NaOH or KOH, or alkali metal alkoxides, such as sodium methoxide or sodium tert-butoxide, or ammonia or ethanolamine.

The "inert solvents" identified in the above process versions refer in each case to solvents which are inert under the respective reaction conditions, but which need not necessarily be inert under any reaction conditions.

Collections of compounds of the formula (I) and/or salts thereof, which can be synthesized by the reactions identified above, can also be prepared parallelwise, in a manual, semi-automated or fully automated procedure. In this context it is possible, for example, to automate the implementation of the reaction, the workup or the purification of the products and/or intermediates. Overall this refers to a procedure as described for example by S. H. DeWitt in "Annual Reports in Combinatorial Chemistry and Molecular Diversity: Automated Synthesis", volume 1, Escom 1997, pages 69 to 77.

Microwave-assisted syntheses can be carried out using a microwave apparatus, one example being the "Discover" model from CEM GmbH Mikrowellen-Analysentechnik, Carl-Friedrich-Gauβ-Str. 9, 47475 Kamp-Linffort, DE.

For the parallelized reaction procedure and workup it is possible to use a range of commercially available instruments, of the kind offered by, for example, the companies Stem Corporation, Woodrolfe Road, Tollesbury, Essex, GB, H+P Labortechnik GmbH, Bruckmannring 28, 85764 Oberschleiβheim, DE, or Radleys, Shirehill, Saffron Walden, Essex, CB 11 3AZ, GB. For the parallelized purification of compounds of the formula (I) and salts thereof and/or of intermediates obtained in the course of the preparation, the apparatus available includes chromatography apparatus, such as that from ISCO, Inc., 4700 Superior Street, Lincoln, Nebr. 68504, US.

The apparatus recited result in a modular procedure, in which the individual worksteps are automated and yet manual operations have to be carried out between the worksteps. This can be overcome by using partly or fully integrated automation systems in which the respective automation modules are served, for example, by robots. Automation systems of this kind can be acquired from, for example, Zymark Corporation, Zymark Center, Hopkinton, Mass. 01748, US.

Besides the methods described here, the preparation of compounds of the formula (I) and salts thereof may take place entirely or partly by means of solid-phase-supported methods. For this purpose, individual intermediates or all intermediates in the synthesis, or in a synthesis adapted for the corresponding procedure, are bound to a synthetic resin. Solid-phase-supported synthesis methods are well described in the technical literature, e.g., Barry A. Bunin in "The Combinatorial Index", Academic Press, 1998.

The use of solid-phase-supported synthesis methods permits a range of protocols which are known from the literature and which in turn can be formed manually or automatively. For example it is possible to carry out partial automation of the "teabag" method (Houghten, U.S. Pat. No. 4,631,211; Houghten et al., Proc. Natl. Acad. Sci, 1985, 82, 5131-35) using products from IRORI, 11149 North Torrey Pines Road, La Jolla, Calif. 92037, US. Solid-phase-supported parallel syntheses are automated, for example, using apparatus from Argonaut Technologies, Inc., 887 Industrial Road, San Carlos, Calif. 94070, US or MultiSynTech GmbH, Wullener Feld 4, 58454 Witten, Del.

Preparation in accordance with the processes described here yields compounds of the formula (I) and salts thereof in the form of substance collections, referred to as libraries. The present invention additionally provides libraries comprising at least two compounds of the formula (I) and salts thereof.

The compounds of the formula (I) of the invention and/or salts thereof, referred to below collectively as "compounds of the invention", exhibit excellent herbicidal activity against a broad spectrum of economically important monocotyledonous and dicotyledonous weed plants. Even perennial weeds which produce shoots from rhizomes, rootstocks or other perennial organs, and which cannot easily be controlled, are effectively controlled by the active substances.

The present invention hence also provides a method of controlling unwanted plants or of regulating growth of plants, preferably in crops of plants, in which one or more compounds of the invention are applied to the plants (e.g., weed plants such as monocot or dicot weeds or unwanted crop plants), the seed (e.g., grains, seeds or vegetative propagation organs such as tubers or shoots with buds) or the area on which the plants are growing (e.g., the area under cultivation). The compounds of the invention can be applied, for example, before sowing, pre-emergence or post-emergence. Specific mention may be made, by way of example, of certain representatives of the monocot and dicot weed flora which can be controlled by the compounds of the invention, although the naming of specific species should not be taken to imply any restriction.

Among the monocot weed species those controlled effectively include, for example, *Apera spica venti*, *Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and also *Bromus* spp. such as *Bromus catharticus*, *Bromus secalinus*, *Bromus erectus*, *Bromus tectorum*, and *Bromus japonicus*, and *Cyperus* species from the annual group, and, among the perennial species, *Agropyron*, *Cynodon*, *Imperata*, and *Sorghum*, and also perennial *Cyperus* species.

In the case of dicot weed species, the spectrum of activity extends to species such as, for example, *Abutilon* spp., *Amaranthus* spp., *Chenopodium* spp., *Chrysanthemum* spp., *Galium* spp. such as *Galium aparine*, *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp., and *Viola* spp., *Xanthium* spp., among the annuals, and also *Convolvulus*, *Cirsium*, *Rumex* and *Artemisia* among the perennial weeds.

Weed plants which occur in rice under the specific culture conditions, such as *Echinochloa*, *Sagittaria*, *Alisma*, *Eleocharis*, *Scirpus* and *Cyperus*, are likewise controlled to outstanding effect by the active substances of the invention.

If the compounds of the invention are applied to the soil surface prior to germination, then either emergence of the weed seedlings is prevented completely, or the weeds grow until they have reached the cotyledon stage, but their growth then comes to a standstill and, after three or four weeks have elapsed, they die off completely.

When the active substances are applied post-emergence to the green parts of plants there is likewise a drastic arrest in growth very soon after the treatment, and the weed plants remain at the growth stage they were in at the time of application, or die off completely after a certain time, so that in this way competition by the weeds, which is detrimental to the crop plants, is eliminated at a very early stage and in a sustained manner.

Although the compounds of the invention exhibit excellent herbicidal activity with respect to monocot or dicot weeds, crop plants of economic importance, examples being dicotyledonous crops such as soybean, cotton, oilseed rape, sugarbeet, or gramineous crops such as wheat, barley, rye, maize or rice, especially maize and wheat, are damaged either not at all or insignificantly. For these reasons, the present compounds possess excellent suitability for selectively controlling unwanted plant growth in plant crops such as agricultural stands of useful plants or stands of ornamentals.

Furthermore, the compounds of the invention exhibit outstanding growth-regulatory properties in respect of crop plants. They exert regulatory intervention in the plants' own metabolism and can therefore be employed to exert a controlled influence on plant constituents and to facilitate harvesting, such as by initiating desiccation and stunting of growth, for example. They are also suitable, moreover, for the general control and inhibition of unwanted vegetative growth, without killing off the plants. Inhibition of vegetative growth plays an important part in numerous monocot and dicot crops, since it allows their susceptibility to lodging to be reduced or prevented completely.

On the basis of their herbicidal and plant growth-regulatory properties, the active substances can also be used for controlling weed plants in crops of genetically modified plants which are known or are yet to be developed. As a rule, the transgenic plants are distinguished by particular advantageous properties, such as by resistances to certain pesticides, especially certain herbicides, resistances to plant diseases or causative organisms of plant diseases, such as certain insects or microorganisms, for instance fungi, bacteria or viruses. Other particular properties relate for example to the harvested material, in terms of quantity, quality, storage properties, composition, and specific constituents. For instance, transgenic plants are known which feature increased starch content or modified quality of starch, or whose fatty acid composition in the harvested material is different.

The compounds of the invention are employed preferably in economically important transgenic crops of useful plants and ornamentals, such as of cereals such as wheat, barley, rye, oats, millet, rice, cassaya, and maize, or else crops of sugarbeet, cotton, soybean, oilseed rape, potato, tomato, pea, and other vegetables. The compounds of the invention can be used with preference as herbicides in crops of useful plants which are resistant or have been made genetically resistant to the phytotoxic effects of the herbicides.

Conventional routes to the generation of new plants which have modified properties as compared with existing plants include, for example, the traditional breeding methods and the production of mutants. Alternatively, novel plants with modified properties can be generated with the aid of recombinant methods (see, for example, EP-A-0221044 and EP-A-0131624). Descriptions have been given, for example, in a number of cases, of:

genetic modifications of crop plants for the purpose of modifying the starch synthesized in the plants (e.g., WO 92/11376, WO 92/14827 and WO 91/19806);

transgenic crop plants which are resistant to certain herbicides of the glufosinate type (cf., e.g., EP-A-0242236, EP-A-242246) or glyphosate type (WO 92/00377) or of the sulfonylurea type (EP-A-0257993, U.S. Pat. No. 5,013,659);

transgenic crop plants, cotton for example, with the ability to produce *Bacillus thuringiensis* toxins (Bt toxins), which make the plants resistant to certain pests (EP-A-0142924 and EP-A-0193259); and transgenic crop plants with modified fatty acid composition (WO 91/13972).

Numerous techniques of molecular biology which allow new transgenic plants having modified properties to be generated are known in principle (see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone", VCH Weinheim, 2nd edition, 1996; or Christou, Trends in Plant Science 1 (1996) 423-31).

For genetic manipulations of this kind it is possible to introduce nucleic acid molecules into plasmids that permit mutagenesis or a sequence alteration by recombination of DNA sequences. With the aid of the abovementioned standard techniques it is possible, for example, to carry out base substitutions, to remove part-sequences or to add natural or synthetic sequences. The fragments can be provided with adapters or linkers to link the DNA fragments to one another.

Plant cells featuring reduced activity of a gene product can be produced, for example, by expressing at least one corresponding antisense RNA, a sense RNA for achieving a cosuppression effect, or expressing at least one appropriately constructed ribozyme which specifically cleaves transcripts of the above-mentioned gene product.

For this purpose it is possible on the one hand to use DNA molecules which encompass the entire coding sequence of a gene product, including any flanking sequences that may be present, and also DNA molecules which encompass only parts of the coding sequence, in which case these parts must be long enough to produce an antisense effect in the cells. A further possibility is the use of DNA sequences which have a high degree of homology with the coding sequences of a gene product and yet are not entirely identical.

In the context of expressing nucleic acid molecules in plants, the synthesized protein may be localized in any desired compartment of the plant cell. However, in order to achieve localization in one particular compartment, the coding region can be linked, for example, to DNA sequences which ensure localization in one particular compartment. Sequences of this kind are known to the skilled worker (see, for example, Braun et al., EMBO J. 11 (1992), 3219-27; Wolter et al., Proc. Natl. Acad. Sci. USA 85 (1988), 846-50; Sonnewald et al., Plant J. 1 (1991), 95-106).

The transgenic plant cells can be regenerated by known techniques to form whole plants. In principle, the transgenic plants can be plants of any desired plant species, i.e., both monocotyledonous and dicotyledonous plants.

Thus it is possible to obtain transgenic plants which exhibit modified properties through overexpression, suppression or inhibition of homologous (i.e., natural) genes or gene sequences, or expression of heterologous (i.e., foreign) genes or gene sequences.

The compounds of the invention can be used with preference in transgenic crops which are resistant to herbicides from the group of sulfonylaminocarbonyl compounds, sulfonylureas, glufosinate-ammonium or glyphosate-isopropylammonium, and analogous active substances.

When the compounds of the invention are employed in transgenic crops, effects are frequently apparent—in addition to the effects on weed plants that are observed in other crops—that are specific to application in the particular transgenic crop: for example, a modified or specifically widened controllable weed spectrum, modified application rates which can be used for application, preferably effective capacity for combination with the herbicides to which the transgenic crop is resistant, and influencing of growth and yield of the transgenic crop plants.

The invention hence also provides for the use of the compounds of the invention as herbicides for controlling weed plants in transgenic and nontransgenic plant crops.

The compounds of the invention can be employed in the form of wettable powders, emulsifiable concentrates, sprayable solutions, dusts or granules in the customary preparations. The invention therefore also provides herbicidal and plant growth regulating compositions which comprise the compounds of the invention.

The compounds of the invention can be formulated in a variety of ways as a function of the prevailing biological and/or chemicophysical parameters. Examples of suitable formulation options include the following: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules, and waxes. These individual types of formulation are known in principle and are described in, for example, Winnacker-Küchler, "Chemische Technologie", volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents, and further adjuvants, are likewise known and are described in, for example, the following: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N. Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N. Y. 1964; Schönfeldt, "Grenzflächenaktive Äthylenoxidaddukte", Wiss. Verlagsgesell., Stuttgart 1976; Winnacker-Küchler, "Chemische Technologie", volume 7, C. Hanser Verlag Munich, 4th ed. 1986.

On the basis of these formulations it is also possible to produce combinations with other pesticidal substances, such as insecticides, acaricides, herbicides, and fungicides, and also with safeners, fertilizers and/or growth regulators, in the form, for example, of a ready-to-use formulation, or as a tank mix.

Wettable powders are products which can be dispersed uniformly in water and which also include, besides the active substance, and in addition to a diluent or inert substance, ionic and/or nonionic surfactants (wetting agents, dispersants), examples being polyoxyethylated alkylphenols, polyoxethylated fatty alcohols, polyoxethylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurate. To prepare the wettable powders, the active herbicidal substances, for example, are finely ground in customary apparatus such as hammer mills, blower mills, and air-jet mills, and are simultaneously or subsequently mixed with the formation auxiliaries.

Emulsifiable concentrates are prepared by dissolving the active substance in an organic solvent, such as butanol, cyclohexanone, dimethylformamide, xylene or else higher-boiling aromatics or hydrocarbons, or mixtures of the organic solvents with addition of one or more ionic and/or nonionic surfactants (emulsifiers). Examples of emulsifiers which can be used include the following: calcium alkylarylsulfonate salts such as Ca dodecylbenzenesulfonate, or nonionic emulsifiers such as fatty acid polyglycol esters, alkylaryl polyglyol ethers, fatty alcohol polyglycol ethers, propylene oxide ethylene oxide-condensates, alkyl polyethers, sorbitan esters such as sorbitan fatty acid esters or polyoxyethylene sorbitan esters, such as polyoxyethylene sorbitan fatty acid esters.

Dusts are obtained by grinding the active substance with finely divided solid materials, such as talc, natural clays, such as kaolin, bentonite, and pyrophyllite, or diatomaceous earth.

Suspension concentrates can be water-based or oil-based. One example of their possible preparation is by wet grinding using commercially customary bead mills, where appropriate with addition of surfactants, as have already been recited above in connection with the other types of formulation, for example.

Emulsions, such as oil-in-water emulsions (EW), for example, can be prepared for example by means of stirrers, colloid mills and/or static mixers, using aqueous organic solvents and, where appropriate, surfactants as have already been recited above in relation to the other types of formulation.

Granules can be produced either by spraying the active substance through nozzles onto adsorptive, granulated inert material or by applying active substance concentrates to the surface of carriers such as sand, kaolinites or else granulated inert material with the aid of tackifiers, such as polyvinyl alcohol, sodium polyacrylate or else mineral oils. Suitable active substances can also be granulated in the way which is conventional for the production of fertilizer granules, and if desired as a mixture with fertilizers.

Water-dispersible granules are produced generally by the customary methods such as spray drying, fluidized-bed granulation, disk granulation, mixing with high-speed mixers, and extrusion without solid inert material.

To produce disk granules, fluidized-bed granules, extruder granules, and spray granules, see, for example, methods in "Spray-Drying Handbook", 3rd ed., 1979, G. Goodwin Ltd., London; J. E. Browning, "Agglomeration", Chemical and Engineering 1967, pages 147 ff; "Perry's Chemical Engineer's Handbook", 5th ed., McGraw-Hill, New York 1973, p. 8-57.

For further details on the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical preparations contain in general 0.1 to 99% by weight, in particular 0.1 to 95% by weight, of compounds of the invention. In wettable powders the active substance concentration is for example about 10% to 90% by weight, the remainder to 100% by weight being composed of typical formation ingredients. In the case of emulsifiable concentrates the active substance concentration can be about 1% to 90%, preferably 5% to 80% by weight. Dust formulations contain 1% to 30% by weight of active substance, preferably mostly 5% to 20% by weight of active substance; sprayable solutions contain about 0.05% to 80%, preferably 2% to 50% by weight of active substance. In the case of water-dispersible granules the active substance content depends partly on whether the active compound is in solid or in liquid form and on what granulating assistants, fillers, etc. are used. For the water-dispersible granules, the active substance content is for example between 1% and 95% by weight, preferably between 10% and 80% by weight.

In addition, the stated active substance formulations comprise, where appropriate, the stickers, wetters, dispersants, emulsifiers, penetrants, preservatives, frost preventives, solvents, fillers, carriers, colorants, defoamers, antievaporants, pH modifiers, and viscosity modifiers that are customary in each case.

Candidate co-components for the compounds of the invention in mixture formulations or in a tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, by Weed Research 26 (1986) 441-45 or "The Pesticide Manual", 13th edition, The British Crop Protection Council and the Royal Soc. of Chemistry, 2003, and references cited therein. Examples of known herbicides which can be combined with the compounds of the invention include the following active substances (note: the compounds are designated either by their "common name" in accordance with the International Organization for Standardization (ISO) or by the chemical name, together where appropriate with a customary code number), which in each case include all use forms, such as acids, salts, esters, and isomers such as stereoisomers and optical isomers. The citation given is of one use form and in some cases of two or more use forms:

2,4-D, acetochlor, acifluorfen, acifluorfen-sodium, aclonifen, alachlor, alloxydim, alloxydim-sodium, ametryn, amicarbazone, amidosulfuron, aminopyralid, amitrole, anilofos, asulam, atrazine, azafenidin, azimsulfuron, beflubutamid, benazolin, benazolin-ethyl, benfuresate, bensulfuron-methyl, bentazone, benzfendizone, benzobicyclon, benzofenap, bifenox, bilanafos, bispyribac-sodium, bromacil, bromobutide, bromofenoxim, bromoxynil, butachlor, butafenacil, butenachlor, butralin, butroxydim, butylate, cafenstrole, carbetamide, carfentrazone-ethyl, chlomethoxyfen, chloridazon, chlorimuron-ethyl, chlornitrofen, chlorotoluron, chlorsulfuron, cinidon-ethyl, cinmethylin, cinosulfuron, clefoxydim, clethodim, clodinafop-propargyl, clomazone, clomeprop, clopyralid, cloransulam-methyl, cumyluron, cyanazine, cyclosulfamuron, cycloxydim, cyhalofop-butyl, desmedipham, dicamba, dichlobenil, dichlorprop, dichlorprop-P, diclofop-methyl, diclosulam, difenzoquat, diflufenican, diflufenzopyr, dikegulac-sodium, dimefuron, dimepiperate, dimethachlor, dimethametryn, dimethenamid, triaziflam, diquat-dibromide, dithiopyr, diuron, dymron, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, flamprop-M-isopropyl, flamprop-M-methyl, flazasulfuron, florasulam, fluazifop, fluazifop-butyl, fluazifop-butyl, fluazolate, flucarbazone-sodium, flucetosulfuron, fluchloralin, flufenacet, flufenpyr, flumetsulam, flumiclorac-pentyl, flumioxazin, fluometuron, fluorochloridone, fluoroglycofen-ethyl; flupoxam, flupyrsulfuron-methyl-sodium, fluridone, fluroxypyr, fluroxypyr-butoxypropyl, fluroxypyr-meptyl, flurprimidol, flurtamone, fluthiacet-methyl, fomesafen, foramsulfuron, glufosinate, glufosinate-ammonium, glyphosate, halosulfuron-methyl, haloxyfop, haloxyfop-ethoxyethyl, haloxyfop-methyl, haloxyfop-P-methyl, hexazinone, imazamethabenz-methyl, imazamox, imazapic, imazapyr, imazaquin, imazethapyr, imazosulfuron, indanofan, iodosulfuron-methyl-sodium, ioxynil, isoproturon, isouron, isoxaben, isoxachlortole, isoxaflutole, ketospiradox, lactofen, lenacil, linuron, MCPA, mecoprop, mecoprop-P, mefenacet, mesosulfuron-methyl, mesotrione, metamifop, metamitron, metazachlor, methabenzthiazuron, methyldymron, metobromuron, metolachlor, metosulam, metoxuron, metribuzin, metsulfuron-methyl, molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxsulam, pentoxazone, pethoxamid, phenmedipham, picloram, picolinafen, pinoxaden, piperophos, pretilachlor, primisulfuron-methyl, profluazol, profoxydim, prometryn, propachlor, propanil, propaquizafop, propisochlor, propoxycarbazone-sodium, propyzamide, prosulfocarb, prosulfuron, pyraclonil, pyraflufen-ethyl, pyrazolate, pyrazosulfuron-ethyl, pyrazoxyfen, pyribenzoxim, pyributicarb, pyridafol, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sethoxydim, simazine, simetryn, S-metolachlor, sulcotrione, sulfentrazone, sulfometuron-methyl, sulfosate, sulfosulfuron, tebuthiuron, tepraloxydim, terbuthylazine, terbutryn, thenylchlor, thiazopyr, thifensulfuron-methyl, thiobencarb, tiocarbazil, tralkoxydim, triallate, triasulfuron, tribenuron-methyl, triclopyr, tridiphane, trifloxysulfuron, trifluralin, triflusulfuron-methyl, and tritosulfuron.

The compounds of the invention can also be used in combination with one or more compounds which act as safeners. Examples of safeners include the following compounds:

a) Compounds of formulae (XIX) to (XXI),

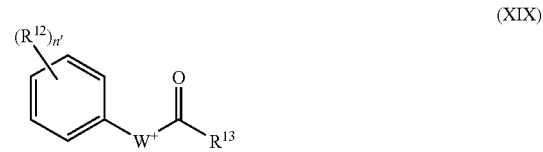

(XIX)

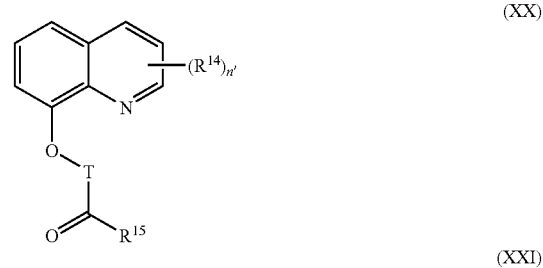

(XX)

(XXI)

where the symbols and indices have the following definitions:

n' is a natural number from 0 to 5, preferably 0 to 3;

T is a ($C_1$ or $C_2$)alkanediyl chain which is unsubstituted or substituted by one or two ($C_1$-$C_4$)alkyl radicals or by [($C_1$-$C_3$)alkoxy]carbonyl;

W$^+$ is an unsubstituted or substituted divalent heterocyclic radical from the group of partly unsaturated or aromatic five-membered-ring heterocycles having 1 to 3 ring heteroatoms of N or O type, including at least one nitrogen atom and not more than one oxygen atom in the ring, preferably a radical from the group (W$^+$1) to (W$^+$4),

W$^+$1

W$^+$2

W$^+$3

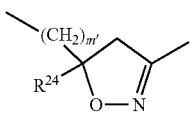

m' is 0 or 1;

$R^{12}$ and $R^{14}$ are identical or different and are hydrogen, halogen, $(C_1-C_4)$alkyl, $(C_1-C_4)$alkoxy, nitro or $(C_1-C_4)$haloalkyl;

$R^{13}$ and $R^{15}$ are identical or different and are $OR^{19}$, $SR^{19}$ or $NR^{19}R^{20}$ or are a saturated or unsaturated 3- to 7-membered heterocycle having at least one nitrogen atom and up to 3 heteroatoms, preferably from the group of O and S, which is attached via the nitrogen atom to the carbonyl group in (XIX) or (XX) and is unsubstituted or substituted by radicals from the group consisting of $(C_1-C_4)$alkyl, $(C_1-C_4)$alkoxy or optionally substituted phenyl, and are preferably a radical of the formula $OR^{19}$, $NHR^{20}$ or $N(CH_3)_2$, particularly of the formula $OR^{19}$;

$R^{19}$ is hydrogen or an unsubstituted or substituted aliphatic hydrocarbon radical, preferably with a total of 1 to 18 carbon atoms;

$R^{20}$ is hydrogen, $(C_1-C_6)$alkyl, $(C_1-C_6)$alkoxy or substituted or unsubstituted phenyl;

$R^{21}$ is hydrogen, $(C_1-C_8)$alkyl, $(C_1-C_8)$haloalkyl, $(C_1-C_4)$alkoxy-$(C_1-C_4)$alkyl, $(C_1-C_4)$hydroxyalkyl, $(C_3-C_{12})$cycloalkyl or tri-$(C_1-C_4)$alkylsilyl;

$R^{22}$, $R^{23}$ and $R^{24}$ are identical or different and are hydrogen, $(C_1-C_8)$alkyl, $(C_1-C_8)$haloalkyl, $(C_3-C_{12})$cycloalkyl or substituted or unsubstituted phenyl;

$R^{16}$ is $(C_1-C_4)$alkyl, $(C_1-C_4)$haloalkyl, $(C_1-C_4)$alkenyl, $(C_2-C_4)$haloalkenyl, $(C_3-C_7)$cycloalkyl, preferably dichloromethyl;

$R^{17}$ and $R^{18}$ are each identical or different and are hydrogen, $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_1-C_4)$alkylcarbamoyl-$(C_1-C_4)$alkyl, $(C_2-C_4)$alkenylcarbamoyl-$(C_1-C_4)$alkyl, $(C_1-C_4)$alkoxy-$(C_1-C_4)$alkyl, dioxolanyl-$(C_1-C_4)$alkyl, thiazolyl, furyl, furylalkyl, thienyl, piperidyl, substituted or unsubstituted phenyl, or $R^{12}$ and $R^{13}$ together form a substituted or unsubstituted heterocyclic ring, preferably an oxazolidine, thiazolidine, piperidine, morpholine, dihydropyrimidine or benzoxazine ring; or b) one or more compounds from the following group:
  1,8-naphthalic anhydride,
  methyl diphenylmethoxyacetate,
  cyanomethoxyimino(phenyl)acetonitrile (cyometrinil),
  1,3-dioxolane-2-ylmethoxyimino(phenyl)acetonitrile (oxabetrinil),
  4'-chloro-2,2,2-trifluoroacetophenone O-1,3-dioxolan-2-ylmethyloxime (fluxofenim),
  4,6-dichloro-2-phenylpyrimidine (fenclorim),
  benzyl 2-chloro-4-trifluoromethyl-1,3-thiazole-5-carboxylate (flurazole),
  2-dichloromethyl-2-methyl-1,3-dioxolan (MG-191),
  N-(4-methylphenyl)-N'-(1-methyl-1-phenylethyl)urea (dymron),
  1-[4-(N-2-methoxybenzoylsulfamoyl)phenyl]-3-methylurea,
  1-[4-(N-2-methoxybenzoylsulfamoyl)phenyl]-3,3-dimethylurea,
  1-[4-(N-4,5-dimethylbenzoylsulfamoyl)phenyl]-3-methylurea,
  1-[4-(N-naphthoylsulfamoyl)phenyl]-3,3-dimethylurea,
  (2,4-dichlorophenoxy)acetic acid (2,4-D),
  (4-chlorophenoxy)acetic acid,
  (R,S)-2-(4-chloro-o-tolyloxy)propionic acid (mecoprop),
  4-(2,4-dichlorophenoxy)butyric acid (2,4-DB),
  (4-chloro-o-tolyloxy)acetic acid (MCPA),
  4-(4-Chloro-o-tolyloxy)butyric acid,
  4-(4-chlorophenoxy)butyric acid,
  3,6-dichloro-2-methoxybenzoic acid (dicamba),
  1-(ethoxycarbonyl)ethyl 3,6-dichloro-2-methoxybenzoate (lactidichlor),
  and also salts and esters thereor, preferably $(C_1-C_8)$ esters;

c) N-acylsulfonamides of the formula (XXII) and salts thereof,

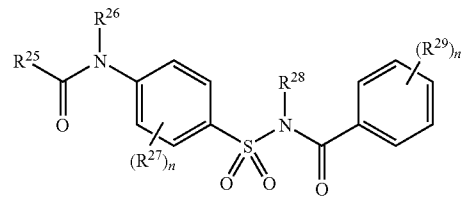

in which $R^{25}$ is hydrogen, a hydrocarbon radical, a hydrocarbonoxy radical, a hydrocarbonthio radical or a heterocyclyl radical, each of the last-mentioned four radicals being unsubstituted or substituted by one or more identical or different radicals from the group consisting of halogen, cyano, nitro, amino, hydroxy, carboxyl, formyl, carbonamide, sulfonamide, and radicals of the formula —$Z^a$—$R^a$,
  each hydrocarbon moiety having preferably 1 to 20 carbon atoms, and a carbon-containing radical $R^{25}$, inclusive of substituents, having preferably 1 to 30 carbon atoms;

$R^{26}$ is hydrogen or $(C_1-C_4)$alkyl, preferably hydrogen, or $R^{25}$ and $R^{26}$ together with the group of the formula —CO—N— are the radical of a 3- to 8-membered saturated or unsaturated ring;

$R^{27}$ is identical or different at each occurrence and is halogen, cyano, nitro, amino, hydroxy, carboxyl, formyl, $CONH_2$, $SO_2NH_2$ or a radical of the formula —$Z^b$—$R^b$;

$R^{28}$ is hydrogen or $(C_1-C_4)$alkyl, preferably H;

$R^{29}$ is identical or different at each occurrence and is halogen, cyano, nitro, amino, hydroxy, carboxyl, CHO, $CONH_2$, $SO_2NH_2$ or a radical of the formula —$Z^c$—$R^c$;

$R^a$ is a hydrocarbon radical or a heterocyclyl radical, each of the two last-mentioned radicals being unsubstituted or substituted by one or more identical or different radicals from the group consisting of halogen, cyano, nitro, amino, hydroxy, and mono- and di-[$(C_1-C_4)$alkyl]amino, or is an alkyl radical in which 2 or more, preferably 2 or 3, nonadjacent $CH_2$ groups are each replaced by an oxygen atom;

$R^b$ and $R^c$ are identical or different and are each a hydrocarbon radical or a heterocyclyl radical, each of the two last-mentioned radicals being unsubstituted or substituted by one or more identical or different radicals from the group consisting of halogen, cyano, nitro, amino, hydroxy, phosphoryl, halo-$(C_1-C_4)$alkoxy, and mono- and di-[$(C_1-C_4)$alkyl]amino, or are each an alkyl radical in which 2 or more, preferably 2 or 3, nonadjacent $CH_2$ groups are each replaced by an oxygen atom;

$Z^a$ is a divalent group of the formula —O—, —S—, —CO—, —CS—, —CO—O—, —CO—S—, —O—CO—, —S—CO—, —SO—, —SO$_2$—, —NR$^+$—, —CO—NR$^+$—, —NR$^+$—CO—, —SO$_2$—NR$^+$— or —NR$^+$—SO$_2$—, the bond indicated on the right in the respective divalent group, being the bond to the radical $R^a$, and the $R^+$ in the last-mentioned 5 radicals each being, independently of one another, H, (C$_1$-C$_4$)alkyl or halo-(C$_1$-C$_4$)-alkyl;

$Z^b$ and $Z^c$ independently of one another are each a direct bond or a divalent group of the formula —O—, —S—, —CO—, —CS—, —CO—O—, —CO—S—, —O—CO—, —S—CO—, —SO—, —SO$_2$—NR$^+$—, —SO$_2$—NR$^+$—, —NR$^+$—SO$_2$—, —CO—NR$^+$— or —NR$^+$—CO—, the bond indicated on the right in the respective divalent group being the bond to the radical $R^b$ or $R^c$, respectively, and the $R^+$ in the last-mentioned 5 radicals each being, independently of one another, H, (C$_1$-C$_4$)alkyl or halo-(C$_1$-C$_4$)alkyl;

n is an integer from 0 to 4, preferably 0, 1 or 2, particularly 0 or 1, and m is an integer from 0 to 5, preferably 0, 1, 2 or 3, particularly 0, 1 or 2;

d) acylsulfamoylbenzamides of the formula (XXIII), where appropriate also in salt form,

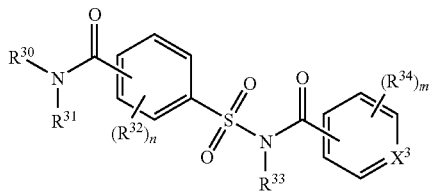

(XXIII)

in which $X^3$ is CH or N;

$R^{30}$ is hydrogen, heterocyclyl or a hydrocarbon radical, the two last-mentioned radicals being optionally substituted by one or more, identical or different radicals from the group consisting of halogen, cyano, nitro, amino, hydroxy, carboxyl, CHO, CONH$_2$, SO$_2$NH$_2$ and $Z^a$—$R^a$;

$R^{31}$ is hydrogen, hydroxy, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, the five last-mentioned radicals being optionally substituted by one or more, identical or different radicals from the group consisting of halogen, hydroxy, (C$_1$-C$_4$)alkyl, (C$_1$-C$_4$)alkoxy, and (C$_1$-C$_4$)alkylthio, or $R^{30}$ and $R^{31}$ together with the nitrogen atom which carries them are a 3- to 8-membered saturated or unsaturated ring;

$R^{32}$ is halogen, cyano, nitro, amino, hydroxy, carboxyl, CHO, CONH$_2$, SO$_2$NH$_2$ or $Z^b$—$R^b$;

$R^{33}$ is hydrogen, (C$_1$-C$_4$)alkyl, (C$_2$-C$_4$)alkenyl or (C$_2$-C$_4$)alkynyl;

$R^{34}$ is halogen, cyano, nitro, amino, hydroxy, carboxyl, phosphoryl, CHO, CONH$_2$, SO$_2$NH$_2$ or $Z^c$—$R^c$;

$R^a$ is a (C$_2$-C$_{20}$)alkyl radical whose carbon chain is interrupted one or more times by oxygen atoms, or is heterocyclyl or a hydrocarbon radical, the two last-mentioned radicals being optionally substituted by one or more, identical or different radicals from the group consisting of halogen, cyano, nitro, amino, hydroxy, and mono- and di-[(C$_1$-C$_4$)alkyl]amino;

$R^b$ and $R^c$ are identical or different and are each a (C$_2$-C$_{20}$) alkyl radical whose carbon chain is interrupted one or more times by oxygen atoms, or are heterocyclyl or a hydrocarbon radical, the two last-mentioned radicals being optionally substituted by one or more, identical or different radicals from the group consisting of halogen, cyano, nitro, amino, hydroxy, phosphoryl, (C$_1$-C$_4$)-haloalkoxy, and mono- and di-[(C$_1$-C$_4$)alkyl]amino;

$Z^a$ is a divalent unit from the group O, S, CO, CS, C(O)O, C(O)S, SO, SO$_2$, NR$^d$, C(O)NR$^d$ or SO$_2$NR$^d$;

$Z^b$ and $Z^c$ are identical or different and are each a direct bond or a divalent unit from the group O, S, CO, CS, C(O)O, C(O)S, SO, SO$_2$, NR$^d$, SO$_2$, NR$^d$ or C(O)NR$^d$;

$R^d$ is hydrogen, (C$_1$-C$_4$)alkyl or (C$_1$-C$_4$)haloalkyl;

n is an integer from 0 to 4, and m, if X is CH, is an integer from 0 to 5 and, if X is N, is an integer from 0 to 4;

e) Compounds of formula (XXIV),

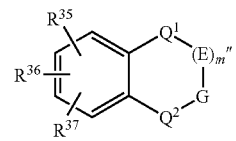

(XXIV)

in which the symbols and indices have the following definitions:

$R^{35}$ is H, (C$_1$-C$_4$)alkyl, (C$_1$-C$_4$)alkyl substituted by (C$_1$-C$_4$)alkyl-X$^4$ or (C$_1$-C$_4$)haloalkyl-X$^4$, (C$_1$-C$_4$)haloalkyl, NO$_2$, CN, —COO—R$^{38}$, NR$_2^{39}$, SO$_2$NR$_2^{40}$ or CONR$_2^{41}$;

$R^{36}$ is H, halogen, (C$_1$-C$_4$)alkyl, CF$_3$, (C$_1$-C$_4$)alkoxy or (C$_1$-C$_4$)haloalkoxy;

$R^{37}$ is H, halogen or (C$_1$-C$_4$)alkyl;

$Q^1$ and $Q^2$, E and G are identical or different and are —O—, —S—, —CR$_2^{42}$—, —CO—, NR$^{43}$— or a group of formula (XXV),

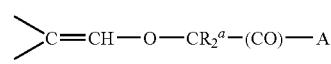

(XXV)

with the provisos that a) at least one of groups $Q^1$, $Q^2$, E, and G is a carbonyl group, that exactly one of these groups is a radical of the formula (XXV), and that the group of formula (XXV) is adjacent to a carbonyl group, and b) two adjacent groups $Q^1$, $Q^2$, E, and G cannot simultaneously be oxygen;

$R^a$ is identical or different at each occurrence and is H or (C$_1$-C$_8$)alkyl, or the two radicals $R^a$ together are (C$_2$-C$_6$) alkylene;

A is R$^b$—Y$^3$— or —NR$_2^{44}$;

X$^4$ is —O— or —S(O)$_p$—;

Y$^3$ is —O— or —S—;

$R^b$ is H, (C$_1$-C$_8$)alkyl, (C$_1$-C$_8$)haloalkyl, (C$_1$-C$_4$)alkoxy-(C$_1$-C$_8$)alkyl, (C$_3$-C$_6$)alkenyloxy-(C$_1$-C$_8$)alkyl, or phenyl-(C$_1$-C$_8$)alkyl, the phenyl ring being optionally substituted by halogen, (C$_1$-C$_4$)alkyl, CF$_3$, methoxy or methyl-S(O)$_p$; (C$_3$-C$_6$)alkenyl, (C$_3$-C$_6$)haloalkenyl, phenyl-(C$_3$-C$_6$)alkenyl, (C$_3$-C$_6$)alkynyl, phenyl-(C$_3$-C$_6$)alkynyl, oxetanyl, furfuryl, tetrahydrofuryl;

$R^{38}$ is H or (C$_1$-C$_4$)alkyl;

$R^{39}$ is identical or different at each occurrence and is H, (C$_1$-C$_4$)alkyl, (C$_1$-C$_4$)alkylcarbonyl, or the two radicals $R^{39}$ together are (C$_4$-C$_5$)alkylene;

$R^{40}$ and $R^{41}$ are independently of one another each identical or different and are H, $(C_1-C_4)$alkyl, or the two radicals $R^{40}$ and/or $R^{41}$ together are $(C_4-C_5)$alkylene, it being possible for one $CH_2$ group to be replaced by O or S or for one or two $CH_2$ groups to be replaced by $-NR^c-$;

$R^c$ is H or $(C_1-C_8)$alkyl;

$R^{42}$ is identical or different at each occurrence and is H, $(C_1-C_8)$alkyl, or the two radicals $R^{42}$ together are $(C_2-C_6)$ alkylene;

$R^{43}$ is H, $(C_1-C_8)$alkyl, substituted or unsubstituted phenyl, or benzyl which is unsubstituted or is substituted on the phenyl ring;

$R^{44}$ is identical or different at each occurrence and is H, $(C_1-C_8)$alkyl, phenyl, phenyl-$(C_1-C_8)$alkyl, it being possible for a phenyl ring to be substituted by F, Cl, Br, $NO_2$, CN, $OCH_3$, $(C_1-C_4)$alkyl or $CH_3SO_2-$; $(C_1-C_4)$alkoxy-$(C_1-C_8)$alkyl, $(C_3-C_6)$alkenyl, $(C_3-C_6)$alkynyl, $(C_3-C_6)$cycloalkyl or two radicals $R^{44}$ together are $(C_4-C_5)$alkylene, it being possible for one $CH_2$ group to be replaced by O or S or for one or two $CH_2$ groups to be replaced by $-NR^d-$;

$R^d$ is H or $(C_1-C_4)$alkyl;

m" is 0 or 1, and p is 0, 1 or 2;

including the stereoisomers and the agriculturally useful salts.

For the purpose of application, the formations in their commercially customary form are where appropriate subjected to customary dilution, by means of water in the case for example of wettable powders, emulsifiable concentrates, dispersions, and water-dispersible granules. Preparations in dust form, soil granules and broadcasting granules, and also sprayable solutions, are typically not diluted with further inert substances prior to their application.

The application rate of the compounds of the invention that is required varies with the external conditions such as temperature, humidity, and identity of the herbicide used. The rate may fluctuate within wide limits—for example, between 0.001 and 10.0 kg or more of active substance per hectare—and is preferably between 0.005 and 5 kg/ha.

EXAMPLES

A. Synthesis Examples

Example A1

N-(tert-Butyl)-2-methoxybenzenesulfonamide

A solution of 30.00 g (145.17 mmol) of 2-methoxybenzenesulfonyl chloride in 150 ml of dichloromethane is admixed dropwise at 5-10° C. with 22.30 g (304.87 mmol) of tert-butylamine. The mixture is then stirred at room temperature for 2 h. Following extraction with water, the organic phase is dried over sodium sulfate and evaporated to dryness. This gives 31.10 g (88% of theory) of N-(tert-butyl)-2-methoxybenzenesulfonamide.

$^1$H NMR (CDCl$_3$): 7.91 (dd, J=1.7, 7.8, 1H); 7.50 (m, 1H); 7.03 (m, 2H); 4.93 (br s, 1H); 3.98 (s, 3H); 1.17 (s, 9H).

Example A2

N-(tert-Butyl)-2-iodo-6-methoxybenzenesulfonamide (Example 2.092b)

A solution of 30.00 g (123.29 mmol) of N-(tert-butyl)-2-methoxybenzenesulfonamide in 400 ml of tetrahydrofuran is cooled to −70° C. and slowly admixed with a solution of 110.96 ml (277.41 mmol) of a 2.5 molar n-butyllithium solution in THF. The solution is subsequently warmed briefly to −30° C. and then cooled again to −60° C. At this temperature a solution of 31.29 g (123.29 mmol) of iodine in 200 ml of tetrahydrofuran is added dropwise. Subsequently the reaction solution is stirred at room temperature overnight. Following extraction with water, the organic phase is dried over sodium sulfate and evaporated to dryness. This gives 42.40 g (93% of theory) of N-(tert-butyl)-2-iodo-6-methoxybenzenesulfonamide.

Example A3

2-Iodo-6-methoxybenzenesulfonamide (Example 2.092a)

42.40 g (114.84 mmol) N-(tert-butyl)-2-iodo-6-methoxybenzenesulfonamide are stirred in 265 ml of trifluoroacetic acid at room temperature for 3 h. Thereafter the reaction mixture is poured into ice-water and the precipitate is isolated by filtration and washed to neutrality with water. This gives 32.40 g (90% of theory) of 2-iodo-6-methoxybenzenesulfonamide.

Example A4

4-Cyclopropyl-3-ethoxy-N-[(2-iodo-6-methoxyphenyl)sulfonyl]-5-oxo-4,5-dihydro-1H-1,2,4-triazole-1-carboxamide (Example 1.191)

A solution of 250 mg (0.80 mmol) of 2-iodo-6-methoxybenzenesulfonamide in 3 ml of acetonitrile is admixed at room temperature first with 254.08 mg (0.88 mmol) of 4-cyclopropyl-3-ethoxy-5-oxo-1-phenyloxycarbonyl-4,5-dihydro-1H-1,2,4-triazole and then slowly with 0.24 ml (1.60 mmol) of 1,8-diazabicyclo[5.4.0]undec-7-ene. After 60 min of stirring at room temperature the solution is adjusted slowly to a pH of 1 using 2 N salt solution. The precipitated solid is filtered off with suction, washed with diisopropyl ether and acetonitrile, and dried. This gives 267 mg (62% of theory) of 4-cyclopropyl-3-ethoxy-N-[(2-iodo-6-methoxyphenyl)sulfonyl]-5-oxo-4,5-dihydro-1H-1,2,4-triazole-1-carboxamide.

Example A5

2-Hydroxy-6-iodobenzenesulfonamide (Example 2.300a)

0.50 g (1.60 mmol) of 2-iodo-6-methoxybenzenesulfonamide are introduced in 10 ml of dichloromethane at room temperature and this initial charge is cautiously admixed with 0.6 g (2.40 mmol) of boron tribromide. The reaction solution is stirred at room temperature for a further 45 min and then added to 2 N hydrochloric acid. Following extraction with dichloromethane, the organic phase is dried and evaporated. This gives 0.43 g (90% of theory) of 2-hydroxy-6-iodobenzenesulfonamide.

Example A6

2-Iodo-6-propoxybenzenesulfonamide (Example 2.095a)

5.00 g (16.72 mmol) of 2-hydroxy-6-iodobenzenesulfonamide are introduced in 50 ml of dimethylformamide and this initial charge is admixed with 2.54 g (18.39 mmol) of potassium carbonate. This mixture is stirred at room temperature for 1 h. Thereafter 3.13 g (18.39 mmol) of propyl iodide are added dropwise and the reaction mixture is stirred at room temperature for 3 h. It is then poured into water, and the product precipitates out. The solid is washed with water and dried. This gives 4.00 g (70% of theory) of 2-iodo-6-propoxy-benzenesulfonamide.

Example A7

N-(tert-Butyl)-2-fluoro-6-iodobenzenesulfonamide (Example 2.001 b)

30 g (0.13 mol) of (N-tert-butyl)-2-fluorobenzenesulfonamide, obtained from the reaction of 2-fluorobenzenesulfonyl chloride with N-tert-butylamine in analogy to example A1, are introduced in 300 ml of dry tetrahydrofuran. The solution is cooled to –70° C. and a solution of 18.28 g (0.285 mol) of n-butyllithium (2.5 molar in tetrahydrofuran) is added dropwise. Thereafter the reaction solution is warmed to –30° C. over 30 min, after which it is cooled again to –70° C. Then 36.21 g (0.143 mol) of iodine in 200 ml of dry tetrahydrofuran are added dropwise. Following the addition the reaction solution is warmed slowly to room temperature and stirred for 12 h. Thereafter it is washed with 50% strength aqueous sodium thiosulfate solution and water. The organic phase is dried and evaporated. This gives 40.8 g (88% of theory) of N-(tert-butyl)-2-fluoro-6-iodobenzenesulfonamide.

Example A8

2-(2,2-Difluoroethoxy)-6-iodobenzenesulfonamide (Example 2.187a)

0.64 g (26.57 mmol) of sodium hydride is introduced in 10 ml of dry tetrahydrofuran and this initial charge is slowly admixed at room temperature with 2.18 g (26.57 mmol) of 2,2-difluoroethanol. The reaction mixture is stirred at room temperature until the evolution of gas ceases. Thereafter 4.00 g (13.29 mmol) of 2-fluoro-6-iodo-benzenesulfonamide, obtained from the reaction of N-(tert-butyl)-2-fluoro-6-iodo-benzenesulfonamide with trifluoroacetic acid in analogy to example A3, in solution in 20 ml of dry tetrahydrofuran, are added dropwise. This reaction mixture is exposed to a microwave energy of 100 watts at 150° C. for 30 min. Thereafter the pH is adjusted to 4-5 using 2 N hydrochloric acid and the mixture is partitioned in water/ethyl acetate, the organic phase being dried and evaporated. This gives 3.00 g (62% of theory) of 2-(2,2-difluoroethoxy)-6-iodobenzenesulfonamide.

Example A9

2-Iodo-6-(methylthio)benzenesulfonamide (Example 2.208a)

30.00 g (99.64 mmol) of 2-fluoro-6-iodobenzenesulfonamide, obtained from the reaction of N-(tert-butyl)-2-fluoro-6-iodobenzenesulfonamide with trifluoroacetic acid in analogy to example A3, are introduced together with 15.15 g (109.61 mmol) of potassium carbonate in 250 ml of dimethylformamide. At room temperature 7.68 g (109.61 mmol) of sodium thiomethoxide are added in portions, after which the mixture is stirred at room temperature for 12 h. It is poured into 150 ml of ice-water, adjusted to a pH of 4-5 using 2 N hydrochloric acid, and extracted with ethyl acetate. The organic phase is dried and evaporated. Preparative HPLC (reversed phase, 0.05% trifluoroacetic acid in water/acetonitrile, gradient: in 30 min, 25% to 100% acetonitrile) gives 7.40 g (23% of theory) of 2-iodo-6-(methylthio)benzenesulfonamide.

The compounds described in tables 1 and 2 below are obtained in the same way as examples A1-A9 above.

Abbreviations in tables 1 and 2 below:

*=$^1$H NMR data are listed after tables 1 and 2, respectively

Me=methyl

Ph=phenyl

Het=heterocycle, with Het standing for one of the radicals H1 to H20 below

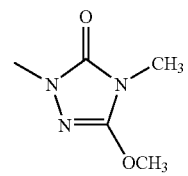
H1

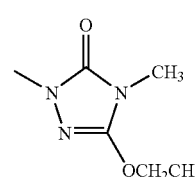
H2

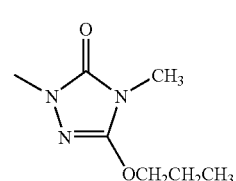
H3

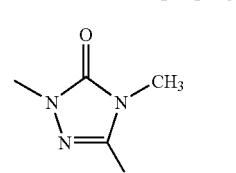
H4

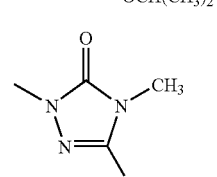
H5

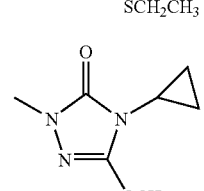
H6

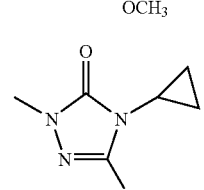
H7

-continued
H8 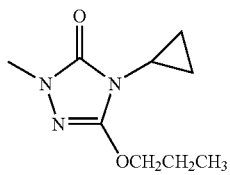
H9 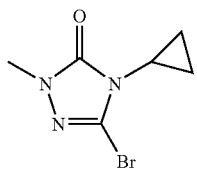
H10 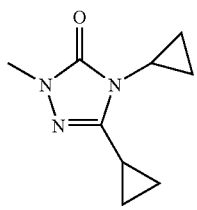
H11 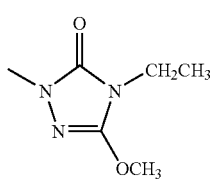
H12 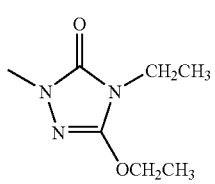
H13 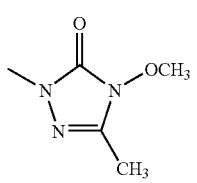
H14 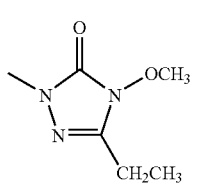
H15 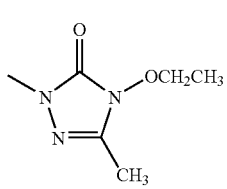
-continued
H16 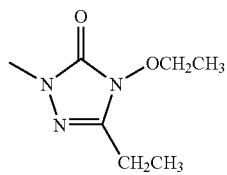
H17 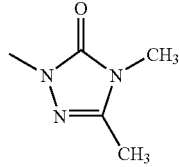
H18 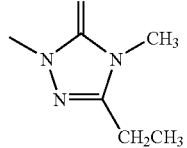
H19 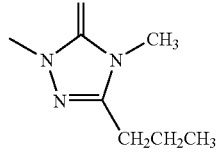
H20 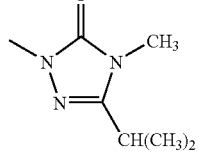
TABLE 1
Compounds of the formula (I-a)
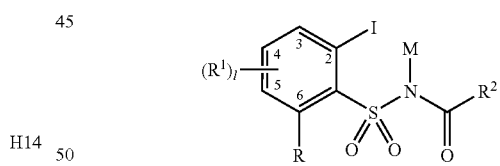
(I-a)
| | R | R¹ | M | Het | ¹H NMR |
|---|---|---|---|---|---|
| 1.001 | H | — | H | H1 | * |
| 1.002 | H | — | Na | H1 | |
| 1.003 | H | 5-CH$_3$ | H | H1 | |
| 1.004 | H | — | H | H2 | * |
| 1.005 | H | — | H | H3 | * |
| 1.006 | H | — | H | H4 | |
| 1.007 | H | — | H | H5 | |
| 1.008 | H | — | H | H6 | * |
| 1.009 | H | — | Na | H6 | |
| 1.010 | H | 5-CH$_3$ | H | H6 | |
| 1.011 | H | — | H | H7 | * |
| 1.012 | H | — | Na | H1 | |
| 1.013 | H | 5-CH$_3$ | H | H7 | |
| 1.014 | H | — | H | H8 | * |
| 1.015 | H | — | H | H11 | |
| 1.016 | H | — | H | H13 | |
| 1.017 | H | — | H | H14 | |

TABLE 1-continued

Compounds of the formula (I-a)

(I-a)

| | R | R¹ | M | Het | ¹H NMR |
|---|---|---|---|---|---|
| 1.018 | H | — | H | H15 | |
| 1.019 | H | — | H | H16 | |
| 1.020 | H | — | H | H17 | |
| 1.021 | F | — | H | H1 | * |
| 1.022 | F | — | H | H2 | * |
| 1.023 | F | — | H | H3 | * |
| 1.024 | F | — | H | H4 | * |
| 1.025 | F | — | H | H5 | |
| 1.026 | F | — | H | H6 | |
| 1.027 | F | — | H | H7 | * |
| 1.028 | F | — | H | H8 | * |
| 1.029 | F | — | H | H11 | |
| 1.030 | F | — | H | H15 | |
| 1.031 | F | — | H | H16 | |
| 1.032 | Cl | — | H | H1 | |
| 1.033 | Cl | — | H | H6 | |
| 1.034 | Cl | — | H | H1 | |
| 1.035 | Br | — | H | H1 | |
| 1.036 | I | — | H | H1 | |
| 1.037 | CH₃ | — | H | H1 | * |
| 1.038 | CH₃ | — | H | H2 | * |
| 1.039 | CH₃ | — | H | H3 | * |
| 1.040 | CH₃ | — | H | H4 | * |
| 1.041 | CH₃ | — | H | H5 | |
| 1.042 | CH₃ | — | H | H6 | * |
| 1.043 | CH₃ | — | H | H1 | * |
| 1.044 | CH₃ | — | H | H8 | * |
| 1.045 | CH₃ | — | H | H11 | |
| 1.046 | CH₃ | — | H | H13 | |
| 1.047 | CH₃ | — | H | H14 | |
| 1.048 | CH₃ | — | H | H15 | |
| 1.049 | CH₃ | — | H | H16 | |
| 1.050 | CH₃ | — | H | H17 | |
| 1.051 | CH₂CH₃ | — | H | H1 | |
| 1.052 | CH₂CH₃ | — | H | H2 | |
| 1.053 | CH₂CH₃ | — | H | H6 | |
| 1.054 | CH₂CH₃ | — | H | H7 | |
| 1.055 | (CH₂)₂CH₃ | — | H | H1 | |
| 1.056 | CH(CH₃)₂ | — | H | H1 | |
| 1.057 | (CH₂)₃CH₃ | — | H | H1 | |
| 1.058 | CH(CH₃)CH₂CH₃ | — | H | H1 | |
| 1.059 | CH₂CH(CH₃)₂ | — | H | H1 | |
| 1.060 | C(CH₃)₃ | — | H | H1 | |
| 1.061 | C(CH₃)₃ | — | H | H2 | |
| 1.062 | C(CH₃)₃ | — | H | H6 | |
| 1.063 | C(CH₃)₃ | — | H | H7 | |
| 1.064 | CH=CH₂ | — | H | H1 | |
| 1.065 | CH=CH₂ | — | H | H2 | |
| 1.066 | CH=CH₂ | — | H | H6 | |
| 1.067 | CH=CH₂ | — | H | H7 | |
| 1.068 | C(CH₃)=CH₂ | — | H | H1 | |
| 1.069 | C≡CH | — | H | H1 | |
| 1.070 | C≡CH | — | H | H2 | |
| 1.071 | C≡CH | — | H | H6 | |
| 1.072 | C≡CH | — | H | H1 | |
| 1.073 | C≡CCH₃ | — | H | H1 | |
| 1.074 | C≡CCH₂CH₃ | — | H | H1 | |
| 1.075 | CH₂CH=CH₂ | — | H | H1 | |
| 1.076 | CH₂C(CH₃)=CH₂ | — | H | H1 | |
| 1.077 | CH₂C≡CH | — | H | H1 | |
| 1.078 | CH₂C≡CCH₃ | — | H | H1 | |
| 1.079 | CH₂C≡CCH₂CH₃ | — | H | H1 | |
| 1.080 | cyclopropyl | — | H | H1 | |
| 1.081 | cyclopropyl | — | H | H2 | |
| 1.082 | cyclopropyl | — | H | H3 | |
| 1.083 | cyclopropyl | — | H | H4 | |
| 1.084 | cyclopropyl | — | H | H5 | |
| 1.085 | cyclopropyl | — | H | H6 | |
| 1.086 | cyclopropyl | — | H | H7 | |
| 1.087 | cyclopropyl | — | H | H8 | |
| 1.088 | cyclopropyl | — | H | H11 | |
| 1.089 | cyclopropyl | — | H | H13 | |
| 1.090 | cyclopropyl | — | H | H14 | |
| 1.091 | cyclopropyl | — | H | H15 | |
| 1.092 | cyclopropyl | — | H | H16 | |
| 1.093 | cyclopropyl | — | H | H17 | |
| 1.094 | 2,2-di-F-cyclopropyl | — | H | H1 | |
| 1.095 | 2,2-di-Cl-cyclopropyl | — | H | H1 | |
| 1.096 | 2,2-di-CH₃-cyclopropyl | — | H | H1 | |
| 1.097 | cyclobutyl | — | H | H1 | |
| 1.098 | cyclopentyl | — | H | H1 | |
| 1.099 | cyclohexyl | — | H | H1 | |
| 1.100 | CH₂cyclopropyl | — | H | H1 | |
| 1.101 | CH₂cyclobutyl | — | H | H1 | |
| 1.102 | CH₂cyclopentyl | — | H | H1 | |
| 1.103 | CH₂cyclohexyl | — | H | H1 | |
| 1.104 | CH₂OCH₃ | — | H | H1 | |
| 1.105 | CH₂OCH₂CH₃ | — | H | H1 | |
| 1.106 | CH(CH₃)OCH₃ | — | H | H1 | |
| 1.107 | Ph | — | H | H1 | |
| 1.108 | 2-F-Ph | — | H | H1 | |
| 1.109 | 3-F-Ph | — | H | H1 | |
| 1.110 | 4-F-Ph | — | H | H1 | |
| 1.111 | 2,6-di-F-Ph | — | H | H1 | |
| 1.112 | 2,4-di-F-Ph | — | H | H1 | |
| 1.113 | 2-Cl-Ph | — | H | H1 | |
| 1.114 | 3-Cl-Ph | — | H | H1 | |
| 1.115 | 4-Cl-Ph | — | H | H1 | |
| 1.116 | 2,6-di-Cl-Ph | — | H | H1 | |
| 1.117 | 2,4-di-Cl-Ph | — | H | H1 | |
| 1.118 | 2-MeO-Ph | — | H | H1 | |
| 1.119 | 3-MeO-Ph | — | H | H1 | |
| 1.120 | 4-MeO-Ph | — | H | H1 | |
| 1.121 | 2,4-di-MeO-Ph | — | H | H1 | |
| 1.122 | 2-Me-Ph | — | H | H1 | |
| 1.123 | 3-Me-Ph | — | H | H1 | |
| 1.124 | 4-Me-Ph | — | H | H1 | |
| 1.125 | 2-CF₃-Ph | — | H | H1 | |
| 1.126 | 3-CF₃-Ph | — | H | H1 | |
| 1.127 | 4-CF₃-Ph | — | H | H1 | |
| 1.128 | CH₂Ph | — | H | H1 | |
| 1.129 | CH₂-2-F-Ph | — | H | H1 | |
| 1.130 | CH₂-2,4-di-F-Ph | — | H | H1 | |
| 1.131 | CH₂-2-MeO-Ph | — | H | H1 | |
| 1.132 | CH₂-3-MeO-Ph | — | H | H1 | |
| 1.133 | CF₃ | — | H | H1 | * |
| 1.134 | CF₃ | — | Na | H1 | |
| 1.135 | CF₃ | 5-CH₃ | H | H1 | |
| 1.136 | CF₃ | — | H | H2 | * |
| 1.137 | CF₃ | — | H | H3 | * |
| 1.138 | CF₃ | — | H | H4 | * |
| 1.139 | CF₃ | — | H | H5 | |
| 1.140 | CF₃ | — | H | H6 | * |
| 1.141 | CF₃ | — | Na | H6 | |
| 1.142 | CF₃ | 5-CH₃ | H | H6 | |
| 1.143 | CF₃ | — | H | H7 | * |
| 1.144 | CF₃ | — | Na | H7 | |
| 1.145 | CF₃ | 5-CH₃ | H | H7 | |
| 1.146 | CF₃ | — | H | H8 | |
| 1.147 | CF₃ | — | H | H11 | |
| 1.148 | CF₃ | — | H | H13 | |
| 1.149 | CF₃ | — | H | H14 | |

TABLE 1-continued

Compounds of the formula (I-a)

(I-a)

| | R | R¹ | M | Het | ¹H NMR |
|---|---|---|---|---|---|
| 1.150 | CF₃ | — | H | H15 | |
| 1.151 | CF₃ | — | H | H16 | |
| 1.152 | CF₃ | — | H | H17 | |
| 1.153 | CHF₂ | — | H | H1 | |
| 1.154 | CHF₂ | — | H | H2 | |
| 1.155 | CHF₂ | — | H | H6 | |
| 1.156 | CHF₂ | — | H | H7 | |
| 1.157 | CH₂F | — | H | H1 | |
| 1.158 | CH₂CF₃ | — | H | H1 | |
| 1.159 | CH₂CHF₂ | — | H | H1 | |
| 1.160 | CH₂CH₂F | — | H | H1 | |
| 1.161 | CF=CH₂ | — | H | H1 | |
| 1.162 | CH=CF₂ | — | H | H1 | |
| 1.163 | CF₂CH=CH₂ | — | H | H1 | |
| 1.164 | CH=CH-CF₃ | — | H | H1 | |
| 1.165 | CHFCH=CH₂ | — | H | H1 | |
| 1.166 | CN | — | H | H1 | |
| 1.167 | NO₂ | — | H | H1 | |
| 1.168 | NH₂ | — | H | H1 | |
| 1.169 | NHCH₃ | — | H | H1 | |
| 1.170 | N(CH₃)₂ | — | H | H1 | |
| 1.171 | N(CH₃)CH₂CH=CH₂ | — | H | H1 | |
| 1.172 | N(CH₃)CH₂C≡CH | — | H | H1 | |
| 1.173 | NH-cyclopropyl | — | H | H1 | |
| 1.174 | NH-cyclopropyl | — | H | H2 | |
| 1.175 | NH-cyclopropyl | — | H | H3 | |
| 1.176 | NH-cyclopropyl | — | H | H4 | |
| 1.177 | NH-cyclopropyl | — | H | H5 | |
| 1.178 | NH-cyclopropyl | — | H | H6 | |
| 1.179 | NH-cyclopropyl | — | H | H7 | |
| 1.180 | NH-cyclopropyl | — | H | H8 | |
| 1.181 | N(CH₃)-cyclopropyl | — | H | H1 | |
| 1.182 | N(CH₂CH₃)-cyclopropyl | — | H | H1 | |
| 1.183 | NHO(O)H | — | H | H1 | |
| 1.184 | NHC(O)CH₃ | H | H1 | | |
| 1.185 | NHC(O)OCH₃ | — | H | H1 | |
| 1.186 | NHSO₂CH₃ | — | H | H1 | |
| 1.187 | NHSO₂CF₃ | — | H | H1 | |
| 1.188 | NHSO₂CHF₂ | — | H | H1 | |
| 1.189 | NHSO₂CH₂F | — | H | H1 | |
| 1.190 | OH | — | H | H1 | |
| 1.191 | OCH₃ | — | H | H1 | * |
| 1.192 | OCH₃ | — | Na | H1 | |
| 1.193 | OCH₃ | 5-CH₃ | H | H1 | |
| 1.194 | OCH₃ | — | H | H2 | * |
| 1.195 | OCH₃ | — | H | H3 | * |
| 1.196 | OCH₃ | — | H | H4 | * |
| 1.197 | OCH₃ | — | H | H5 | * |
| 1.198 | OCH₃ | — | H | H6 | * |
| 1.199 | OCH₃ | — | Na | H6 | |
| 1.200 | OCH₃ | 5-CH₃ | H | H6 | |
| 1.201 | OCH₃ | — | H | H7 | * |
| 1.202 | OCH₃ | — | Na | H7 | |
| 1.203 | OCH₃ | 5-CH₃ | H | H7 | |
| 1.204 | OCH₃ | — | H | H8 | * |
| 1.205 | OCH₃ | — | H | H11 | |
| 1.206 | OCH₃ | — | H | H13 | |
| 1.207 | OCH₃ | — | H | H14 | |
| 1.208 | OCH₃ | — | H | H15 | |
| 1.209 | OCH₃ | — | H | H16 | |
| 1.210 | OCH₃ | — | H | H17 | |
| 1.211 | OCH₂CH₃ | — | H | H1 | * |
| 1.212 | OCH₂CH₃ | — | Na | H1 | |
| 1.213 | OCH₂CH₃ | 5-CH₃ | H | H1 | |
| 1.214 | OCH₂CH₃ | — | H | H2 | * |
| 1.215 | OCH₂CH₃ | — | H | H3 | * |
| 1.216 | OCH₂CH₃ | — | H | H4 | |
| 1.217 | OCH₂CH₃ | — | H | H5 | |
| 1.218 | OCH₂CH₃ | — | H | H6 | * |
| 1.219 | OCH₂CH₃ | — | Na | H6 | |
| 1.220 | OCH₂CH₃ | 5-CH₃ | H | H6 | |
| 1.221 | OCH₂CH₃ | — | H | H7 | * |
| 1.222 | OCH₂CH₃ | — | Na | H7 | |
| 1.223 | OCH₂CH₃ | 5-CH₃ | H | H7 | |
| 1.224 | OCH₂CH₃ | — | H | H8 | |
| 1.225 | OCH₂CH₃ | — | H | H11 | |
| 1.226 | OCH₂CH₃ | — | H | H13 | |
| 1.227 | OCH₂CH₃ | — | H | H14 | |
| 1.228 | OCH₂CH₃ | — | H | H15 | |
| 1.229 | OCH₂CH₃ | — | H | H16 | |
| 1.230 | OCH₂CH₃ | — | H | H17 | |
| 1.231 | O(CH₂)₂CH₃ | — | H | H1 | * |
| 1.232 | O(CH₂)₂CH₃ | — | Na | H1 | |
| 1.233 | O(CH₂)₂CH₃ | 5-CH₃ | H | H1 | |
| 1.234 | O(CH₂)₂CH₃ | — | H | H2 | |
| 1.235 | O(CH₂)₂CH₃ | — | H | H3 | * |
| 1.236 | O(CH₂)₂CH₃ | — | H | H4 | * |
| 1.237 | O(CH₂)₂CH₃ | — | H | H5 | * |
| 1.238 | O(CH₂)₂CH₃ | — | H | H6 | * |
| 1.239 | O(CH₂)₂CH₃ | — | Na | H6 | |
| 1.240 | O(CH₂)₂CH₃ | 5-CH₃ | H | H6 | |
| 1.241 | O(CH₂)₂CH₃ | — | H | H7 | * |
| 1.242 | O(CH₂)₂CH₃ | — | Na | H7 | |
| 1.243 | O(CH₂)₂CH₃ | 5-CH₃ | H | H7 | |
| 1.244 | O(CH₂)₂CH₃ | — | H | H8 | * |
| 1.245 | O(CH₂)₂CH₃ | — | H | H11 | |
| 1.246 | O(CH₂)₂CH₃ | — | H | H13 | |
| 1.247 | O(CH₂)₂CH₃ | — | H | H14 | |
| 1.248 | O(CH₂)₂CH₃ | — | H | H15 | |
| 1.249 | O(CH₂)₂CH₃ | — | H | H16 | |
| 1.250 | O(CH₂)₂CH₃ | — | H | H17 | |
| 1.251 | OCH(CH₃)₂ | — | H | H1 | * |
| 1.252 | OCH(CH₃)₂ | — | Na | H1 | |
| 1.253 | OCH(CH₃)₂ | 5-CH₃ | H | H1 | |
| 1.254 | OCH(CH₃)₂ | — | H | H2 | * |
| 1.255 | OCH(CH₃)₂ | — | H | H3 | * |
| 1.256 | OCH(CH₃)₂ | — | H | H4 | * |
| 1.257 | OCH(CH₃)₂ | — | H | H5 | |
| 1.258 | OCH(CH₃)₂ | — | H | H6 | * |
| 1.259 | OCH(CH₃)₂ | — | Na | H6 | |
| 1.260 | OCH(CH₃)₂ | 5-CH₃ | H | H6 | |
| 1.261 | OCH(CH₃)₂ | — | H | H7 | * |
| 1.262 | OCH(CH₃)₂ | — | Na | H7 | |
| 1.263 | OCH(CH₃)₂ | 5-CH₃ | H | H7 | |
| 1.264 | OCH(CH₃)₂ | — | H | H8 | * |
| 1.265 | OCH(CH₃)₂ | — | H | H11 | |
| 1.266 | OCH(CH₃)₂ | — | H | H13 | |
| 1.267 | OCH(CH₃)₂ | — | H | H14 | |
| 1.268 | OCH(CH₃)₂ | — | H | H15 | |
| 1.269 | OCH(CH₃)₂ | — | H | H16 | |
| 1.270 | OCH(CH₃)₂ | — | H | H17 | |
| 1.271 | OCH(CH₃)₂ | — | Na | H1 | |
| 1.272 | OCH(CH₃)₂ | 5-CH₃ | H | H1 | |
| 1.273 | O(CH₂)₃CH₃ | — | H | H1 | * |
| 1.274 | O(CH₂)₃CH₃ | — | H | H2 | * |
| 1.275 | O(CH₂)₃CH₃ | — | H | H3 | * |
| 1.276 | O(CH₂)₃CH₃ | — | H | H4 | * |
| 1.277 | O(CH₂)₃CH₃ | — | H | H5 | |
| 1.278 | O(CH₂)₃CH₃ | — | H | H6 | * |
| 1.279 | O(CH₂)₃CH₃ | — | H | H7 | * |
| 1.280 | O(CH₂)₃CH₃ | — | H | H8 | * |
| 1.281 | OCH(CH₃)CH₂CH₃ | — | H | H1 | * |

TABLE 1-continued

Compounds of the formula (I-a)

(I-a)

| | R | R¹ | M | Het | ¹H NMR |
|---|---|---|---|---|---|
| 1.282 | OCH(CH₃)CH₂CH₃ | — | H | H2 | |
| 1.283 | OCH(CH₃)CH₂CH₃ | — | H | H3 | |
| 1.284 | OCH(CH₃)CH₂CH₃ | — | H | H4 | |
| 1.285 | OCH(CH₃)CH₂CH₃ | — | H | H5 | |
| 1.286 | OCH(CH₃)CH₂CH₃ | — | H | H6 | * |
| 1.287 | OCH(CH₃)CH₂CH₃ | — | H | H7 | |
| 1.288 | OCH(CH₃)CH₂CH₃ | — | H | H8 | |
| 1.289 | OCH₂CH(CH₃)₂ | — | H | H1 | * |
| 1.290 | OCH₂CH(CH₃)₂ | — | H | H2 | * |
| 1.291 | OCH₂CH(CH₃)₂ | — | H | H3 | |
| 1.292 | OCH₂CH(CH₃)₂ | — | H | H4 | |
| 1.293 | OCH₂CH(CH₃)₂ | — | H | H5 | |
| 1.294 | OCH₂CH(CH₃)₂ | — | H | H6 | * |
| 1.295 | OCH₂CH(CH₃)₂ | — | H | H7 | * |
| 1.296 | OCH₂CH(CH₃)₂ | — | H | H8 | |
| 1.297 | OC(CH₃)₃ | — | H | H1 | |
| 1.298 | OC(CH₃)₃ | — | H | H2 | |
| 1.299 | OC(CH₃)₃ | — | H | H3 | |
| 1.300 | OC(CH₃)₃ | — | H | H4 | |
| 1.301 | OC(CH₃)3 | — | H | H5 | |
| 1.302 | OC(CH₃)₃ | — | H | H6 | |
| 1.303 | OC(CH₃)₃ | — | H | H1 | |
| 1.304 | OC(CH₃)₃ | — | H | H8 | |
| 1.305 | OCH=CH₂ | — | H | H1 | |
| 1.306 | OCH=CH₂ | — | H | H2 | |
| 1.307 | OCH=CH₂ | — | H | H6 | |
| 1.308 | OCH=CH₂ | — | H | H1 | |
| 1.309 | OC(CH₃)=CH₂ | — | H | H1 | |
| 1.310 | OCH=CH(CH₃) | — | H | H1 | |
| 1.311 | OCH=C(CH₃)₂ | — | H | H1 | |
| 1.312 | OC(CH₃)=CHCH₃ | — | H | H1 | |
| 1.313 | OC(CH₃)=C(CH₃)₂ | — | H | H1 | |
| 1.314 | OC≡CH | — | H | H1 | |
| 1.315 | OC≡CH | — | H | H2 | |
| 1.316 | OC≡CH | — | H | H6 | |
| 1.317 | OC≡CH | — | H | H1 | |
| 1.318 | OC≡CCH₃ | — | H | H1 | |
| 1.319 | OC≡CCH₂CH₃ | — | H | H1 | |
| 1.320 | OCH₂OH=CH₂ | — | H | H1 | |
| 1.321 | OCH₂CH=CH₂ | — | H | H2 | |
| 1.322 | OCH₂CH=CH₂ | — | H | H6 | |
| 1.323 | OCH₂CH=CH₂ | — | H | H7 | |
| 1.324 | OCH₂C(CH₃)=CH₂ | — | H | H1 | |
| 1.325 | OCH₂CH=CHCH₃ | — | H | H1 | |
| 1.326 | OCH₂CH=C(CH₃)₂ | — | H | H1 | |
| 1.327 | OCH₂C(CH₃)=CHCH₃ | — | H | H1 | |
| 1.328 | OCH₂C(CH₃)=C(CH₃)₂ | — | H | H1 | |
| 1.329 | OCH(CH₃)CH=CH₂ | — | H | H1 | |
| 1.330 | OCH₂C≡CH | — | H | H1 | |
| 1.331 | OCH₂C≡CH | — | H | H2 | |
| 1.332 | OCH₂C≡CH | — | H | H6 | |
| 1.333 | OCH₂C≡CH | — | H | H7 | |
| 1.334 | OCH₂C≡CCH₃ | — | H | H1 | |
| 1.335 | OCH₂C≡CCH₂CH₃ | — | H | H1 | |
| 1.336 | OCH(CH₃)C≡CH | — | H | H1 | |
| 1.337 | O-cyclopropyl | — | H | H1 | |
| 1.338 | O-cyclopropyl | — | H | H2 | |
| 1.339 | O-cyclopropyl | — | H | H6 | |
| 1.340 | O-cyclopropyl | — | H | H7 | |
| 1.341 | O-2,2-di-Cl-cyclopropyl | — | H | H1 | |
| 1.342 | O-2,2-di-F-cyclopropyl | — | H | H1 | |
| 1.343 | O-cyclobutyl | — | H | H1 | |
| 1.344 | O-cyclopentyl | — | H | H1 | |
| 1.345 | O-cyctohexyl | — | H | H1 | |
| 1.346 | OCH₂-cyclopropyl | — | H | H1 | * |
| 1.347 | OCH₂-cyclopropyl | — | Na | H1 | |
| 1.348 | OCH₂-cyclopropyl | 5-CH₃ | H | H1 | |
| 1.349 | OCH₂-cyclopropyl | — | H | H2 | * |
| 1.350 | OCH₂-cyclopropyl | — | H | H3 | * |
| 1.351 | OCH₂-cyclopropyl | — | H | H4 | |
| 1.352 | OCH₂-cyclopropyl | — | H | H5 | |
| 1.353 | OCH₂-cyclopropyl | — | H | H6 | * |
| 1.354 | OCH₂-cyclopropyl | — | Na | H6 | |
| 1.355 | OCH₂-cyclopropyl | 5-CH₃ | H | H6 | |
| 1.356 | OCH₂-cyclopropyl | — | H | H7 | * |
| 1.357 | OCH₂-cyclopropyl | — | Na | H7 | |
| 1.358 | OCH₂-cyclopropyl | 5-CH₃ | H | H7 | |
| 1.359 | OCH₂-cyclopropyl | — | H | H8 | * |
| 1.360 | OCH₂-cyclopropyl | — | H | H11 | |
| 1.361 | OCH₂-cyclopropyl | — | H | H13 | |
| 1.362 | OCH₂-cyclopropyl | — | H | H14 | |
| 1.363 | OCH₂-cyclopropyl | — | H | H15 | |
| 1.364 | OCH₂-cyclopropyl | — | H | H16 | |
| 1.365 | OCH₂-cyclopropyl | — | H | H17 | |
| 1.366 | OCH(CH₃)-cyclopropyl | — | H | H1 | |
| 1.367 | OCH(CH₃)-cyclopropyl | — | H | H2 | |
| 1.368 | OCH(CH₃)-cyclopropyl | — | H | H6 | |
| 1.369 | OCH(CH₃)-cyclopropyl | — | H | H7 | |
| 1.370 | OCH₂-2-Me-cyclopropyl | — | H | H1 | |
| 1.371 | OCH₂-2,2-di-Me-cyclopropyl | — | H | H1 | |
| 1.372 | OCH₂-2,2-di-Cl-cyclopropyl | — | H | H1 | |
| 1.373 | OCH₂-2,2-di-F-cyclopropyl | — | H | H1 | |
| 1.374 | OCH₂-cyclobutyl | — | H | H1 | |
| 1.375 | OCH₂-cyclopentyl | — | H | H1 | |
| 1.376 | OCH₂-cyclopentyl | — | H | H2 | |
| 1.377 | OCH₂-cyclopentyl | — | H | H6 | |
| 1.378 | OCH₂-cyclopentyl | — | H | H1 | |
| 1.379 | OCH(CH₃)-cyclopentyl | — | H | H1 | |
| 1.380 | OCH₂-cyclohexyl | — | H | H1 | |
| 1.381 | OCH(CH₃)-cyclohexyl | — | H | H1 | |
| 1.382 | OCH₂OCH₃ | — | H | H1 | |
| 1.383 | O(CH₂)₂OCH₃ | — | H | H1 | |
| 1.384 | OCH₂OCH₂CH₃ | — | H | H1 | |
| 1.385 | C(CH₂)₂OCH₂CH₃ | — | H | H1 | |
| 1.386 | OCH(CH₃)OCH₃ | — | H | H1 | |
| 1.387 | O(CH₂)₂Cl | — | H | H1 | |
| 1.388 | O(CH₂)₂Cl | — | H | H2 | |
| 1.389 | O(CH₂)₂Cl | — | H | H3 | |
| 1.390 | O(CH₂)₂Cl | — | H | H4 | |
| 1.391 | O(CH₂)₂Cl | — | H | H5 | |
| 1.392 | O(CH₂)₂Cl | — | H | H6 | |
| 1.393 | O(CH₂)₂Cl | — | H | H7 | |
| 1.394 | O(CH₂)₂Cl | — | H | H8 | |
| 1.395 | O(CH₂)₃Cl | — | H | H1 | |
| 1.396 | O(CH₂)₃Cl | — | H | H2 | |
| 1.397 | O(CH₂)₃Cl | — | H | H3 | |
| 1.398 | O(CH₂)₃Cl | — | H | H4 | |
| 1.399 | O(CH₂)₃Cl | — | H | H5 | |
| 1.400 | O(CH₂)₃Cl | — | H | H6 | |
| 1.401 | O(CH₂)₃Cl | — | H | H7 | |
| 1.402 | O(CH₂)₃Cl | — | H | H8 | |
| 1.403 | OPh | — | H | H1 | |
| 1.404 | O-2-F-Ph | — | H | H1 | |
| 1.405 | O-3-F-Ph | — | H | H1 | |
| 1.406 | O-4-F-Ph | — | H | H1 | |
| 1.407 | O-2,6-di-F-Ph | — | H | H1 | |
| 1.408 | O-2,4-di-F-Ph | — | H | H1 | |
| 1.409 | O-2-Cl-Ph | — | H | H1 | |
| 1.410 | O-3-Cl-Ph | — | H | H1 | |

TABLE 1-continued

Compounds of the formula (I-a)

(I-a)

| | R | R¹ | M | Het | ¹H NMR |
|---|---|---|---|---|---|
| 1.411 | O-4-Cl-Ph | — | H | H1 | |
| 1.412 | O-2,6-di-Cl-Ph | — | H | H1 | |
| 1.413 | O-2,4-di-Cl-Ph | — | H | H1 | |
| 1.414 | O-2-CF₃-Ph | — | H | H1 | |
| 1.415 | O-3-CF₃-Ph | — | H | H1 | |
| 1.416 | O-4-CF₃-Ph | — | H | H1 | |
| 1.417 | O-2-MeO-Ph | — | H | H1 | |
| 1.418 | O-3-MeO-Ph | — | H | H1 | |
| 1.419 | O-4-MeO-Ph | — | H | H1 | |
| 1.420 | O-2,4-di-MeO-Ph | — | H | H1 | |
| 1.421 | O-2-Me-Ph | — | H | H1 | |
| 1.422 | O-3-Me-Ph | — | H | H1 | |
| 1.423 | O-4-Me-Ph | — | H | H1 | |
| 1.424 | OCH₂Ph | — | H | H1 | |
| 1.425 | OCH(CH₃)Ph | — | H | H1 | |
| 1.426 | OCH₂-2-F-Ph | — | H | H1 | |
| 1.427 | OCH₂-3-F-Ph | — | H | H1 | |
| 1.428 | OCH₂-4-F-Ph | — | H | H1 | |
| 1.429 | OCH₂-2,4-di-F-Ph | — | H | H1 | |
| 1.430 | OCH₂-2-Cl-Ph | — | H | H1 | |
| 1.431 | OCH₂-3-Cl-Ph | — | H | H1 | |
| 1.432 | OCH₂-4-Cl-Ph | — | H | H1 | |
| 1.433 | OCH₂-2,4-di-Cl-Ph | — | H | H1 | |
| 1.434 | OCH₂-2-MeO-Ph | — | H | H1 | |
| 1.435 | OCH₂-3-MeO-Ph | — | H | H1 | |
| 1.436 | OCH₂-4-MeO-Ph | — | H | H1 | |
| 1.437 | OCH₂-2-CF₃-Ph | — | H | H1 | |
| 1.438 | OCH₂-3-CF₃-Ph | — | H | H1 | |
| 1.439 | OCH₂-4-CF₃-Ph | — | H | H1 | |
| 1.440 | OCF₃ | — | H | H1 | * |
| 1.441 | OCF₃ | — | Na | H1 | |
| 1.442 | OCF₃ | 5-CH₃ | H | H1 | |
| 1.443 | OCF₃ | — | H | H2 | * |
| 1.444 | OCF₃ | — | H | H3 | * |
| 1.445 | OCF₃ | — | H | H4 | |
| 1.446 | OCF₃ | — | H | H5 | |
| 1.447 | OCF₃ | — | H | H6 | * |
| 1.448 | OCF₃ | — | Na | H6 | |
| 1.449 | OCF₃ | 5-CH₃ | H | H6 | |
| 1.450 | OCF₃ | — | H | H7 | * |
| 1.451 | OCF₃ | — | Na | H7 | |
| 1.452 | OCF₃ | 5-CH₃ | H | H7 | |
| 1.453 | OCF₃ | — | H | H8 | * |
| 1.454 | OCF₃ | — | H | H11 | |
| 1.455 | OCF₃ | — | H | H13 | |
| 1.456 | OCF₃ | — | H | H14 | |
| 1.457 | OCF₃ | — | H | H15 | |
| 1.458 | OCF₃ | — | H | H16 | |
| 1.459 | OCF₃ | — | H | H17 | |
| 1.460 | OCHF₂ | — | H | H1 | * |
| 1.461 | OCHF₂ | — | Na | H1 | |
| 1.462 | OCHF₂ | 5-CH₃ | H | H1 | |
| 1.463 | OCHF₂ | — | H | H2 | * |
| 1.464 | OCHF₂ | — | H | H3 | * |
| 1.465 | OCHF₂ | — | H | H4 | * |
| 1.466 | OCHF₂ | — | H | H5 | |
| 1.467 | OCHF₂ | — | H | H6 | * |
| 1.468 | OCHF₂ | — | Na | H6 | |
| 1.469 | OCHF₂ | 5-CH₃ | H | H6 | |
| 1.470 | OCHF₂ | — | H | H7 | * |
| 1.471 | OCHF₂ | — | Na | H7 | |
| 1.472 | OCHF₂ | 5-CH₃ | H | H7 | |
| 1.473 | OCHF₂ | — | H | H8 | * |
| 1.474 | OCHF₂ | — | H | H11 | |
| 1.475 | OCHF₂ | — | H | H13 | |
| 1.476 | OCHF₂ | — | H | H14 | |
| 1.477 | OCHF₂ | — | H | H15 | |
| 1.478 | OCHF₂ | — | H | H16 | |
| 1.479 | OCHF₂ | — | H | H17 | |
| 1.480 | OCH₂F | — | H | H1 | |
| 1.481 | OCH₂CF₃ | — | H | H1 | * |
| 1.482 | OCH₂CF₃ | — | Na | H1 | |
| 1.483 | OCH₂CF₃ | 5-CH₃ | H | H1 | |
| 1.484 | OCH₂CF₃ | — | H | H2 | |
| 1.485 | OCH₂CF₃ | — | H | H3 | |
| 1.486 | OCH₂CF₃ | — | H | H4 | |
| 1.487 | OCH₂CF₃ | — | H | H5 | |
| 1.488 | OCH₂CF₃ | — | H | H6 | * |
| 1.489 | OCH₂CF₃ | — | Na | H6 | |
| 1.490 | OCH₂CF₃ | 5-CH₃ | H | H6 | |
| 1.491 | OCH₂CF₃ | — | H | H7 | |
| 1.492 | OCH₂CF₃ | — | Na | H7 | |
| 1.493 | OCH₂CF₃ | 5-CH₃ | H | H7 | |
| 1.494 | OCH₂CF₃ | — | H | H8 | |
| 1.495 | OCH₂CF₃ | — | H | H11 | |
| 1.496 | OCH₂CF₃ | — | H | H13 | |
| 1.497 | OCH₂CF₃ | — | H | H14 | |
| 1.498 | OCH₂CF₃ | — | H | H15 | |
| 1.499 | OCH₂CF₃ | — | H | H16 | |
| 1.500 | OCH₂CF₃ | — | H | H17 | |
| 1.501 | OCH₂CHF₂ | — | H | H1 | * |
| 1.502 | OCH₂CHF₂ | — | Na | H1 | |
| 1.503 | OCH₂CHF₂ | 5-CH₃ | H | H1 | |
| 1.504 | OCH₂CHF₂ | — | H | H2 | * |
| 1.505 | OCH₂CHF₂ | — | H | H3 | * |
| 1.506 | OCH₂CHF₂ | — | H | H4 | * |
| 1.507 | OCH₂CHF₂ | — | H | H5 | |
| 1.508 | OCH₂CHF₂ | — | H | H6 | * |
| 1.509 | OCH₂CHF₂ | — | Na | H6 | |
| 1.510 | OCH₂CHF₂ | 5-CH₃ | H | H6 | |
| 1.511 | OCH₂CHF₂ | — | H | H7 | * |
| 1.512 | OCH₂CHF₂ | — | Na | H7 | |
| 1.513 | OCH₂CHF₂ | 5-CH₃ | H | H7 | |
| 1.514 | OCH₂CHF₂ | — | H | H8 | * |
| 1.515 | OCH₂CHF₂ | — | H | H11 | |
| 1.516 | OCH₂CHF₂ | — | H | H13 | |
| 1.517 | OCH₂CHF₂ | — | H | H14 | |
| 1.518 | OCH₂CHF₂ | — | H | H15 | |
| 1.519 | OCH₂CHF₂ | — | H | H16 | |
| 1.520 | OCH₂CHF₂ | — | H | H17 | |
| 1.521 | OCH₂CH₂F | — | H | H1 | |
| 1.522 | OCH(CH₃)CF₃ | — | H | H1 | |
| 1.523 | OCH(CH₃)CF₃ | — | Na | H1 | |
| 1.524 | OCH(CH₃)CF₃ | 5-CH₃ | H | H1 | |
| 1.525 | OCH(CH₃)CF₃ | — | H | H2 | * |
| 1.526 | OCH(CH₃)CF₃ | — | H | H3 | * |
| 1.527 | OCH(CH₃)CF₃ | — | H | H4 | * |
| 1.528 | OCH(CH₃)CF₃ | — | H | H5 | |
| 1.529 | OCH(CH₃)CF₃ | — | H | H6 | * |
| 1.530 | OCH(CH₃)CF₃ | — | Na | H6 | |
| 1.531 | OCH(CH₃)CF₃ | 5-CH₃ | H | H6 | |
| 1.532 | OCH(CH₃)CF₃ | — | H | H7 | * |
| 1.533 | OCH(CH₃)CF₃ | — | Na | H7 | |
| 1.534 | OCH(CH₃)CF₃ | 5-CH₃ | H | H7 | |
| 1.535 | OCH(CH₃)CF₃ | — | H | H8 | * |
| 1.536 | OCH(CH₃)CF₃ | — | H | H11 | |
| 1.537 | OCH(CH₃)CF₃ | — | H | H13 | |
| 1.538 | OCH(CH₃)CF₃ | — | H | H14 | |
| 1.539 | OCH(CH₃)CF₃ | — | H | H15 | |
| 1.540 | OCH(CH₃)CF₃ | — | H | H16 | |
| 1.541 | OCH(CH₃)CF₃ | — | H | H17 | |
| 1.542 | OCH(CH₃)CHF₂ | — | H | H1 | |

TABLE 1-continued

Compounds of the formula (I-a)

| | R | R¹ | M | Het | ¹H NMR |
|---|---|---|---|---|---|
| 1.543 | OCH(CH₃)CH₂F | — | H | H1 | |
| 1.544 | OCH₂CF₂CF₃ | — | H | H1 | * |
| 1.545 | OCH₂CF₂CF₃ | — | Na | H1 | |
| 1.546 | OCH₂CF₂CF₃ | 5-CH₃ | H | H1 | |
| 1.547 | OCH₂CF₂CF₃ | — | H | H1 | |
| 1.548 | OCH₂CF₂CF₃ | — | H | H2 | |
| 1.549 | OCH₂CF₂CF₃ | — | H | H3 | * |
| 1.550 | OCH₂CF₂CF₃ | — | H | H4 | * |
| 1.551 | OCH₂CF₂CF₃ | — | H | H5 | |
| 1.552 | OCH₂CF₂CF₃ | — | H | H6 | * |
| 1.553 | OCH₂CF₂CF₃ | — | Na | H6 | |
| 1.554 | OCH₂CF₂CF₃ | 5-CH₃ | H | H6 | |
| 1.555 | OCH₂CF₂CF₃ | — | H | H7 | * |
| 1.556 | OCH₂CF₂CF₃ | — | Na | H7 | |
| 1.557 | OCH₂CF₂CF₃ | 5-CH₃ | H | H7 | |
| 1.558 | OCH₂CF₂CF₃ | — | H | H8 | * |
| 1.559 | OCH₂CF₂CF₃ | — | H | H11 | |
| 1.560 | OCH₂CF₂CF₃ | — | H | H13 | |
| 1.561 | OCH₂CF₂CF₃ | — | H | H14 | |
| 1.562 | OCH₂CF₂CF₃ | — | H | H15 | |
| 1.563 | OCH₂CF₂CF₃ | — | H | H16 | |
| 1.564 | OCH₂CF₂CHF₂ | — | H | H17 | |
| 1.565 | OCH₂CF₂CH₂F | — | H | H1 | |
| 1.566 | OCH(CH₃)CF₂CF₃ | — | H | H1 | |
| 1.567 | OCH(CH₃)CF₂CHF₂ | — | H | H1 | |
| 1.568 | OCH(CH₃)CF₂CH₂F | — | H | H1 | |
| 1.569 | OCH₂CHFCF₃ | — | H | H1 | |
| 1.570 | O(CH₂)₂CF₃ | — | H | H1 | |
| 1.571 | O(CH₂)₂CHF₂ | — | H | H1 | |
| 1.572 | O(CH₂)₃CF₃ | — | H | H1 | |
| 1.573 | O(CH₂)₃CHF₂ | — | H | H1 | |
| 1.574 | OCF=CH₂ | — | H | H1 | |
| 1.575 | OCH=CF₂ | — | H | H1 | |
| 1.576 | OCF₂CH=CH₂ | — | H | H1 | |
| 1.577 | OCHFCH=CH₂ | — | H | H1 | |
| 1.578 | OCH=CHCF₃ | — | H | H1 | * |
| 1.579 | SCH₃ | — | H | H1 | |
| 1.580 | SCH₃ | — | H | H2 | |
| 1.581 | SCH₃ | — | H | H3 | * |
| 1.582 | SCH₃ | — | H | H4 | * |
| 1.583 | SCH₃ | — | H | H5 | |
| 1.584 | SCH₃ | — | H | H6 | * |
| 1.585 | SCH₃ | — | H | H7 | * |
| 1.586 | SCH₃ | — | H | H8 | * |
| 1.587 | SCH₃ | — | H | H11 | |
| 1.588 | SCH₃ | — | H | H13 | |
| 1.589 | SCH₃ | — | H | H14 | |
| 1.590 | SCH₃ | — | H | H15 | |
| 1.591 | SCH₃ | — | H | H16 | |
| 1.592 | SCH₃ | — | H | H17 | |
| 1.593 | SCH₂CH₃ | — | H | H1 | |
| 1.594 | SCH₂CH₃ | — | H | H2 | |
| 1.595 | SCH₂CH₃ | — | H | H3 | |
| 1.596 | SCH₂CH₃ | — | H | H4 | |
| 1.597 | SCH₂CH₃ | — | H | H5 | |
| 1.598 | SCH₂CH₃ | — | H | H6 | |
| 1.599 | SCH₂CH₃ | — | H | H7 | |
| 1.600 | SCH₂CH₃ | — | H | H8 | |
| 1.601 | S(CH₂)₂CH₃ | — | H | H1 | |
| 1.602 | SCH(CH₃)₂ | — | H | H1 | |
| 1.603 | SC(CH₃)₃ | — | H | H1 | |
| 1.604 | SCH₂Ph | — | H | H1 | |
| 1.605 | SPh | — | H | H1 | |
| 1.606 | SCF₃ | — | H | H1 | |
| 1.607 | SCF₃ | — | H | H2 | |
| 1.608 | SCF₃ | — | H | H6 | |
| 1.609 | SCF₃ | — | H | H7 | |
| 1.610 | SCHF₂ | — | H | H1 | |
| 1.611 | SCHF₂ | — | H | H2 | |
| 1.612 | SCHF₂ | — | H | H6 | |
| 1.613 | SCHF₂ | — | H | H7 | |
| 1.614 | SCH₂F | — | H | H1 | |
| 1.615 | SCH=CH₂ | — | H | H1 | |
| 1.616 | SCH₂CH=CH₂ | — | H | H1 | |
| 1.617 | SCH₂CH=CH₂ | — | H | H2 | |
| 1.618 | SCH₂CH=CH₂ | — | H | H6 | |
| 1.619 | SCH₂CH=CH₂ | — | H | H7 | |
| 1.620 | SC≡CH | — | H | H1 | |
| 1.621 | SCH₂C≡CH | — | H | H1 | |
| 1.622 | SCH₂C≡CH | — | H | H2 | |
| 1.623 | SCH₂C≡CH | — | H | H6 | |
| 1.624 | SCH₂C≡CH | — | H | H7 | |
| 1.625 | S-cyclopropyl | — | H | H1 | |
| 1.626 | SCH₂-cyclopropyl | — | H | H1 | |
| 1.627 | SCH₂-cyclopropyl | — | H | H2 | |
| 1.628 | SCH₂-cyclopropyl | — | H | H6 | |
| 1.629 | SCH₂-cyclopropyl | — | H | H7 | |
| 1.630 | SF₅ | — | H | H1 | |
| 1.631 | S(O)CH₃ | — | H | H1 | |
| 1.632 | S(O)CH₃ | — | H | H2 | |
| 1.633 | S(O)CH₃ | — | H | H3 | |
| 1.634 | S(O)CH₃ | — | H | H4 | |
| 1.635 | S(O)CH₃ | — | H | H5 | |
| 1.636 | S(O)CH₃ | — | H | H6 | |
| 1.637 | S(O)CH₃ | — | H | H7 | |
| 1.638 | S(O)CH₃ | — | H | H8 | |
| 1.639 | S(O)CH₂CH₃ | — | H | H1 | |
| 1.640 | S(O)CH₂CH₃ | — | H | H2 | |
| 1.641 | S(O)CH₂CH₃ | — | H | H3 | |
| 1.642 | S(O)CH₂CH₃ | — | H | H4 | |
| 1.643 | S(O)CH₂CH₃ | — | H | H5 | |
| 1.644 | S(O)CH₂CH₃ | — | H | H6 | |
| 1.645 | S(O)CH₂CH₃ | — | H | H7 | |
| 1.646 | S(O)CH₂CH₃ | — | H | H8 | |
| 1.647 | S(O)(CH₂)₂CH₃ | — | H | H1 | |
| 1.648 | S(O)CH(CH₃)₂ | — | H | H1 | |
| 1.649 | S(O)C(CH₃)₃ | — | H | H1 | |
| 1.650 | S(O)CH₂Ph | — | H | H1 | |
| 1.651 | S(O)Ph | — | H | H1 | |
| 1.652 | S(O)CF₃ | — | H | H1 | |
| 1.653 | S(O)CHF₂ | — | H | H1 | |
| 1.654 | S(O)CH₂F | — | H | H1 | |
| 1.655 | S(O)CH=CH₂ | — | H | H1 | |
| 1.656 | S(O)CH₂CH=CH₂ | — | H | H1 | |
| 1.657 | S(O)C≡CH | — | H | H1 | |
| 1.658 | S(O)CH₂C≡CH | — | H | H1 | |
| 1.659 | S(O)-cyclopropyl | — | H | H1 | |
| 1.660 | S(O)CH₂-cyclopropyl | — | H | H1 | |
| 1.661 | SO₂CH₃ | — | H | H1 | |
| 1.662 | SO₂CH₃ | — | H | H2 | |
| 1.663 | SO₂CH₃ | — | H | H3 | |
| 1.664 | SO₂CH₃ | — | H | H4 | |
| 1.665 | SO₂CH₃ | — | H | H5 | |
| 1.666 | SO₂CH₃ | — | H | H6 | |
| 1.667 | SO₂CH₃ | — | H | H7 | |
| 1.668 | SO₂CH₃ | — | H | H8 | |
| 1.669 | SO₂CH₃ | — | H | H11 | |
| 1.670 | SO₂CH₃ | — | H | H13 | |
| 1.671 | SO₂CH₃ | — | H | H14 | |
| 1.672 | SO₂CH₃ | — | H | H15 | |
| 1.673 | SO₂CH₃ | — | H | H16 | |
| 1.674 | SO₂CH₃ | — | H | H17 | |

TABLE 1-continued

Compounds of the formula (I-a)

(I-a)

| | R | R¹ | M | Het | ¹H NMR |
|---|---|---|---|---|---|
| 1.675 | SO₂CH₂CH₃ | — | H | H1 | |
| 1.676 | SO₂CH₂CH₃ | — | H | H2 | |
| 1.677 | SO₂CH₂CH₃ | — | H | H3 | |
| 1.678 | SO₂CH₂CH₃ | — | H | H4 | |
| 1.679 | SO₂CH₂CH₃ | — | H | H5 | |
| 1.680 | SO₂CH₂CH₃ | — | H | H6 | |
| 1.681 | SO₂CH₂CH₃ | — | H | H7 | |
| 1.682 | SO₂CH₂CH₃ | — | H | H8 | |
| 1.683 | SO₂(CH₂)₂CH₃ | — | H | H1 | |
| 1.684 | SO₂CH(CH₃)₂ | — | H | H1 | |
| 1.685 | SO₂C(CH₃)₃ | — | H | H1 | |
| 1.686 | SO₂CH₂Ph | — | H | H1 | |
| 1.687 | SO₂Ph | — | H | H1 | |
| 1.688 | SO₂CF₃ | — | H | H1 | |
| 1.689 | SO₂CF₃ | — | H | H2 | |
| 1.690 | SO₂CF₃ | — | H | H6 | |
| 1.691 | SO₂CF₃ | — | H | H7 | |
| 1.692 | SO₂CHF₂ | — | H | H1 | |
| 1.693 | SO₂CH₂F | — | H | H1 | |
| 1.694 | SO₂CH=CH₂ | — | H | H1 | |
| 1.695 | SO₂CH₂CH=CH₂ | — | H | H1 | |
| 1.696 | SO₂CH₂CH=CH₂ | — | H | H2 | |
| 1.697 | SO₂CH₂CH=CH₂ | — | H | H6 | |
| 1.698 | SO₂CH₂CH=CH₂ | — | H | H7 | |
| 1.699 | SO₂C≡CH | — | H | H1 | |
| 1.700 | SO₂CH₂C≡CH | — | H | H1 | |
| 1.701 | SO₂CH₂C≡CH | — | H | H2 | |
| 1.702 | SO₂CH₂C≡CH | — | H | H6 | |
| 1.703 | SO₂CH₂C≡CH | — | H | H7 | |
| 1.704 | SO₂-cyclopropyl | — | H | H1 | |
| 1.705 | SO₂-cyclopropyl | — | H | H2 | |
| 1.706 | SO₂-cyclopropyl | — | H | H6 | |
| 1.707 | SO₂-cyclopropyl | — | H | H7 | |
| 1.708 | SO₂CH₂-cyclopropyl | — | H | H1 | |
| 1.709 | SO₂NHCH₃ | — | H | H1 | |
| 1.710 | SO₂N(CH₃)₂ | — | H | H1 | |
| 1.711 | OSO₂CH₃ | — | H | H1 | * |
| 1.712 | OSO₂CH₃ | — | H | H2 | * |
| 1.713 | OSO₂CH₃ | — | H | H3 | * |
| 1.714 | OSO₂CH₃ | — | H | H4 | |
| 1.715 | OSO₂CH₃ | — | H | H5 | * |
| 1.716 | OSO₂CH₃ | — | H | H6 | |
| 1.717 | OSO₂CH₃ | — | H | H7 | * |
| 1.718 | OSO₂CH₃ | — | H | H8 | * |
| 1.719 | OSO₂CH₃ | — | H | H11 | |
| 1.720 | OSO₂CH₃ | — | H | H15 | |
| 1.721 | OSO₂CH₃ | — | H | H16 | |
| 1.722 | OSO₂CH₂CH₃ | — | H | H1 | |
| 1.723 | OSO₂CH(CH₃)₂ | — | H | H1 | |
| 1.724 | OSO₂C(CH₃)₃ | — | H | H1 | |
| 1.725 | OSO₂CH₂Ph | — | H | H1 | |
| 1.726 | OSO₂CF₃ | — | H | H1 | |
| 1.727 | OSO₂CF₃ | — | H | H2 | |
| 1.728 | OSO₂CF₃ | — | H | H6 | |
| 1.729 | OSO₂CF₃ | — | H | H7 | |
| 1.730 | OSO₂CHF₂ | — | H | H1 | |
| 1.731 | OSO₂CHF₂ | — | H | H2 | |
| 1.732 | OSO₂CHF₂ | — | H | H6 | |
| 1.733 | OSO₂CHF₂ | — | H | H7 | |
| 1.734 | OSO₂CH₂F | — | H | H1 | |
| 1.735 | OSO₂CH₂CF₃ | — | H | H1 | |
| 1.736 | OSO₂CH₂CHF₂ | — | H | H1 | |
| 1.737 | OSO₂(CH₂)₂F | — | H | H1 | |
| 1.738 | OSO₂CH=CH₂ | — | H | H1 | |
| 1.739 | OSO₂CH₂CH=CH₂ | — | H | H1 | |
| 1.740 | OSO₂C≡CH | — | H | H1 | |
| 1.741 | OSO₂CH₂C≡CH | — | H | H1 | |
| 1.742 | OSO₂-cyclopropyl | — | H | H1 | |
| 1.743 | OSO₂CH₂-cyclopropyl | — | H | H1 | |
| 1.744 | OSO₂CH₂CN | — | H | H1 | |
| 1.745 | OSO₂CH₂CN | — | H | H2 | |
| 1.746 | OSO₂CH₂CN | — | H | H6 | |
| 1.747 | OSO₂CH₂CN | — | H | H7 | |
| 1.748 | OSO₂NHCH₃ | — | H | H1 | |
| 1.749 | OSO₂N(CH₃)₂ | — | H | H1 | * |
| 1.750 | OSO₂N(CH₃)₂ | — | H | H2 | * |
| 1.751 | OSO₂N(CH₃)₂ | — | H | H3 | * |
| 1.752 | OSO₂N(CH₃)₂ | — | H | H4 | |
| 1.753 | OSO₂N(CH₃)₂ | — | H | H5 | |
| 1.754 | OSO₂N(CH₃)₂ | — | H | H6 | * |
| 1.755 | OSO₂N(CH₃)₂ | — | H | H7 | * |
| 1.756 | OSO₂N(CH₃)₂ | — | H | H8 | * |
| 1.757 | OSO₂N(CH₃)₂ | — | H | H11 | |
| 1.758 | OSO₂N(CH₃)₂ | — | H | H15 | |
| 1.759 | OSO₂N(CH₃)₂ | — | H | H16 | |
| 1.760 | OSO₂NHCH=CH₂ | — | H | H1 | |
| 1.761 | OSO₂NHCH₂C≡CH | — | H | H1 | |
| 1.762 | OSO₂NHCF₃ | — | H | H1 | |
| 1.763 | OSO₂NHCF₃ | — | H | H2 | |
| 1.764 | OSO₂NHCF₃ | — | H | H6 | |
| 1.765 | OSO₂NHCF₃ | — | H | H7 | |
| 1.766 | OSO₂NHCHF₂ | — | H | H1 | |
| 1.767 | OSO₂NHCHF₂ | — | H | H2 | |
| 1.768 | OSO₂NHCHF₂ | — | H | H6 | |
| 1.769 | OSO₂NHCHF₂ | — | H | H7 | |
| 1.770 | OSO₂NHCH₂F | — | H | H1 | |
| 1.771 | OC(O)H | — | H | H1 | |
| 1.772 | OC(O)CH₃ | — | H | H1 | |
| 1.773 | OC(O)CH₂CH₃ | — | H | H1 | |
| 1.774 | OC(O)OCH₃ | — | H | H1 | |
| 1.775 | OC(O)OCH₂CH₃ | — | H | H1 | |
| 1.776 | OC(O)NH₂ | — | H | H1 | |
| 1.777 | OC(O)NHCH₃ | — | H | H1 | |
| 1.778 | OC(O)N(CH₃)₂ | — | H | H1 | |
| 1.779 | OC(O)N(CH₂CH₃)₂ | — | H | H1 | |
| 1.780 | Si(CH₃)₃ | — | H | H1 | |
| 1.781 | 2-thienyl | — | H | H1 | |
| 1.782 | 3-thienyl | — | H | H1 | |
| 1.783 | 2-pyridyl | — | H | H1 | |
| 1.784 | 3-pyridyl | H | H1 | | |
| 1.785 | 4-pyridyl | H | H1 | | |
| 1.786 | OH | H | H1 | | |
| 1.787 | C(O)H | — | H | H1 | |
| 1.788 | C(O)H | — | H | H2 | |
| 1.789 | C(O)H | — | H | H6 | |
| 1.790 | C(O)H | — | H | H7 | |
| 1.791 | C(O)CH₃ | — | H | H1 | |
| 1.792 | C(O)CH₃ | — | H | H2 | |
| 1.793 | C(O)CH₃ | — | H | H6 | |
| 1.794 | C(O)CH₃ | — | H | H7 | |
| 1.795 | C(O)OCH₃ | — | H | H1 | |
| 1.796 | C(O)OCH₃ | — | H | H2 | |
| 1.797 | C(O)OCH₃ | — | H | H6 | |
| 1.798 | C(O)OCH₃ | — | H | H7 | |
| 1.799 | C(O)OCH₂CH₃ | — | H | H1 | |
| 1.800 | C(O)OCH₂CH₂CH₃ | — | H | H1 | |
| 1.801 | C(O)OCH(CH₃)₂ | — | H | H1 | |
| 1.802 | C(O)OC(CH₃)₃ | — | H | H1 | |
| 1.803 | C(O)NH₂ | — | H | H1 | |
| 1.804 | C(O)N(CH₃)₂ | — | H | H1 | |
| 1.805 | C(O)N(CH₃)₂ | — | H | H2 | |
| 1.806 | C(O)N(CH₃)₂ | — | H | H6 | |

TABLE 1-continued

Compounds of the formula (I-a)

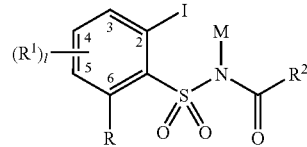

(I-a)

| | R | R¹ | M | Het | ¹H NMR |
|---|---|---|---|---|---|
| 1.807 | C(O)N(CH₃)₂ | — | H | H1 | |
| 1.808 | C(O)N(CH₂CH₃)₂ | — | H | H1 | |
| 1.809 | C(O)NHCH₃ | — | H | H1 | |
| 1.810 | C(O)NHCH₂CH₃ | — | H | H1 | |
| 1.811 | C(O)NH-cyclopropyl | — | H | H1 | |
| 1.812 | C(O)NH-cyclopropyl | — | H | H2 | |
| 1.813 | C(O)N H-cyclopropyl | — | H | H6 | |
| 1.814 | C(O)NH-cyclopropyl | — | H | H1 | |
| 1.815 | CH₃ | H | H | H10 | * |
| 1.816 | OCH₃ | 3-Cl | H | H1 | * |
| 1.817 | OCH₃ | 3-Cl | H | H2 | * |
| 1.818 | OCH₃ | 3-Cl | H | H3 | * |
| 1.819 | OCH₃ | 3-Cl | H | H4 | * |
| 1.820 | OCH₃ | 3-Cl | H | H6 | * |
| 1.821 | OCH₃ | 3-Cl | H | H1 | * |
| 1.822 | OCH₃ | 3-Cl | H | H8 | * |
| 1.823 | H | 4-F | H | H1 | * |
| 1.824 | H | 4-F | H | H3 | * |
| 1.825 | H | 4-F | H | H6 | * |
| 1.826 | H | 4-F | H | H1 | * |
| 1.827 | H | 4-F | H | H8 | * |
| 1.828 | H | 3-Cl | H | H1 | * |
| 1.829 | H | 3-Cl | H | H2 | * |
| 1.830 | H | 3-Cl | H | H3 | * |
| 1.831 | H | 3-Cl | H | H4 | * |
| 1.832 | H | 3-Cl | H | H6 | * |
| 1.833 | H | 3-Cl | H | H7 | * |
| 1.834 | H | 3-Cl | H | H8 | * |
| 1.835 | H | 5-CF₃ | H | H1 | * |
| 1.836 | H | 5-CF₃ | H | H2 | * |
| 1.837 | H | 5-CF₃ | H | H3 | * |
| 1.838 | H | 5-CF₃ | H | H4 | * |
| 1.839 | H | 5-CF₃ | H | H6 | * |
| 1.840 | H | 5-CF₃ | H | H7 | * |
| 1.841 | H | 5-CF₃ | H | H8 | * |
| 1.842 | Cl | 4-CF₃ | H | H1 | * |
| 1.843 | Cl | 4-CF₃ | H | H2 | * |
| 1.844 | Cl | 4-CF₃ | H | H3 | * |
| 1.845 | Cl | 4-CF₃ | H | H4 | * |
| 1.846 | Cl | 4-CF₃ | H | H6 | * |
| 1.847 | Cl | 4-CF₃ | H | H7 | * |
| 1.848 | Cl | 4-CF₃ | H | H8 | * |
| 1.849 | Cl | 3-Cl | H | H1 | * |
| 1.850 | Cl | 3-Cl | H | H2 | * |
| 1.851 | Cl | 3-Cl | H | H3 | * |
| 1.852 | Cl | 3-Cl | H | H4 | * |
| 1.853 | Cl | 3-Cl | H | H6 | * |
| 1.854 | Cl | 3-Cl | H | H7 | * |
| 1.855 | H | 3-F, 4-CH₃ | H | H1 | * |
| 1.856 | H | 3-F, 4-CH₃ | H | H2 | * |
| 1.857 | H | 3-F, 4-CH₃ | H | H3 | * |
| 1.858 | H | 3-F, 4-CH₃ | H | H4 | * |
| 1.859 | H | 3-F, 4-CH₃ | H | H6 | * |
| 1.860 | H | 3-F, 4-CH₃ | H | H7 | * |
| 1.861 | H | 3-F, 4-CH₃ | H | H8 | * |
| 1.862 | H | 4-CH₃, 5-CH₃ | H | H1 | * |
| 1.863 | H | 4-CH₃, 5-CH₃ | H | H2 | * |
| 1.864 | H | 4-CH₃, 5-CH₃ | H | H3 | * |
| 1.865 | H | 4-CH₃, 5-CH₃ | H | H4 | * |
| 1.866 | H | 4-CH₃, 5-CH₃ | H | H6 | * |
| 1.867 | H | 4-CH₃, 5-CH₃ | H | H7 | * |
| 1.868 | H | 4-CH₃, 5-CH₃ | H | H8 | * |
| 1.869 | H | 4-Cl | H | H1 | * |
| 1.870 | H | 4-Cl | H | H2 | * |
| 1.871 | H | 4-Cl | H | H3 | * |
| 1.872 | H | 4-Cl | H | H4 | * |

TABLE 1-continued

Compounds of the formula (I-a)

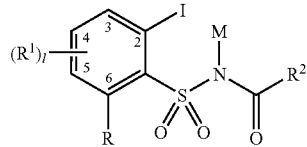

(I-a)

| | R | R¹ | M | Het | ¹H NMR |
|---|---|---|---|---|---|
| 1.873 | H | 4-Cl | H | H6 | * |
| 1.874 | H | 4-Cl | H | H7 | * |
| 1.875 | H | 4-Cl | H | H8 | * |
| 1.876 | H | 4-(CH₂)₂CH₃ | H | H1 | * |
| 1.877 | H | 4-(CH₂)₂CH₃ | H | H2 | * |
| 1.878 | H | 4-(CH₂)₂CH₃ | H | H3 | * |
| 1.879 | H | 4-(CH₂)₂CH₃ | H | H4 | * |
| 1.880 | H | 4-(CH₂)₂CH₃ | H | H6 | * |
| 1.881 | H | 4-(CH₂)₂CH₃ | H | H7 | * |
| 1.882 | H | 4-(CH₂)₂CH₃ | H | H8 | * |
| 1.883 | H | 4-(CH₂)₃CH₃ | H | H2 | * |
| 1.884 | H | 4-(CH₂)₃CH₃ | H | H3 | * |
| 1.885 | H | 4-(CH₂)₃CH₃ | H | H1 | * |
| 1.886 | H | 4-(CH₂)₃CH₃ | H | H6 | * |
| 1.887 | H | 4-(CH₂)₃CH₃ | H | H7 | * |
| 1.888 | H | 4-(CH₂)₃CH₃ | H | H8 | * |
| 1.889 | H | 4-(CH₂)₃CH₃ | H | H4 | * |
| 1.890 | H | 4-CF₃ | H | H2 | * |
| 1.891 | H | 4-CF₃ | H | H7 | * |
| 1.892 | H | 4-CF₃ | H | H10 | * |
| 1.893 | H | 4-CF₃ | H | H1 | * |
| 1.894 | H | 4-CF₃ | H | H3 | * |
| 1.895 | H | 4-CF₃ | H | H4 | * |
| 1.896 | H | 4-CF₃ | H | H6 | * |
| 1.897 | H | 4-CF₃ | H | H8 | * |

¹H NMR data for compounds of table 1:

Example 1.001 (d₆-DMSO): 8.20 (dd, J=1.5, 8.0, 1H); 8.17 (dd, J=1.1, 7.9, 1H); 7.67 (td, J=1.2, 7.5, 1H); 7.41 (td, J=1.6, 7.6, 1H); 3.98 (s, 3H); 3.06 (s, 3H).

Example 1.004 (d₆-DMSO): 8.19 (m, 2H); 7.67 (td, J=1.2, 7.5, 1H); 7.41 (td, J=1.6, 7.6, 1H); 4.36 (q, J=7.1, 2H); 3.05 (s, 3H); 1.35 (t, 3H).

Example 1.005 (d₆-DMSO): 8.18 (m, 2H); 7.67 (td, J=1.2, 7.5, 1H); 7.41 (td, J=1.6, 7.6, 1H); 4.27 (t, J=6.5, 2H); 3.06 (s, 3H); 1.74 (m, 2H); 0.94 (t, J=7.4, 3H).

Example 1.008 (d₆-DMSO): 8.17 (m, 2H); 7.66 (td, J=1.2, 7.5, 1H); 7.4 (td, J=1.6, 7.6, 1H); 3.96 (s, 3H); 2.75 (m, 1H); 0.90 (m, 4H).

Example 1.011 (d₆-DMSO): 8.19 (m, 2H); 7.67 (td, J=1.3, 7.5, 1H); 7.42 (td, J=1.6, 7.5, 1H); 4.34 (q, J=7.1, 2H); 2.75 (m, 1H); 1.35 (t, J=7.1, 3H); 0.91 (m, 4H).

Example 1.014 (d₆-DMSO): 8.21 (dd, J=1.5, 5.5, 1H); 8.18 (dd, J=1.6, 5.4, 1H); 7.68 (dd, J=1.2, 7.5, 1H); 7.42 (dd, J=1.6, 7.6, 1H); 4.25 (t=6.4, 2H); 2.76 (m, 1H); 1.74 (m, 2H); 0.93 (m, 7H).

Example 1.021 (CDCl₃): 7.88 (m, 1H); 7.15 (m, 2H); 4.00 (s, 3H); 3.13 (s, 3H).

Example 1.022 (CDCl₃): 11.00 (br s, 1H); 7.94 (m, 1H); 7.20 (m, 2H); 4.45 (q, J=7.1, 2H); 3.20 (s, 3H); 1.43 (t, J=7.1, 3H).

Example 1.023 (CDCl₃): 7.94 (m, 1H); 7.20 (m, 2H); 4.34 (t, J=6.7, 2H); 3.20 (s, 3H); 1.82 (m, 2H); 0.99 (t, J=7.4, 3H).

Example 1.024 (CDCl₃): 11.01 (br s, 1H); 7.94 (m, 1H); 7.20 (m, 2H); 5.16 (m, 1H); 3.17 (s, 3H); 1.40 (d, J=6.2, 6H).

Example 1.027 (CDCl₃): 11.03 (br s, 1H); 7.94 (m, 1H); 7.20 (m, 2H); 4.43 (q, J=7.1, 2H); 2.73 (m, 1H); 1.43 (t, J=7.1, 3H); 1.03 (m, 4H).

Example 1.028 (CDCl$_3$): 11.02 (br s, 1H); 7.93 (m, 1H); 7.19 (m, 2H); 4.32 (t, J=6.5, 2H); 2.74 (m, 1H); 1.81 (m, 2H); 1.02 (m, 4H); 1.00 (t, J=7.4, 3H).

Example 1.037 (CDCl$_3$): 11.00 (br s, 1H); 8.00 (dd, J=0.7, 7.5, 1H); 7.31 (br d, J=7.5, 1H); 7.04 (t, J=7.8, 1H); 4.07 (s, 3H); 3.21 (s, 3H); 2.89 (s, 3H).

Example 1.038 (CDCl$_3$): 11.03 (br s, 1H); 8.00 (d, J=7.8, 1H); 7.30 (d, J=7.5, 1H); 7.04 (t, J=7.5, 1H); 4.45 (q, J=7.2, 1H); 3.20 (s, 3H); 2.89 (s, 3H); 1.43 (t, J=7.2, 3H).

Example 1.039 (CDCl$_3$): 11.02 (br s, 1H); 8.00 (br d, J=7.8, 1H); 7.30 (br d, J=7.5, 1H); 7.03 (t, J=7.8, 1H); 4.34 (t, J=6.5, 1H); 3.20 (s, 3H); 2.89 (s, 3H); 1.81 (m, 2H); 0.99 (t, J=7.5, 3H).

Example 1.040 (CDCl$_3$): 11.06 (br s, 1H); 8.00 (dd, J=0.7, 7.8, 1H); 7.30 (br d, J=7.8, 1H); 7.04 (t, J=7.8, 1H); 5.16 (m, 1H); 3.17 (s, 3H); 2.89 (s, 3H); 1.40 (d, J=6.2, 6H).

Example 1.042 (CDCl$_3$): 11.03 (br s, 1H); 8.00 (dd, J=0.7, 7.8, 1H); 7.30 (br d, J=7.5, 1H); 7.03 (t, J=7.8, 1H); 4.06 (s, 3H); 2.88 (s, 3H); 2.74 (m, 1H); 1.03 (m, 4H).

Example 1.043 (CDCl$_3$): 11.07 (br s, 1H); 8.00 (dd, J=1.0, 7.8, 1H); 7.30 (br d, J=7.5, 1H); 7.03 (t, J=7.5, 1H); 4.43 (q, J=6.8, 2H); 2.88 (s, 3H); 2.74 (m, 1H); 1.43 (t, J=7.2, 3H); 1.03 (m, 4H).

Example 1.044 (CDCl$_3$): 11.05 (br s, 1H); 7.99 (dd, J=0.7, 7.8, 1H); 7.30 (dd, J=0.7, 7.8, 1H); 7.03 (t, J=7.8, 1H); 4.32 (t, J=6.5, 2H); 2.88 (s, 3H); 2.74 (m, 1H); 1.81 (m, 2H); 1.03 (m, 4H); 1.00 (t, J=7.5, 3H).

Example 1.133 (CDCl$_3$): 11.17 (br s, 1H); 8.37 (dd, J=1.2, 8.0, 1H); 7.97 (br d, J=8.0, 1H); 7.29 (t, J=8.0, 1H); 4.06 (s, 3H); 3.21 (s, 3H).

Example 1.136 (CDCl$_3$): 11.19 (br s, 1H); 8.37 (dd, J=1.1, 7.9, 1H); 7.96 (br d, J=7.9, 1H); 7.29 (br t, J=7.7, 1H); 4.44 (m, 2H); 3.21 (s, 3H); 1.42 (t, J=7.1, 3H).

Example 1.137 (CDCl$_3$): 11.17 (br s, 1H); 8.36 (dd, J=1.2, 8.0, 1H); 7.95 (br d, J=8.0, 1H); 7.28 (br t, J=8.0, 1H); 4.33 (t, J=6.7, 2H); 3.21 (s, 3H); 1.81 (m, 2H); 0.98 (t, J=7.4, 3H).

Example 1.138 (CDCl$_3$): 11.24 (br s, 1H); 8.37 (dd, J=1.2, 8.0, 1H); 7.96 (dd, J=0.7, 8.0, 1H); 7.29 (td, 0.7, 8.0, 1H); 5.15 (m, 1H); 3.18 (s, 3H); 1.39 (d, J=6.2, 6H).

Example 1.140 (CDCl$_3$): 11.19 (br s, 1H); 8.36 (dd, J=1.2, 8.0, 1H); 7.96 (br dd, J=0.6, 8.0, 1H); 7.28 (td, J=0.7, 8.1, 1H); 4.05 (s, 3H); 2.75 (m, 1H); 1.04 (m, 4H).

Example 1.143 (CDCl$_3$): 11.23 (br s, 1H); 8.36 (dd, J=1.2, 8.0, 1H); 7.96 (dd, J=0.6, 8.0, 1H); 7.28 (t, J=8.0, 1H); 4.42 (q, J=7.1, 2H); 2.74 (m, 1H); 1.42 (t, J=7.1, 3H); 1.04 (m, 4H).

Example 1.191 (CDCl$_3$): 10.76 (br s, 1H); 7.81 (dd, J=1.1, 7.8, 1H); 7.11 (t, J=84.4, 1H); 7.00 (dd, J=1.2, 8.3, 1H); 4.07 (s, 3H); 3.93 (s, 3H); 3.19 (s, 3H).

Example 1.194 (d$_6$-DMSO): 7.82 (m, 1H); 7.31 (m, 2H); 4.37 (q, J=7.2, 2H); 3.86 (s, 3H); 3.05 (s, 3H); 1.38 (t, J=7.2, 3H).

Example 1.195 (CDCl$_3$): 10.78 (br s, 1H); 7.81 (dd, J=0.8, 8.0, 1H); 7.11 (t, J=8.0, 1H); 6.99 (dd, J=0.8, 8.0, 1H); 4.33 (t, J=7.2, 2H); 3.94 (s, 3H); 3.19 (s, 3H); 1.81 (m, 2H); 0.99 (t, J=7.2, 3H).

Example 1.196 (CDCl$_3$): 10.77 (br s, 1H); 7.79 (dd, J=0.8, 7.9, 1H); 7.09 (t, J=8.1, 1H); 6.99 (dd, J=0.9, 8.4, 1H); 5.14 (m, 1H); 3.93 (s, 3H); 3.16 (s, 3H); 1.38 (d, J=6.2, 6H).

Example 1.197 (CDCl$_3$): 10.86 (s, 1H); 7.81 (dd, J=1.2, 7.9, 1H); 7.11 (t, J=8.4, 1H); 7.00 (dd, J=1.2, 8.5, 1H); 3.94 (s, 3H); 3.21 (m, 5H); 1.41 (t, J=7.4, 3H).

Example 1.198 (CDCl$_3$): 10.77 (br s, 1H); 7.79 (dd, J=1.1, 7.9, 1H); 7.09 (t, J=8.3, 1H); 7.00 (dd, J=1.0, 8.4, 1H); 4.04 (s, 3H); 3.93 (s, 3H); 2.72 (m, 1H); 1.02 (m, 4H).

Example 1.201 (d$_6$-DMSO): 7.80 (m, 1H); 7.30 (m, 2H); 4.35 (q, J=7.1, 2H); 3.87 (s, 3H); 2.76 (m, 1H); 1.35 (t, J=7.0, 3H); 0.91 (m, 4H).

Example 1.204 (d$_6$-DMSO): 7.80 (m, 1H); 7.29 (m, 2H); 4.25 (t, J=6.4, 2H); 3.87 (s, 3H); 2.77 (m, 1H); 1.75 (m, 2H); 0.94 (m, 7H).

Example 1.211 (d$_6$-DMSO): 7.80 (m, 1H); 7.28 (m, 2H); 4.17 (q, J=7.0, 2H); 3.98 (s, 3H); 3.06 (s, 3H); 1.34 (t, J=6.9, 3H).

Example 1.214 (d$_6$-DMSO): 10.88 (br s, 1H); 7.80 (dd, J=2.2, 6.7, 1H); 7.28 (m, 2H); 4.36 (q, J=7.1, 2H); 4.17 (q, J=7.0, 2H); 3.06 (s, 3H); 1.35 (m, 6H).

Example 1.215 (CDCl$_3$): 10.70 (br s, 1H); 7.79 (dd, J=1.0, 7.6, 1H); 7.07 (t, J=8.3, 1H); 6.97 (dd, J=1.1, 8.4, 1H); 4.33 (t, J=6.6, 2H); 4.16 (q, J=7.0, 2H); 3.19 (s, 3H); 1.81 (m, 2H); 1.51 (t, J=7.0, 3H); 0.98 (t, J=7.4, 3H).

Example 1.218 (CDCl$_3$): 10.69 (br s, 1H); 7.77 (dd, J=1.1, 7.9, 1H); 7.05 (t, J=8.3, 1H); 6.95 (dd, J=1.1, 8.4, 1H); 4.15 (q, J=7.0, 2H); 4.03 (s, 3H); 2.72 (m, 1H); 1.50 (t, J=7.0, 3H); 1.01 (m, 4H).

Example 1.221 (d$_6$-DMSO): 10.92 (br s, 1H), 7.79 (dd, J=2.1, 6.8, 1H); 7.28 (m, 2H); 4.34 (q, J=7.0, 2H); 4.17 (q, J=7.0, 2H); 2.76 (m, 1H); 1.35 (m, 6H), 0.92 (m, 4H).

Example 1.231 (CDCl$_3$): 10.63 (br s, 1H); 7.77 (dd, J=1.1, 8.4, 1H); 7.05 (t, J=8.4, 1H); 6.96 (dd, J=1.1, 8.4, 1H); 4.05 (s, 3H); 4.03 (t, J=6.7, 2H); 3.18 (s, 3H); 1.91 (m, 2H); 1.07 (t, J=7.4, 3H).

Example 1.235 (CDCl$_3$): 10.67 (br s, 1H); 7.79 (dd, J=1.1, 7.8, 1H); 7.07 (t, J=8.3, 1H); 6.98 (dd, J=1.0, 8.4, 1H); 4.33 (t, J=6.7, 2H); 4.04 (t, J=6.6, 2H); 3.19 (s, 3H); 1.91 (m, 2H); 1.80 (m, 2H); 1.07 (t, J=7.4, 3H); 0.98 (t, t, J=7.4, 3H).

Example 1.236 (CDCl$_3$): 10.70 (br s, 1H); 7.79 (br d, J=7.8, 1H); 7.07 (br t, J=7.9, 1H); 6.98 (br d, J=8.4, 1H); 5.15 (m, 1H); 4.04 (t, J=6.6, 2H); 3.16 (s, 3H); 1.91 (m, 2H); 1.38 (d, J=6.2, 6H); 1.07 (t, J=7.5, 3H).

Example 1.237 (CDCl$_3$): 10.76 (br s, 1H); 7.79 (dd, 1.1, 7.9, 1H); 7.06 (m, 2H); 4.04 (t, J=6.6, 2H); 3.20 (s, 3H); 3.07 (q, J=7.4, 2H); 1.92 (m, 2H); 1.40 (t, J=7.4, 3H); 1.10 (t, J=7.4, 3H).

Example 1.238 (CDCl$_3$): 10.66 (br s, 1H); 7.77 (dd, J=1.1, 7.9, 1H); 7.06 (t, J=8.4, 1H); 6.96 (dd, J=1.1, 8.4, 1H); 4.04 (s, 3H); 4.03 (t, J=6.6, 2H); 2.72 (m, 1H); 1.90 (m, 2H); 1.07 (t, J=7.4, 3H); 1.01 (m, 4H).

Example 1.241 (CDCl$_3$): 10.71 (br s, 1H); 7.78 (dd, J=1.1, 7.8, 1H); 7.06 (t, J=8.4, 1H); 6.97 (dd, J=1.1, 8.4, 1H); 4.42 (q, J=7.1, 2H); 4.03 (t, J=6.6, 2H); 2.72 (m, 1H); 1.91 (m, 2H); 1.42 (t, J=7.1, 3H); 1.07 (t, J=7.4, 3H); 1.03 (m, 4H).

Example 1.244 (CDCl$_3$): 10.67 (br s, 1H); 7.76 (dd, J=1.2, 7.8, 1H); 7.04 (t, J=8.4, 1H); 6.95 (dd, J=1.1, 8.4, 1H); 4.30 (t, J=6.5, 2H); 4.02 (t, J=6.6, 2H); 2.72 (m, 1H); 1.91 (m, 2H); 1.80 (m, 2H); 1.07 (t, J=7.4, 3H); 1.04 (m, 4H); 0.99 (t, J=7.4, 3H).

Example 1.251 (CDCl$_3$): 10.62 (br s, 1H); 7.76 (dd, J=1.1, 7.8, 1H); 7.05 (m, 1H); 6.97 (m, 1H); 4.70 (m, 1H); 4.06 (s, 3H); 3.19 (s, 3H); 1.40 (d, J=6.1, 6H).

Example 1.254 (CDCl$_3$): 10.65 (br s, 1H); 7.77 (dd, J=1.1, 7.8, 1H); 7.05 (t, J=7.9, 1H); 6.97 (br d, J=8.4, 1H); 4.70 (m, 1H); 4.43 (q, J=7.1, 2H); 3.18 (s, 3H); 1.42 (t, J=7.1, 3H); 1.40 (d, J=6.1, 6H).

Example 1.255 (CDCl$_3$): 10.65 (br s, 1H); 7.76 (dd, J=1.1, 7.8, 1H); 7.06 (dd, J=7.8, 8.4, 1H); 6.97 (br d, J=8.4, 1H); 4.71 (m, 1H); 4.33 (t, J=6.7, 2H); 3.19 (s, 3H); 1.80 (m, 2H); 1.40 (d, J=6.1, 6H); 0.98 (t, J=7.4, 3H).

Example 1.256 (CDCl$_3$): 10.68 (br s, 1H); 7.77 (br d, J=7.8, 1H); 7.06 (br t, J=8.4, 1H); 6.97 (br d, J=8.4, 1H); 5.15 (m, 1H); 4.71 (m, 1H); 3.16 (br s, 3H); 1.40 (m, 12H).

Example 1.258 (CDCl$_3$): 10.67 (br s, 1H); 7.76 (m, 1H); 7.05 (m, 1H); 6.97 (m, 1H); 4.70 (m, 1H); 4.04 (s, 3H); 2.72 (m, 1H); 1.40 (d, J=6.1, 6H); 0.98 (m, 4H).

Example 1.261 (CDCl$_3$): 10.70 (br s, 1H); 7.76 (dd, J=1.1, 7.8, 1H); 7.06 (t, J=8.4, 1H); 6.97 (br d, J=7.9, 1H); 4.71 (m, 1H); 4.42 (q, J=7.1, 2H); 2.73 (m, 1H); 1.42 (d, J=7.1, 3H); 1.40 (d, J=6.1, 6H); 1.01 (m, 4H).

Example 1.264 (CDCl$_3$): 10.69 (br s, 1H); 7.76 (dd, J=1.0, 7.8, 1H); 7.05 (t, J=8.2, 1H); 6.97 (br d, J=7.9, 1H); 4.71 (m, 1H); 4.31 (t, J=6.6, 2H); 2.73 (m, 1H); 1.80 (m, 2H); 1.40 (d, J=6.1, 6H); 1.02 (m, 4H); 1.00 (t, J=7.4, 3H).

Example 1.273 (CDCl$_3$): 10.65 (br s, 1H); 7.79 (dd, J=1.1, 7.8, 1H); 7.07 (t, J=8.4, 1H); 6.98 (dd, J=1.1, 8.4, 1H); 4.07 (t, J=6.6, 2H); 4.06 (s, 3H); 3.19 (s, 3H); 1.85 (m, 2H); 1.52 (m, 2H); 0.98 (t, J=7.4, 3H).

Example 1.274 (CDCl$_3$): 10.67 (br s, 1H); 7.81 (dd, 1.1, 7.8, 1H); 7.07 (t, J=8.3, 1H); 6.98 (dd, J=1.1, 8.4, 1H); 4.44 (q, J=7.1, 2H); 4.07 (t, J=6.6, 2H); 3.18 (s, 3H); 1.86 (m, 2H); 1.52 (m, 2H); 1.42 (t, J=7.1, 3H); 0.98 (t, J=7.4, 3H).

Example 1.275 (CDCl$_3$): 10.67 (br s, 1H); 7.79 (dd, J=1.1, 7.8, 1H); 7.07 (t, J=8.4, 1H); 6.98 (dd, J=1.1, 8.4, 1H); 4.33 (t, J=6.7, 2H); 4.07 (t, J=6.6, 2H); 3.19 (s, 3H); 1.83 (m, 4H); 1.52 (m, 4H); 0.98 (t, J=7.4, 3H); 0.98 (t, J=7.4, 3H).

Example 1.276 (CDCl$_3$): 10.71 (br s, 1H); 7.79 (dd, J=1.1, 7.8, 1H); 7.07 (t, J=8.4, 1H); 6.98 (dd, J=1.1, 8.4, 1H); 5.15 (m, 1H); 4.08 (t, J=6.6, 2H); 3.16 (s, 3H); 1.86 (m, 2H); 1.52 (m, 2H); 1.39 (d, J=6.2, 6H); 0.98 (t, J=7.4, 3H).

Example 1.278 (CDCl$_3$): 10.70 (br s, 1H); 7.79 (dd, J=1.1, 7.8, 1H); 7.07 (t, J=8.4, 1H); 6.98 (dd, J=1.1, 8.4, 1H); 4.07 (t, J=6.6, 2H); 4.05 (s, 3H); 2.72 (m, 1H); 1.86 (m, 2H); 1.52 (m, 2H); 1.02 (m, 4H); 0.99 (t, J=7.4, 3H).

Example 1.279 (CDCl$_3$): 10.72 (br s, 1H); 7.79 (dd, J=1.1, 7.8, 1H); 7.06 (t, J=8.4, 1H); 6.98 (dd, J=1.1, 8.4, 1H); 4.42 (q, J=7.1, 2H); 4.07 (t, J=6.6, 2H); 2.72 (m, 1H); 1.86 (m, 2H); 1.52 (m, 2H); 1.42 (t, J=7.1, 3H); 1.02 (m, 4H); 0.99 (t, J=7.3, 3H).

Example 1.280 (CDCl$_3$): 10.71 (br s, 1H); 7.79 (dd, J=1.1, 7.8, 1H); 7.06 (t, J=8.4, 1H); 6.98 (dd, J=1.1, 8.4, 1H); 4.31 (t, J=6.6, 2H); 4.07 (t, J=6.6, 2H); 2.73 (m, 1H); 1.83 (m, 4H); 1.52 (m, 2H); 1.01 (m, 10H).

Example 1.281 (CDCl$_3$): 10.60 (br s, 1H); 7.77 (dd, J=1.1, 7.8, 1H); 7.05 (t, J=8.4, 1H); 6.96 (br d, J=8.0, 1H); 4.48 (m, 1H); 4.06 (s, 3H); 3.19 (s, 3H); 1.88 (m, 1H); 1.70 (m, 1H); 1.31 (d, J=6.1, 3H, 0.97 (t, J=7.5, 3H).

Example 1.286 (CDCl$_3$): 10.65 (br s, 1H); 7.76 (dd, J=1.1, 7.8, 1H); 7.05 (t, J=8.3, 1H); 6.96 (br d, J=8.1, 1H); 4.48 (m, 1H); 4.04 (s, 3H); 2.72 (m, 1H); 1.88 (m, 1H); 1.70 (m, 1H); 1.32 (d, J=6.1, 3H); 1.00 (m, 4H); 0.98 (t, J=7.5, 3H).

Example 1.289 (CDCl$_3$): 10.63 (br s, 1H); 7.79 (dd, J=1.1, 7.8, 1H); 7.07 (t, J=8.4, 1H); 6.98 (dd, J=1.1, 8.4, 1H); 4.06 (s, 3H); 3.83 (d, J=6.7, 2H); 3.18 (s, 3H); 2.21 (m, 1H); 1.06 (d, J=6.7, 6H).

Example 1.290 (CDCl$_3$): 10.65 (br s, 1H); 7.79 (dd, J=1.1, 7.8, 1H); 7.07 (t, J=8.4, 1H); 6.97 (dd, J=1.1, 8.4, 1H); 4.43 (q, J=7.1, 2H); 2.83 (d, J=6.7, 2H); 3.18 (s, 3H); 2.22 (m, 1H); 1.42 (t, J=7.1, 3H); 1.07 (d, J=6.7, 6H).

Example 1.294 (CDCl$_3$): 10.67 (br s, 1H); 7.79 (dd, J=1.1, 7.8, 1H); 7.06 (t, J=8.4, 1H); 6.97 (dd, J=1.1, 8.4, 1H); 4.04 (s, 3H); 3.83 (d, J=6.7, 2H); 2.72 (m, 1H); 2.22 (m, 1H); 1.06 (d, J=6.7, 6H); 1.01 (m, 4H).

Example 1.295 (CDCl$_3$): 10.69 (br s, 1H); 7.79 (dd, J=1.1, 7.8, 1H); 7.06 (t, J=8.4, 1H); 6.97 (dd, J=1.1, 8.4, 1H); 4.42 (q, J=7.1, 2H); 3.83 (d, J=6.7, 2H); 2.72 (m, 1H); 2.22 (m, 1H); 1.42 (t, J=7.1, 3H); 1.06 (d, J=6.7, 6H); 1.02 (m, 4H).

Example 1.346 (CDCl$_3$): 10.63 (br s, 1H); 7.73 (dd, J=1.1, 7.9, 1H); 7.02 (t, J=8.0, 1H); 6.92 (dd, J=1.0, 8.4, 1H); 4.00 (s, 3H); 3.87 (d, J=7.1, 2H); 3.12 (s, 3H); 1.28 (m, 1H); 0.60 (m, 2H); 0.30 (m, 2H).

Example 1.349 (CDCl$_3$): 10.71 (br s, 1H); 7.81 (dd, J=1.1, 7.9, 1H); 7.07 (t, J=8.3, 1H); 6.96 (dd, J=1.0, 8.4, 1H); 4.45 (q, J=7.1, 2H); 3.94 (d, J=7.1, 2H); 3.19 (s, 3H); 1.43 (t, J=7.1, 3H); 1.37 (m, 1H); 0.67 (m, 2H); 0.37 (m, 2H).

Example 1.350 (CDCl$_3$): 10.70 (br s, 1H); 7.80 (dd, J=1.2, 7.8, 1H); 7.06 (dd, J=7.9, 8.3, 1H); 6.96 (dd, J=1.1, 8.4, 1H); 4.33 (t, J=6.7, 2H); 3.93 (d, J=7.1, 2H); 3.18 (s, 3H); 1.80 (m, 2H); 1.36 (m, 1H); 0.98 (t, J=7.4, 3H); 0.67 (m, 2H); 0.36 (m, 2H).

Example 1.353 (CDCl$_3$): 10.71 (br s, 1H); 7.79 (dd, J=1.1, 7.9, 1H); 7.06 (t, J=8.3, 1H); 6.96 (dd, J=1.0, 8.4, 1H); 4.05 (s, 3H); 3.93 (d, J=7.9, 2H); 2.72 (m, 1H); 1.36 (m, 1H); 1.01 (m, 4H); 0.67 (m, 2H); 0.36 (m, 2H).

Example 1.356 (CDCl$_3$): 10.73 (br s, 1H); 7.79 (dd, J=0.6, 7.8, 1H); 7.06 (t, J=8.3, 1H); 6.95 (br d, J=8.3, 1H); 4.42 (q, J=7.0, 2H); 3.93 (d, J=7.1, 2H); 2.72 (m, 1H); 1.42 (t, J=7.1, 3H); 1.36 (m, 1H); 1.01 (m, 4H); 0.67 (m, 2H); 0.36 (m, 2H).

Example 1.359 (CDCl$_3$): 10.73 (br s, 1H); 7.80 (dd, J=1.1, 7.8, 1H); 7.06 (t, J=8.1, 1H); 6.96 (dd, J=1.0, 8.4, 1H); 4.32 (t, J=6.6, 2H); 3.94 (d, J=7.1, 2H); 2.73 (m, 1H); 1.81 (m, 2H); 1.37 (m, 1H); 1.01 (m, 4H); 1.00 (t, J=7.4, 3H); 0.68 (m, 2H); 0.37 (m, 2H).

Example 1.440 (d$_6$-DMSO): 8.25 (dd, J=0.8, 8.0, 1H); 7.62 (dt, J=0.8, 8.0, 1H); 7.44 (t, J=8.0, 1H); 3.98 (s, 3H); 3.04 (s, 3H).

Example 1.443 (d$_6$-DMSO): 8.26 (dd, J=0.8, 8.0, 1H); 7.63 (dt, J=0.8, 8.0, 1H); 7.47 (t, J=8.0, 1H); 4.37 (q, J=7.2, 2H); 3.04 (s, 3H); 1.36 (t, J=7.2, 3H).

Example 1.444 (d$_6$-DMSO): 8.27 (dd, J=0.8, 8.0, 1H); 7.64 (dt, J=0.8, 8.0, 1H); 7.46 (t, J=8.0, 1H); 4.28 (t, J=7.2, 2H); 3.06 (s, 3H); 1.76 (m, 2H); 0.96 (t, J=7.2, 3H).

Example 1.447 (d$_6$-DMSO): 8.25 (dd, J=1.2, 7.9, 1H); 7.62 (dt, J=1.3, 8.3, 1H); 7.46 (t, J=8.1, 1H); 3.96 (s, 3H); 2.75 (m, 1H); 0.90 (m, 4H).

Example 1.450 (CDCl$_3$): 11.00 (br s, 1H); 8.13 (dd, J=1.2, 8.0, 1H); 7.40 (m, 1H); 7.22 (t, J=8.1, 1H); 4.42 (q, J=7.1, 2H); 2.74 (m, 1H); 1.42 (t, J=7.1, 3H); 1.03 (m, 4H).

Example 1.453 (CDCl$_3$): 11.00 (br s, 1H); 8.12 (dd, J=1.2, 8.0, 1H); 7.40 (dt, J=1.4, 8.3, 1H); 7.22 (t, J=8.1, 1H); 4.32 (t, J=6.6, 2H); 2.74 (m, 1H); 1.81 (m, 2H); 1.03 (m, 4H); 1.00 (t, J=7.4, 3H).

Example 1.460 (CDCl$_3$): 11.02 (br s, 1H); 8.08 (dd, J=1.2, 7.8, 1H); 7.36 (br dd, J=1.0, 8.2, 1H); 7.21 (t, J=8.1, 1H); 6.78 (t, J=74.2, 1H); 4.08 (s, 3H); 3.21 (s, 3H).

Example 1.463 (CDCl$_3$): 11.05 (br s, 1H); 8.08 (dd, J=1.2, 8.0, 1H); 7.36 (dd, J=1.1, 8.2, 1H); 7.21 (t, J=8.1, 1H); 6.78 (t, J=74.2, 1H); 4.45 (q, J=7.1, 2H); 3.21 (s, 3H); 1.43 (t, J=7.1, 3H).

Example 1.464 (CDCl$_3$): 11.04 (br s, 1H); 8.07 (br d, J=7.9, 1H); 7.39 (br d, J=8.2, 1H); 7.20 (t, J=8.0, 1H); 6.78 (t, J=74.2, 1H); 4.34 (t, J=6.7, 2H); 3.21 (s, 3H); 1.81 (m, 2H); 0.91 (t, J=7.4, 3H).

Example 1.465 (CDCl$_3$): 11.09 (br s, 1H); 8.07 (dd, J=1.2, 8.0, 1H); 7.36 (dd, J=1.1, 8.2, 1H); 7.21 (t, J=8.0, 1H); 6.77 (t, J=74.3, 1H); 5.16 (m, 1H); 3.18 (s, 3H); 1.40 (d, J=6.2, 6H).

Example 1.467 (CDCl$_3$): 11.05 (br s, 1H); 8.07 (dd, J=1.2, 8.0, 1H); 7.36 (br dd, J=1.1, 8.2, 1H); 7.21 (t, J=8.1, 1H); 6.78 (t, J=74.2, 1H); 4.07 (s, 3H); 2.75 (m, 1H); 1.04 (m, 4H).

Example 1.470 (CDCl$_3$): 11.09 (br s, 1H); 8.07 (dd, J=1.2, 8.0, 1H); 7.36 (dd, J=1.1, 8.2, 1H); 7.21 (t, J=8.1, 1H); 6.79 (t, J=74.3, 1H); 4.44 (q, J=7.1, 2H); 2.75 (m, 1H); 1.43 (t, J=7.1, 3H); 1.04 (m, 4H).

Example 1.473 (CDCl$_3$): 11.09 (br s, 1H); 8.07 (dd, J=1.2, 8.0, 1H); 7.36 (br dd, J=1.1, 8.2, 1H); 7.20 (t, J=8.1, 1H); 6.79 (t, J=74.3, 1H); 4.33 (t, J=6.6, 2H); 2.75 (m, 1H); 1.82 (m, 2H); 1.04 (m, 4H); 1.00 (t, J=7.4, 3H).

Example 1.481 (CDCl$_3$): 10.76 (br s, 1H); 7.96 (dd, J=1.2, 7.8, 1H); 7.17 (t, J=8.3, 1H); 7.10 (dd, J=1.1, 8.3, 1H); 4.52 (q, J=8.2, 2H); 4.07 (s, 3H); 3.19 (s, 3H).

Example 1.488 (CDCl$_3$): 10.81 (br s, 1H); 7.95 (dd, J=1.4, 7.7, 1H); 7.16 (t, J=8.3; 1H); 7.09 (dd, J=1.3, 8.3, 1H); 4.52 (q, J=8.2, 2H); 4.05 (s, 3H); 2.73 (m, 1H); 1.02 (m, 4H).

Example 1.501 (CDCl$_3$): 10.76 (br s, 1H); 7.90 (dd, J=1.0, 7.9, 1H); 7.14 (t, J=8.2, 1H); 7.03 (dd, J=1.0, 8.4, 1H); 6.24 (tt, J=4.2, 54.9, 1H); 4.31 (td, J=4.2, 12.7, 2H); 4.06 (s, 3H); 3.19 (s, 3H).

Example 1.504 (CDCl$_3$): 10.78 (br s, 1H); 7.90 (d, J=7.9, 1H); 7.14 (t, J=8.0, 1H); 7.03 (d, J=8.3, 1H); 6.23 (tt, J=4.1, 54.9, 1H); 4.44 (q, J=7.1, 2H); 4.31 (td, J=4.0, 12.7, 2H); 3.19 (s, 3H); 1.42 (t, J=7.1, 3H).

Example 1.505 (CDCl$_3$): 10.78 (br s, 1H); 7.90 (dd, J=1.1, 7.9, 1H); 7.14 (t, J=8.2, 1H); 7.03 (dd, J=1.1, 8.4, 1H); 6.23 (tt, J=4.2, 55.0, 1H); 4.31 (m, 4H); 3.19 (s, 3H); 1.80 (m, 2H); 0.98 (t, J=7.4, 3H).

Example 1.506 (CDCl$_3$): 10.81 (br s, 1H); 7.90 (dd, J=1.1, 7.9, 1H); 7.14 (t, J=8.3, 1H); 7.03 (dd, J=1.1, 8.4, 1H); 6.24 (tt, J=4.2, 55.0, 1H); 5.15 (m, 1H); 4.31 (td, J=4.2, 12.7, 2H); 3.16 (s, 3H); 1.39 (d, J=6.2, 6H).

Example 1.508 (CDCl$_3$): 10.80 (br s, 1H); 7.90 (dd, J=1.1, 7.9, 1H); 7.13 (t, J=8.2, 1H); 7.02 (dd, J=1.0, 8.4, 1H); 6.24 (tt, J=4.2, 54.9, 1H); 4.31 (td, J=4.1, 12.7, 2H); 4.05 (s, 3H); 2.72 (m, 1H); 1.02 (m, 4H).

Example 1.511 (CDCl$_3$): 10.82 (br s, 1H); 7.89 (dd, J=1.0, 7.9, 1H); 7.13 (t, J=8.2, 1H); 7.02 (dd, J=0.8, 8.3, 1H); 6.24 (tt, J=4.2, 54.9, 1H); 4.42 (q, J=7.1, 2H); 4.31 (td, J=4.2, 12.7, 2H); 2.73 (m, 1H); 1.42 (t, J=7.1, 3H); 1.02 (m, 4H).

Example 1.514 (CDCl$_3$): 10.84 (br s, 1H); 7.90 (dd, J=1.1, 7.9, 1H); 7.13 (t, J=8.9, 1H); 7.02 (dd, J=1.1, 8.3, 1H); 6.24 (tt, J=4.2, 55.0, 1H); 4.31 (m, 4H); 2.73 (m, 1H); 1.81 (m, 2H); 1.02 (m, 4H).

Example 1.522 (CDCl$_3$): 10.70 (br s, 1H); 7.91 (dd, J=1.1, 7.8, 1H); 7.13 (t, J=8.4, 1H); 7.04 (br d, J=8.1, 1H); 4.83 (m, 1H); 4.06 (s, 3H); 3.19 (s, 3H); 1.59 (d, J=6.5, 3H).

Example 1.525 (CDCl$_3$): 10.73 (br s, 1H); 7.91 (dd, J=1.1, 7.8, 1H); 7.12 (t, J=8.3, 1H); 7.04 (br d, J=8.3, 1H); 4.83 (m, 1H); 4.44 (q, J=7.1, 2H); 3.18 (s, 3H); 1.59 (d, J=6.5, 3H); 1.42 (t, J=7.1, 3H).

Example 1.526 (CDCl$_3$): 10.72 (br s, 1H); 7.91 (dd, J=1.1, 7.8, 1H); 7.12 (t, J=8.4, 1H); 7.04 (d, J=8.1, 1H); 4.83 (m, 1H); 4.33 (m, 2H); 3.19 (s, 3H); 1.81 (m, 2H); 1.59 (d, J=6.5, 3H); 0.99 (t, J=7.4, 3H).

Example 1.527 (CDCl$_3$): 10.75 (br s, 1H); 7.91 (dd, J=1.1, 7.8, 1H); 7.12 (t, J=8.4, 1H); 7.04 (br d, J=8.0, 1H); 5.15 (m, 1H); 4.83 (m, 1H); 3.16 (s, 3H).

Example 1.529 (CDCl$_3$): 10.74 (br s, 1H); 7.91 (dd, J=1.1, 7.8, 1H); 7.12 (t, J=8.4, 1H); 7.04 (br d, J=8.1, 1H); 4.82 (m, 1H); 4.05 (s, 3H); 2.72 (m, 1H); 1.59 (d, J=6.5, 3H); 1.00 (m, 4H).

Example 1.532 (CDCl$_3$): 10.78 (br s, 1H); 7.91 (dd, J=1.1, 7.8, 1H); 7.12 (t, J=8.2, 1H); 7.04 (d, J=8.2, 1H); 4.82 (m, 1H); 4.42 (m, 2H); 2.72 (m, 1H); 1.59 (d, J=6.5, 3H); 1.42 (t, J=7.1, 3H); 1.01 (m, 4H).

Example 1.535 (CDCl$_3$): 10.77 (br s, 1H); 7.91 (dd, J=1.1, 7.8, 1H); 7.12 (t, J=8.4, 1H); 7.04 (br d, J=8.0, 1H); 4.82 (m, 1H); 4.31 (td, J=1.6, 6.6, 2H); 2.73 (m, 1H); 1.81 (m, 2H); 1.60 (d, J=6.5, 3H); 1.01 (m, 4H); 1.00 (t, J=7.4, 3H).

Example 1.544 (CDCl$_3$): 7.97 (dd, J=1.3, 7.7, 1H); 7.18 (t, J=8.3, 1H); 7.12 (dd, J=1.3, 8.3, 1H); 4.59 (td, J=0.9, 13.0, 2H); 4.07 (s, 3H); 3.19 (s, 3H).

Example 1.549 (CDCl$_3$): 7.97 (dd, J=1.4, 7.7, 1H); 7.17 (t, J=8.3, 1H); 7.12 (dd, J=1.3, 8.3, 1H); 4.59 (td, J=0.7, 12.9, 2H); 4.33 (t, J=6.7, 2H); 3.19 (s, 3H); 1.81 (m, 2H); 0.99 (t, J=7.4, 3H).

Example 1.550 (CDCl$_3$): 10.77 (br s, 1H); 7.97 (dd, J=1.5, 7.5, 1H); 7.18 (t, J=8.3, 1H); 7.12 (dd, J=1.5, 8.3, 1H); 5.16 (m, 1H); 4.59 (td, J=0.9, 13.0, 2H); 3.16 (s, 3H); 1.39 (d, J=6.2, 6H).

Example 1.552 (CDCl$_3$): 10.78 (br s, 1H); 7.97 (dd, J=1.3, 7.7, 1H); 7.17 (t, J=8.3, 1H); 7.11 (dd, J=1.2, 8.3, 1H); 4.59 (td, J=0.8, 12.9, 2H); 4.05 (s, 3H); 2.73 (m, 1H); 1.02 (m, 4H).

Example 1.555 (CDCl$_3$): 10.81 (br s, 1H); 7.97 (dd, J=1.1, 7.7, 1H); 7.17 (t, J=8.2, 1H); 7.11 (dd, J=1.2, 8.2, 1H); 4.59 (t, J=13.0, 2H); 4.42 (q, J=7.1, 2H); 2.73 (m, 1H); 1.43 (t, J=7.1, 3H); 1.02 (m, 4H).

Example 1.558 (CDCl$_3$): 7.97 (dd, J=1.3, 7.7, 1H); 7.17 (t, J=8.3, 1H); 7.11 (dd, J=1.3, 8.4, 1H); 4.59 (td, J=0.7, 13.0, 2H); 4.32 (t, J=6.6, 2H); 2.73 (m, 1H); 1.81 (m, 2H); 1.02 (m, 4H); 1.00 (t, J=7.4, 3H).

Example 1.579 (CDCl$_3$): 11.00 (br s, 1H); 7.93 (dd, J=1.1, 7.8, 1H); 7.32 (d, J=7.9, 1H); 7.04 (t, J=7.9, 1H); 4.06 (s, 3H); 3.20 (s, 3H); 2.45 (s, H).

Example 1.581 (CDCl$_3$): 11.02 (br s, 1H); 7.93 (dd, J=1.1, 7.8, 1H); 7.32 (d, J=8.1, 1H); 7.03 (t, J=7.9, 1H); 4.32 (t, J=6.7, 2H); 3.20 (s, 3H); 2.45 (s, 3H); 1.80 (m, 2H); 0.98 (t, J=7.4, 3H).

Example 1.582 (CDCl$_3$): 11.05 (br s, 1H); 7.93 (dd, J=1.1, 7.7, 1H); 7.32 (dd, J=0.7, 8.1, 1H); 7.03 (t, J=7.7, 1H); 5.14 (m, 1H); 3.17 (s, 3H); 2.45 (s, 3H); 1.39 (d, J=6.2, 6H).

Example 1.584 (CDCl$_3$): 11.04 (br s, 1H); 7.93 (dd, J=1.1, 7.7, 1H); 7.31 (dd, J=0.5, 8.2, 1H); 7.03 (t, J=8.0, 1H); 4.04 (s, 3H); 2.73 (m, 1H); 2.45 (s, 3H); 1.02 (m, 4H).

Example 1.585 (CDCl$_3$): 11.00 (br s, 1H); 7.93 (dd, J=1.1, 7.7, 1H); 7.31 (d, J=7.7, 1H); 7.03 (t, J=7.9, 1H); 4.41 (q, J=7.1, 2H); 2.73 (m, 1H); 2.45 (s, 3H); 1.42 (t, J=7.1, 3H); 1.02 (m, 4H).

Example 1.586 (CDCl$_3$): 11.06 (br s, 1H); 7.93 (dd, J=1.1, 7.8, 1H); 7.31 (d, J=8.2, 1H); 7.03 (t, J=7.9, 1H); 4.31 (t, J=6.6, 2H); 2.73 (m, 1H); 2.45 (s, 3H); 1.80 (m, 2H); 1.02 (m, 4H); 0.99 (t, J=7.4, 3H).

Example 1.711 (CDCl$_3$): 11.11 (br s, 1H); 8.10 (dd, J=1.2, 8.0, 1H); 7.63 (dd, J=1.2, 8.3, 1H); 7.23 (t, J=8.1, 1H); 4.07 (s, 3H); 3.44 (s, 3H); 3.21 (s, 3H).

Example 1.712 (CDCl$_3$): 11.17 (br s, 1H); 8.09 (dd, J=1.2, 8.0, 1H); 7.62 (dd, J=1.2, 8.3, 1H); 7.22 (t, J=8.11, 1H); 4.45 (q, J=7.1, 2H); 3.44 (s, 3H); 3.20 (s, 3H); 1.42 (t, J=7.1, 3H).

Example 1.713 (CDCl$_3$): 11.16 (br s, 1H); 8.10 (dd, J=1.2, 8.0, 1H); 7.62 (dd, J=1.1, 8.3, 1H); 7.23 (t, J=8.1, 1H); 4.34 (t, J=6.6, 2H); 3.44 (s, 3H); 3.21 (s, 3H); 1.59 (m, 2H); 0.99 (t, J=7.4, 3H).

Example 1.716 (CDCl$_3$): 11.14 (br s, 1H); 8.10 (dd, J=1.1, 8.0, 1H); 7.63 (dd, J=1.1, 8.3, 1H); 7.23 (t, J=8.2, 1H); 4.06 (s, 3H); 3.44 (s, 3H); 2.75 (m, 1H); 1.04 (m, 4H).

Example 1.717 (CDCl$_3$): 11.17 (br s, 1H); 8.09 (dd, J=1.2, 8.0, 1H); 7.62 (dd, J=1.2, 8.3, 1H); 7.22 (t, J=8.2, 1H); 4.43 (q, J=7.1, 2H); 3.44 (s, 3H); 2.74 (m, 1H); 1.43 (t, J=7.1, 3H); 1.03 (m, 4H).

Example 1.718 (CDCl$_3$): 11.18 (br s, 1H); 8.10 (dd, J=1.2, 8.0, 1H); 7.62 (dd, J=1.2, 8.3, 1H); 7.22 (t, J=8.1, 1H); 4.33 (t, J=6.6, 2H); 3.44 (s, 3H); 2.75 (m, 1H); 1.81 (m, 2H); 1.03 (m, 4H); 1.00 (t, J=7.4, 3H).

Example 1.749 (CDCl$_3$): 10.97 (br s, 1H); 8.04 (dd, J=1.2, 8.0, 1H); 7.75 (dd, J=1.2, 8.4, 1H); 7.19 (dd, J=8.0, 8.4, 1H); 4.07 (s, 3H); 3.20 (s, 3H); 3.13 (s, 6H).

Example 1.751 (CDCl$_3$): 10.99 (br s, 1H); 8.03 (dd, J=1.1, 8.0, 1H); 7.74 (dd, J=1.1, 8.4, 1H); 7.19 (t, J=8.0, 1H); 4.34 (t, J=6.7, 2H); 3.19 (s, 3H); 3.13 (s, 6H); 1.80 (m, 2H); 0.98 (t, J=7.4, 3H).

Example 1.752 (CDCl$_3$): 11.03 (br s, 1H); 8.04 (dd, J=1.1, 7.9, 1H); 7.75 (dd, J=1.1, 8.4, 1H); 7.19 (t, J=8.2, 1H); 5.16 (m, 2H); 3.17 (s, 3H); 3.13 (s, 6H); 1.39 (d, J=6.2, 6H).

Example 1.754 (CDCl$_3$): 10.99 (br s, 1H); 8.03 (dd, J=1.1, 7.9, 1H); 7.75 (dd, J=1.1, 8.4, 1H); 7.18 (t, J=8.2, 1H); 4.05 (s, 3H); 3.13 (s, 6H); 2.73 (m, 1H); 1.02 (m, 4H).

Example 1.755 (CDCl$_3$): 11.02 (br s, 1H); 8.03 (dd, J=1.2, 7.9, 1H); 7.74 (dd, J=1.1, 8.4, 1H); 7.18 (dd, J=8.0, 8.4, 1H); 4.43 (q, J=7.1, 2H); 3.13 (s, 6H); 2.73 (m, 1H); 1.42 (t, J=7.1, 3H); 1.02 (m, 4H).

Example 1.756 (CDCl$_3$): 11.02 (br s, 1H); 8.03 (dd, J=1.1, 7.9, 1H); 7.74 (dd, J=1.1, 8.4, 1H); 7.18 (t, J=8.0, 1H); 4.32 (t, J=6.6, 2H); 3.13 (s, 6H); 2.74 (m, 1H); 1.31 (m, 2H); 1.01 (m, 4H); 1.00 (t, J=7.4, 3H).

Example 1.815 (CDCl$_3$): 11.24 (br s, 1H); 7.99 (dd, J=0.8, 7.8, 1H); 7.29 (dd, J=0.6, 7.7, 1H); 7.03 (t, J=7.8, 1H); 2.87 (m, 1H); 2.87 (s, 3H); 1.91 (m, 1H); 1.12 (m, 8H).

Example 1.816 (d$_6$-DMSO): 7.89 (d, J=9.1, 1H); 7.37 (d, J=9.2, 1H); 3.99 (s, 3H); 3.87 (s, 3H); 3.07 (s, 3H).

Example 1.817 (d$_6$-DMSO): 7.89 (d, J=9.0, 1H); 7.37 (d, J=9.2, 1H); 4.37 (q, J=7.1, 2H); 3.87 (s, 3H); 3.06 (s, 3H); 1.36 (t, J=7.1, 3H).

Example 1.818 (d$_6$-DMSO): 7.89 (d, J=9.1, 1H); 7.37 (d, J=9.2, 1H); 4.28 (t, J=6.5, 2H); 3.87 (s, 3H); 3.07 (s, 2H); 1.75 (m, 2H); 0.95 (t, J=7.3, 3H).

Example 1.819 (d$_6$-DMSO): 7.89 (d, J=9.1, 1H); 7.37 (d, J=9.2, 1H); 5.02 (m, 1H); 3.88 (s, 3H); 3.04 (s, 3H); 1.36 (d, J=6.2, 6H).

Example 1.820 (CDCl$_3$): 10.87 (br s, 1H); 7.65 (d, J=9.0, 1H); 7.00 (d, J=9.0, 1H); 4.05 (s, 3H); 3.95 (s, 3H); 2.73 (m, 1H), 1.03 (m, 4H).

Example 1.821 (d$_6$-DMSO): 7.89 (d, J=9.1, 1H); 7.37 (d, J=9.1, 1H); 4.35 (q, J=7.1, 2H); 3.88 (s, 3H); 2.76 (m, 1H); 1.35 (t, J=7.1, 3H); 0.93 (m, 4H).

Example 1.822 (d$_6$-DMSO): 7.89 (d, J=9.0, 1H); 7.37 (d, J=9.2, 1H); 4.26 (t, J=6.4, 2H); 3.88 (s, 3H); 2.76 (m, 1H); 1.75 (m, 2H); 0.96 (t, J=7.3, 3H); 0.92 (m, 4H).

Example 1.823 (CDCl$_3$): 10.99 (br s, 1H); 8.42 (dd, J=5.6, 8.9, 1H); 7.76 (dd, J=2.5, 7.8, 1H); 7.24 (ddd, J=2.5, 7.5, 8.9, 1H); 4.07 (s, 3H); 3.21 (s, 3H).

Example 1.824 (CDCl$_3$): 11.02 (br s, 1H); 8.41 (dd, J=5.6, 8.9, 1H); 7.76 (dd, J=2.5, 7.8, 1H); 7.23 (ddd, J=2.5, 7.5, 8.9, 1H); 4.34 (t, J=6.7, 2H); 3.21 (s, 3H); 1.81 (m, 2H); 0.99 (t, J=7.4, 3H).

Example 1.825 (CDCl$_3$): 11.02 (br s, 1H); 8.41 (dd, J=5.6, 8.9, 1H); 7.76 (dd, J=2.5, 7.8, 1H); 7.23 (ddd, J=2.6, 7.6, 8.9, 1H); 4.06 (s, 3H); 2.74 (m, 1H); 1.04 (m, 4H).

Example 1.826 (CDCl$_3$): 11.05 (br s, 1H); 8.40 (dd, J=5.6, 8.9, 1H); 7.76 (dd, J=2.5, 7.8, 1H); 7.23 (ddd, J=2.6, 7.6, 8.9, 1H); 4.43 (q, J=7.1, 2H); 2.74 (m, 1H); 1.43 (t, J=7.1, 3H); 1.03 (m, 4H).

Example 1.827 (CDCl$_3$): 11.04 (br s, 1H); 8.40 (dd, J=5.6, 8.9, 1H); 7.76 (dd, J=2.5, 7.8, 1H); 7.22 (ddd, J=2.6, 7.6, 8.9, 1H); 4.33 (t, J=6.6, 2H); 2.75 (m, 1H); 1.81 (m, 2H); 1.03 (m, 4H); 1.00 (t, J=7.4, 3H).

Example 1.828 (CDCl$_3$): 11.10 (br s, 1H); 8.32 (dd, J=1.5, 7.9, 1H); 7.69 (dd, J=1.5, 8.0, 1H); 7.48 (t, J=8.0, 1H); 4.07 (s, 3H); 3.21 (s, 3H).

Example 1.829 (CDCl$_3$): 11.13 (br s, 1H); 8.31 (dd, J=1.5, 7.9, 1H); 7.69 (dd, J=1.5, 8.0, 1H); 7.48 (t, J=8.0, 1H); 4.44 (q, J=7.1, 2H); 3.20 (s, 3H); 1.42 (t, J=7.1, 3H).

Example 1.830 (CDCl$_3$): 11.13 (br s, 1H); 8.31 (dd, J=1.5, 8.0, 1H); 7.69 (dd, J=1.5, 8.0, 1H); 7.48 (t, J=8.0, 1H); 4.33 (t, J=6.6, 2H); 3.20 (s, 3H); 1.81 (m, 2H); 0.98 (t, J=7.4, 3H).

Example 1.831 (CDCl$_3$): 11.15 (br s, 1H); 8.31 (dd, J=1.6, 8.0, 1H); 7.69 (dd, J=1.6, 8.0, 1H); 7.48 (t, J=8.0, 1H); 5.15 (m, 1H); 3.17 (s, 3H); 1.39 (d, J=6.2, 6H).

Example 1.832 (CDCl$_3$): 11.14 (br s, 1H); 8.31 (dd, J=1.5, 7.9, 1H); 7.69 (dd, J=1.5, 8.0, 1H); 7.47 (t, J=8.0, 1H); 4.06 (s, 3H); 2.74 (m, 1H); 1.03 (m, 4H).

Example 1.833 (CDCl$_3$): 11.17 (br s, 1H); 8.30 (dd, J=1.5, 8.0, 1H); 7.68 (dd, J=1.6, 8.0, 1H); 7.47 (t, J=8.0, 1H); 4.42 (q, J=7.1, 2H); 2.73 (m, 1H); 1.42 (t, J=7.1, 3H); 1.03 (m, 4H).

Example 1.834 (CDCl$_3$): 11.16 (br s, 1H); 8.28 (dd, J=1.5, 8.0, 1H); 7.67 (dd, J=1.5, 8.0, 1H); 7.46 (t, J=8.0, 1H); 4.31 (t, J=6.5, 2H); 2.74 (m, 1H); 1.80 (m, 2H); 1.02 (m, 2H); 0.99 (t, J=7.4, 3H).

Example 1.835 (CDCl$_3$): 11.09 (br s, 1H); 8.63 (br s, 1H); 8.19 (d, J=8.2, 1H); 7.48 (ddd, J=0.6, 2.2, 8.2, 1H); 4.07 (s, 3H); 3.21 (s, 3H).

Example 1.836 (CDCl$_3$): 11.11 (br s, 1H); 8.63 (d, J=2.1, 1H); 8.19 (dd, J=0.5, 8.2, 1H); 7.48 (ddd, J=0.6, 2.2, 8.2, 1H); 4.45 (q, J=7.1, 2H); 3.21 (s, 3H); 1.42 (t, J=7.1, 3H).

Example 1.837 (CDCl$_3$): 11.11 (br s, 1H); 8.63 (d, J=2.0, 1H); 8.19 (d, J=8.3, 1H); 7.48 (dd, J=1.8, 7.8, 1H); 4.34 (t, J=6.7, 2H); 3.21 (s, 3H); 1.81 (m, 2H); 0.99 (t, J=7.4, 3H).

Example 1.838 (CDCl$_3$): 11.14 (br s, 1H); 8.63 (d, J=2.1, 1H); 8.20 (br d, J=8.0, H); 7.48 (ddd, J=0.6, 2.2, 8.2, 1H); 5.16 (m, 1H); 3.18 (s, 3H); 1.39 (d, J=6.2, 6H).

Example 1.839 (CDCl$_3$): 11.11 (br s, 1H); 8.62 (br d, J=1.8, 1H); 8.19 (dd, J=0.5, 8.2, 1H); 7.48 (ddd, J=0.6, 2.2, 8.1, 1H); 4.06 (s, 3H); 2.75 (m, 1H); 1.04 (m, 4H).

Example 1.840 (CDCl$_3$): 11.14 (br s, 1H); 8.62 (d, J=2.1, 1H); 8.19 (br d, J=8.2, 1H); 7.47 (ddd, J=0.5, 2.1, 8.2, 1H); 4.43 (q, J=7.1, 2H); 2.74 (m, 1H); 1.43 (t, J=7.1, 3H); 1.04 (m, 4H).

Example 1.841 (CDCl$_3$): 11.14 (br s, 1H); 8.62 (d, J=1.3, 1H); 8.19 (br d, J=8.2, 1H); 7.47 (ddd, J=0.6, 2.2, 8.2, 1H); 4.32 (t, J=6.6, 2H); 2.75 (m, 1H); 1.81 (m, 2H); 1.03 (m, 4H); 1.00 (t, J=7.4, 3H).

Example 1.842 (CDCl$_3$): 11.11 (br s, 1H); 8.36 (br s, 1H); 7.77 (br s, 1H); 4.08 (s, 3H); 3.21 (s, 3H).

Example 1.843 (CDCl$_3$): 11.15 (br s, 1H); 8.36 (br s, 1H); 7.77 (br s, 1H); 4.45 (q, J=7.1, 2H); 3.21 (s, 3H); 1.43 (t, J=7.1, 3H).

Example 1.844 (CDCl$_3$): 11.15 (br s, 1H); 8.36 (br s, 1H); 7.77 (br s, 1H); 4.34 (t, J=6.7, 2H); 3.21 (s, 3H); 1.81 (m, 2H); 0.99 (t, J=7.4, 3H).

Example 1.845 (CDCl$_3$): 8.36 (br s, 1H); 7.76 (br s, 1H); 5.16 (m, 1H); 3.18 (s, 3H); 1.39 (d, J=6.2, 6H).

Example 1.846 (CDCl$_3$): 11.13 (br s, 1H); 8.35 (br s, 1H); 7.76 (br s, 1H); 4.06 (s, 3H); 2.74 (m, 1H); 1.03 (m, 4H).

Example 1.847 (CDCl$_3$): 11.17 (br s, 1H); 8.35 (br s, 1H); 7.76 (br s, 1H); 4.43 (q, J=7.1, 2H); 2.74 (m, 1H); 1.42 (t, J=7.1, 3H); 1.04 (m, 4H).

Example 1.848 (CDCl$_3$): 11.19 (br s, 1H); 8.35 (br s, 1H); 7.76 (br s, 1H); 4.32 (t, J=6.6, 2H); 2.75 (m, 1H); 1.81 (m, 2H); 1.03 (m, 4H); 1.00 (t, J=7.4, 3H).

Example 1.849 (CDCl$_3$): 7.60 (d, J=8.6, 1H); 7.49 (d, J=8.6, 1H); 4.07 (s, 3H); 3.21 (s, 3H).

Example 1.850 (CDCl$_3$): 11.16 (br s, 1H); 7.60 (d, J=8.6, 1H); 7.49 (d, J=8.6, 1H); 4.45 (q, J=J=7.1, 2H); 3.20 (s, 3H); 1.42 (t, J=7.1, 3H).

Example 1.851 (CDCl$_3$): 11.16 (br s, 1H); 7.60 (d, J=8.6, 1H); 7.49 (d, J=8.7, 1H); 4.34 (t, J=6.7, 2H); 3.21 (s, 3H); 1.81 (m, 2H); 0.98 (t, J=7.4, 3H).

Example 1.852 (CDCl$_3$): 11.19 (br s, 1H); 7.60 (d, J=8.7, 1H); 7.49 (d, J=8.6, 1H); 5.15 (m, 1H); 3.18 (s, 3H); 1.39 (d, J=6.2, 1H).

Example 1.853 (CDCl$_3$): 11.16 (br s, 1H); 7.59 (d, J=8.6, 1H); 7.49 (d, J=8.6, 1H); 4.05 (s, 3H); 2.74 (m, 1H); 1.03 (m, 4H).

Example 1.854 (CDCl$_3$): 11.20 (br s, 1H); 7.59 (d, J=8.6, 1H); 7.49 (d, J=8.6, 1H); 4.43 (q, J=7.1, 2H); 2.74 (m, 1H); 1.42 (t, J=7.1, 3H); 1.03 (m, 4H).

Example 1.855 (CDCl$_3$): 10.99 (br s, 1H); 8.11 (dd, J=1.1, 8.1, 1H); 7.34 (m, 1H); 4.06 (s, 3H); 3.20 (s, 3H); 2.37 (d, J=1.9, 3H).

Example 1.856 (CDCl$_3$): 11.01 (br s, 1H); 8.10 (dd, J=1.1, 8.1, 1H); 7.33 (m, 1H); 4.43 (q, J=7.1, 2H); 3.19 (s, 3H); 2.37 (d, J=1.8, 3H); 1.42 (t, J=7.1, 3H).

Example 1.857 (CDCl$_3$): 11.02 (br s, 1H); 8.10 (dd, J=1.1, 8.1, 1H); 7.33 (ddd, J=0.7, 7.2, 7.9, 1H); 4.33 (t, J=6.7, 2H); 3.20 (s, 3H); 2.37 (d, J=2.3, 3H); 1.80 (sxt, J=7.4, 2H); 0.98 (t, J=7.4, 3H).

Example 1.858 (CDCl$_3$): 11.04 (br s, 1H); 8.10 (dd, J=1.0, 8.0, 1H); 7.33 (m, 1H); 5.14 (m, 1H); 3.17 (s, 3H); 2.37 (br d, J=2.4, 3H); 1.39 (d, J=6.2, 6H).

Example 1.859 (CDCl$_3$): 11.03 (br s, 1H); 8.10 (dd, J=1.0, 8.1, 1H); 7.33 (m, 1H); 4.05 (s, 3H); 2.73 (m, 1H); 2.37 (d, J=2.4, 3H); 1.03 (m, 4H).

Example 1.860 (CDCl$_3$): 11.05 (br s, 1H); 8.10 (dd, J=1.1, 8.1, 1H); 7.32 (ddd, J=0.8, 7.2, 8.0, 1H); 4.42 (q, J=7.1, 2H); 2.73 (m, 1H); 2.37 (d, J=2.3, 3H); 1.42 (t, J=7.1, 3H); 1.02 (m, 4H).

Example 1.861 (CDCl$_3$): 11.05 (br s, 1H); 8.10 (dd, J=1.1, 8.1, 1H); 7.33 (ddd, J=0.8, 7.2, 8.0, 1H); 4.31 (t, J=6.6, 2H); 2.74 (m, 1H); 2.37 (d, J=2.3, 3H); 1.81 (sxt, J=7.5, 2H); 1.03 (m, 4H).

Example 1.862 (CDCl$_3$): 10.89 (br s, 1H); 8.14 (s, 1H); 7.79 (s, 1H); 4.06 (s, 3H); 3.20 (s, 3H); 2.28 (s, 3H); 2.25 (s, 3H).

Example 1.863 (CDCl$_3$): 10.91 (br s, 1H); 8.13 (s, 1H); 7.78 (s, 1H); 4.43 (q, J=7.1, 2H); 3.18 (s, 3H); 2.27 (s, 3H); 2.24 (s, 3H); 1.41 (t, J=7.1, 3H).

Example 1.864 (CDCl$_3$): 10.90 (br s, 1H); 8.12 (s, 1H); 7.78 (s, 1H); 4.31 (t, J=6.6, 2H); 3.19 (s, 3H); 2.26 (s, 3H); 2.24 (s, 3H); 1.79 (sxt, J=7.4, 2H); 0.97 (t, J=7.4, 3H).

Example 1.865 (CDCl$_3$): 10.94 (br s, 1H); 8.14 (s, 1H); 7.79 (s, 1H); 5.14 (spt, J=6.2, 1H); 3.16 (s, 3H); 2.27 (s, 3H); 2.25 (s, 3H); 1.39 (d, J=6.2, 6H).

Example 1.866 (CDCl$_3$): 10.91 (br s, 1H); 8.13 (s, 1H); 7.78 (s, 1H); 4.04 (s, 3H); 2.72 (m, 1H); 2.26 (s, 3H); 2.24 (s, 3H); 1.01 (m, 4H).

Example 1.867 (CDCl$_3$): 10.94 (br s, 1H); 8.12 (s, 1H); 7.78 (s, 1H); 4.41 (q, J=7.1, 2H); 2.72 (m, 1H); 2.26 (s, 3H); 2.24 (s, 3H); 1.41 (t, J=7.1, 3H); 1.01 (m, 4H).

Example 1.868 (CDCl$_3$): 10.93 (br s, 1H); 8.12 (s, 1H); 7.78 (s, 1H); 4.30 (t, J=6.6, 2H); 2.73 (m, 1H); 2.26 (s, 3H); 2.24 (s, 3H); 1.80 (sxt, J=7.3, 2H); 1.01 (m, 4H); 0.99 (t, J=7.4, 3H).

Example 1.869 (CDCl$_3$): 10.99 (br s, 1H); 8.32 (d, J=8.6, 1H); 8.04 (d, J=2.1, 1H); 7.51 (dd, J=2.1, 8.6, 1H); 4.07 (s, 3H); 3.21 (s, 3H).

Example 1.870 (CDCl$_3$): 11.02 (br s, 1H); 8.31 (d, J=8.6, 1H); 8.04 (d, J=2.1, 1H); 7.51 (dd, J=2.0, 8.6, 1H); 4.45 (q, J=7.1, 2H); 3.20 (s, 3H); 1.43 (t, J=7.1, 3H).

Example 1.871 (CDCl$_3$): 11.03 (br s, 1H); 8.31 (d, J=8.6, 1H); 8.04 (d, J=2.0, 1H); 7.51 (dd, J=2.1, 8.6, 1H); 4.34 (t, J=6.7, 2H); 3.21 (s, 3H); 1.81 (sxt, J=7.5, 2H); 0.99 (t, J=7.4, 3H).

Example 1.872 (CDCl$_3$): 11.08 (br s, 1H); 8.31 (d, J=8.6, 1H); 8.04 (d, J=2.0, 1H); 7.51 (dd, J=2.1, 8.6, 1H); 5.16 (spt, J=6.2, 1H); 3.18 (s, 3H); 1.39 (d, J=6.2, 6H).

Example 1.873 (CDCl$_3$): 11.02 (br s, 1H); 8.29 (d, J=8.6, 1H); 8.02 (d, J=1.9, 1H); 7.50 (dd, J=2.0, 8.6, 1H); 4.05 (s, 3H); 2.73 (m, 1H); 1.02 (m, 4H).

Example 1.874 (CDCl$_3$): 11.06 (br s, 1H); 8.30 (d, J=8.6, 1H); 8.03 (d, J=2.1, 1H); 7.50 (dd, J=2.1, 8.6, 1H); 4.43 (q, J=7.1, 2H); 2.74 (m, 1H); 1.43 (t, J=7.1, 3H); 1.03 (m, 4H).

Example 1.875 (CDCl$_3$): 11.05 (br s, 1H); 8.30 (d, J=8.6, 1H); 8.03 (d, J=2.1, 1H); 7.50 (dd, J=2.1, 8.6, 1H); 4.32 (t, J=6.5, 2H); 2.74 (m, 1H); 1.81 (sxt, J=7.4, 2H); 1.03 (m, 4H); 1.00 (t, J=7.4, 3H).

Example 1.876 (CDCl$_3$): 10.93 (br s, 1H); 8.28 (d, J=8.2, 1H); 7.85 (d, J=1.2, 1H); 7.32 (br d, J=8.2, 1H); 4.06 (s, 3H); 3.20 (s, 3H); 2.58 (t, J=7.4, 2H); 1.49 (sxt, J=7.4, 2H); 0.95 (t, J=7.4, 3H).

Example 1.877 (CDCl$_3$): 10.94 (br s, 1H); 8.28 (d, J=8.2, 1H); 7.85 (d, J=1.7, 1H); 7.32 (dd, J=1.7, 8.1, 1H); 4.44 (q, J=7.1, 2H); 3.19 (s, 3H); 2.57 (t, J=7.4, 2H); 1.64 (sxt, J=7.3, 2H); 1.42 (t, J=7.1, 3H); 0.95 (t, J=7.3, 3H).

Example 1.878 (CDCl$_3$): 10.96 (br s, 1H); 8.27 (d, J=8.2, 1H); 7.85 (br s, 1H); 7.32 (br d, J=8.2, 1H); 4.33 (t, J=6.7, 2H); 3.19 (s, 3H); 2.57 (t, J=7.3, 2H); 1.80 (sxt, J=7.3, 2H); 1.63 (sxt, J=7.4, 2H); 0.98 (t, J=7.4, 3H); 0.94 (t, J=7.3, 3H).

Example 1.879 (CDCl$_3$): 10.98 (br s, 1H); 8.27 (d, J=8.2, 1H); 7.85 (d, J=1.7, 1H); 7.31 (1.7, 8.2, 1H); 5.14 (spt, J=6.2, 1H); 3.16 (s, 3H); 2.57 (t, J=7.5, 2H); 1.63 (sxt, J=7.4, 2H); 1.38 (d, J=6.2, 6H); 0.94 (t, J=7.3, 3H).

Example 1.880 (CDCl$_3$): 10.96 (br s, 1H); 8.28 (d, J=8.2, 1H); 7.85 (br s, 1H); 7.32 (br d, J=8.2, 1H); 4.05 (s, 3H); 2.73 (m, 1H); 2.57 (t, J=7.4, 2H); 1.64 (sxt, J=7.4, 2H); 1.02 (m, 4H); 0.95 (t, J=7.3, 3H).

Example 1.881 (CDCl$_3$): 10.99 (br s, 1H); 8.27 (d, J=8.2, 1H); 7.85 (d, J=1.7, 1H); 7.31 (dd, J=1.7, 8.2, 1H); 4.42 (q, J=7.1, 2H); 2.73 (m, 1H); 2.57 (t, J=7.4, 2H); 1.63 (sxt, J=7.4, 2H); 1.42 (t, J=7.1, 3H); 1.02 (m, 4H); 0.94 (t, J=7.3, 3H).

Example 1.882 (CDCl$_3$): 10.98 (br s, 1H); 8.27 (d, J=8.2, 1H); 7.85 (d, J=1.7, 1H); 7.31 (dd, J=1.7, 8.2, 1H); 4.31 (t, J=6.6, 2H); 2.74 (m, 1H); 2.57 (t, J=7.4, 2H); 1.80 (sxt, J=7.4, 2H); 1.63 (sxt, J=7.4, 2H); 1.02 (m, 4H); 0.99 (t, J=7.4, 3H); 0.94 (t, J=7.3, 3H).

Example 1.883 (CDCl$_3$): 10.96 (br s, 1H); 8.28 (d, J=8.2, 1H); 7.85 (d, J=1.6, 1H); 7.32 (dd, J=1.7, 8.2, 1H); 4.44 (q, J=7.1, 2H); 3.19 (s, 3H); 2.60 (t, J=7.6, 2H); 1.58 (m, 2H); 1.42 (t, J=7.1, 3H); 1.35 (sxt, J=7.5, 2H); 0.93 (t, J=7.3, 3H).

Example 1.884 (CDCl$_3$): 10.95 (br s, 1H); 8.27 (d, J=8.2, 1H); 7.85 (d, J=1.6, 1H); 7.32 (dd, J=1.7, 8.2, 1H); 4.33 (t, J=6.6, 2H); 3.20 (s, 3H); 2.59 (t, J=7.7, 2H); 1.80 (sxt, J=7.4, 2H); 1.58 (sxt, J=7.5, 2H); 1.35 (sxt, J=7.4, 2H); 0.98 (t, J=7.4, 3H); 0.93 (t, J=7.3, 3H).

Example 1.885 (CDCl$_3$): 10.92 (br s, 1H); 8.26 (d, J=8.2, 1H); 7.85 (d, J=1.6, 1H); 7.31 (dd, J=1.7, 8.2, 1H); 4.05 (s, 3H); 3.19 (s, 3H); 2.59 (t, J=7.7, 2H); 1.58 (m, 2H); 1.34 (sxt, J=7.4, 2H); 0.92 (t, J=7.3, 3H).

Example 1.886 (CDCl$_3$): 10.95 (br s, 1H); 8.26 (d, J=8.2, 1H); 7.84 (d, J=1.7, 1H); 7.31 (dd, J=1.7, 8.2, 1H); 4.04 (s, 3H); 2.73 (m, 1H); 2.59 (t, J=7.7, 2H); 1.57 (m, 2H); 1.34 (sxt, J=7.4, 2H); 1.01 (m, 4H); 0.92 (t, J=7.3, 3H).

Example 1.887 (CDCl$_3$): 10.98 (br s, 1H); 8.26 (d, J=8.2, 1H); 7.85 (d, J=1.6, 1H); 7.31 (dd, J=1.7, 8.2, 1H); 4.42 (q, J=7.1, 2H); 2.73 (m, 2H); 2.59 (t, J=7.7, 2H); 1.58 (m, 2H); 1.41 (t, J=7.1, 3H); 1.34 (sxt, J=7.4, 2H); 1.02 (m, 4H); 0.92 (t, J=7.3, 3H).

Example 1.888 (CDCl$_3$): 10.99 (br s, 1H); 8.27 (d, J=8.2, 1H); 7.85 (d, J=1H); 7.31 (dd, J=1.7, 8.2, 1H); 4.31 (t, J=6.6, 2H); 2.74 (m, 2H); 2.59 (t, J=7.7, 2H); 1.81 (sxt, J=7.5, 2H); 1.58 (m, 2H); 1.35 (sxt, J=7.4, 2H); 1.03 (m, 4H); 1.00 (t, J=7.4, 3H); 0.93 (t, J=7.3, 3H).

Example 1.889 (CDCl$_3$): 10.97 (br s, 1H); 8.26 (d, J=8.2, 1H); 7.85 (d, J=1.6, 1H); 7.31 (dd, J=1.6, 8.2, 1H); 5.13 (spt, J=6.1, 1H); 3.16 (s, 3H); 2.59 (t, J=7.6, 2H); 1.57 (m, 2H); 1.38 (d, J=6.2, 6H); 1.34 (m, 2H); 0.92 (t, J=7.3, 3H).

Example 1.890 (CDCl$_3$): 11.11 (br s, 1H); 8.51 (dd, J=0.5, 8.3, 1H); 8.26 (d, J=0.8, 1H); 7.80 (ddd, J=0.6, 1.7, 8.3, 1H); 4.45 (q, J=7.1, 2H); 3.21 (s, 3H); 1.42 (t, J=7.1, 3H).

Example 1.891 (CDCl$_3$): 11.14 (br s, 1H); 8.51 (d, J=8.3, 1H); 8.26 (d, J=1.0, 1H); 7.79 (dd, J=1.2, 8.3, 1H); 4.43 (q, J=7.1, 2H); 2.75 (m, 1H); 1.43 (t, J=7.1, 3H); 1.04 (m, 4H).

Example 1.892 (CDCl$_3$): 11.34 (br s, 1H); 8.50 (dd, J=0.6, 8.3, 1H); 8.25 (d, J=1.2, 1H); 7.79 (ddd, J=0.6, 1.8, 8.4, 1H); 2.88 (m, 1H); 1.91 (m, 1H); 1.13 (m, 8H).

Example 1.893 (CDCl$_3$): 11.10 (br s, 1H); 8.51 (d, J=8.3, 1H); 8.26 (br s, 1H); 7.80 (br d, J=8.3, 1H); 4.07 (s, 3H); 3.21 (s, 3H).

Example 1.894 (CDCl$_3$): 11.14 (br s, 1H); 8.50 (d, J=8.3, 1H); 8.26 (br s, 1H); 7.79 (br d, J=8.3, 1H); 4.33 (t, J=6.7, 2H); 3.21 (s, 3H); 1.80 (sxt, J=6.9, 2H); 0.98 (t, J=7.4, 3H).

Example 1.895 (CDCl$_3$): 11.15 (br s, 1H); 8.50 (d, J=8.3, 1H); 8.26 (d, J=1.0, 1H); 7.79 (dd, J=1.2, 8.3, 1H); 5.15 (spt, J=6.2, H); 3.18 (s, 3H); 1.39 (d, J=6.2, 6H).

Example 1.896 (CDCl$_3$): 11.12 (br s, 1H); 8.49 (d, J=8.3, 1H); 8.25 (br s, 1H); 7.79 (br d, J=8.3, 1H); 4.05 (s, 3H); 2.74 (m, 1H); 1.03 (m, 4H).

Example 1.897 (CDCl$_3$): 11.15 (br s, 1H); 8.49 (d, J=8.3, 1H); 8.25 (br s, 1H); 7.78 (br d, J=8.4, 1H); 4.31 (t, J=6.5, 2H); 2.75 (m, 1H); 1.81 (sxt, J=6.6, 2H); 1.01 (m, 4H); 0.99 (t, J=7.4, 3H).

TABLE 2

Compounds of the general formula (II*)

| | | | | Z* | | | |
|---|---|---|---|---|---|---|---|
| R | R1 | a | b | c | d | e | f |
| 2.001 a-f F | — | * | * | | | | |
| 2.002 a-f Br | — | | | | | | |
| 2.003 a-f I | — | | | | | | |
| 2.004 a-f CH$_3$ | — | * | * | | | | |
| 2.005 a-f CH$_3$ | 5-CH$_3$ | | | | | | |
| 2.006 a-f CH$_2$CH$_3$ | — | | | | | | |
| 2.007 a-f (CH$_2$)$_2$CH$_3$ | — | | | | | | |
| 2.008 a-f CH(CH$_3$)$_2$ | — | | | | | | |
| 2.009 a-f (CH$_2$)$_3$CH$_3$ | — | | | | | | |
| 2.010 a-f CH(CH$_3$)CH$_2$CH$_3$ | — | | | | | | |
| 2.011 a-f CH$_2$CH(CH$_3$)$_2$ | — | | | | | | |
| 2.012 a-f C(CH$_3$)$_3$ | — | | | | | | |
| 2.013 a-f CH=CH$_2$ | — | | | | | | |
| 2.014 a-f C(CH$_3$)CH$_2$ | — | | | | | | |
| 2.015 a-f C≡CH | — | | | | | | |
| 2.016 a-f C≡CCH$_3$ | — | | | | | | |
| 2.017 a-f C≡CCH$_2$CH$_3$ | — | | | | | | |
| 2.018 a-f CH$_2$CHCH$_2$ | — | | | | | | |
| 2.019 a-f CH$_2$C(CH$_3$)CH$_2$ | — | | | | | | |
| 2.020 a-f CH$_2$C≡CH | — | | | | | | |
| 2.021 a-f CH$_2$C≡CCH$_3$ | — | | | | | | |
| 2.022 a-f CH$_2$C≡CCH$_2$CH$_3$ | — | | | | | | |
| 2.023 a-f Cyclopropyl | — | | | | | | |
| 2.024 a-f 2,2-di-F-cyclopropyl | — | | | | | | |
| 2.025 a-f 2,2-di-Cl-cyclopropyl | — | | | | | | |
| 2.026 a-f 2,2-di-CH$_3$-cyclopropyl | — | | | | | | |
| 2.027 a-f Cyclobutyl | — | | | | | | |
| 2.028 a-f Cyclopentyl | — | | | | | | |
| 2.029 a-f Cyclohexyl | — | | | | | | |
| 2.030 a-f CH$_2$cyclopropyl | — | | | | | | |
| 2.031 a-f CH$_2$cyclobutyl | — | | | | | | |
| 2.032 a-f CH$_2$cyclopentyl | — | | | | | | |
| 2.033 a-f CH$_2$cyclohexyl | — | | | | | | |
| 2.034 a-f CH$_2$CCH$_3$ | — | | | | | | |
| 2.035 a-f CH$_2$CCH$_2$CH$_3$ | — | | | | | | |
| 2.036 a-f CH(CH$_3$)OCH$_3$ | — | | | | | | |
| 2.037 a-f Ph | — | | | | | | |
| 2.038 a-f 2-F-Ph | — | | | | | | |
| 2.039 a-f 3-F-Ph | — | | | | | | |
| 2.040 a-f 4-F-Ph | — | | | | | | |
| 2.041 a-f 2,6-di-F-Ph | — | | | | | | |
| 2.042 a-f 2,4-di-F-Ph | — | | | | | | |
| 2.043 a-f 2-Cl-Ph | — | | | | | | |
| 2.044 a-f 3-Cl-Ph | — | | | | | | |
| 2.045 a-f 4-Cl-Ph | — | | | | | | |
| 2.046 a-f 2,6-di-Cl-Ph | — | | | | | | |

TABLE 2-continued

Compounds of the general formula (II*)

(II*)

|  |  |  | Z* | | | | | |
|---|---|---|---|---|---|---|---|---|
| | R | R1 | a | b | c | d | e | f |
| 2.047 a-f | 2,4-di-Cl-Ph | — | | | | | | |
| 2.048 a-f | 2-MeO-Ph | — | | | | | | |
| 2.049 a-f | 3-MeO-Ph | — | | | | | | |
| 2.050 a-f | 4-MeO-Ph | — | | | | | | |
| 2.051 a-f | 2,4-di-MeO-Ph | — | | | | | | |
| 2.052 a-f | 2-Me-Ph | — | | | | | | |
| 2.053 a-f | 3-Me-Ph | — | | | | | | |
| 2.054 a-f | 4-Me-Ph | — | | | | | | |
| 2.055 a-f | 2-$CF_3$-Ph | — | | | | | | |
| 2.056 a-f | 3-$CF_3$-Ph | — | | | | | | |
| 2.057 a-f | 4-$CF_3$-Ph | — | | | | | | |
| 2.058 a-f | $CH_2$Ph | — | | | | | | |
| 2.059 a-f | $CH_2$-2-F-Ph | — | | | | | | |
| 2.060 a-f | $CH_2$-2,4-di-F-Ph | — | | | | | | |
| 2.061 a-f | $CH_2$-2-MeO-Ph | — | | | | | | |
| 2.062 a-f | $CH_2$-3-MeO-Ph | — | | | | | | |
| 2.063 a-f | $CF_3$ | — | | * | * | | | |
| 2.064 a-f | $CF_3$ | 5-$CH_3$ | | | | | | |
| 2.065 a-f | $CHF_2$ | — | | | | | | |
| 2.066 a-f | $CH_2F$ | — | | | | | | |
| 2.067 a-f | $CH_2CF_3$ | — | | | | | | |
| 2.068 a-f | $CH_2CHF_2$ | — | | | | | | |
| 2.069 a-f | $CH_2CH_2F$ | — | | | | | | |
| 2.070 a-f | CF=$CH_2$ | — | | | | | | |
| 2.071 a-f | CH=$CF_2$ | — | | | | | | |
| 2.072 a-f | $CF_2$CH=$CH_2$ | — | | | | | | |
| 2.073 a-f | CH=CH—$CF_3$ | — | | | | | | |
| 2.074 a-f | CHFCH=$CH_2$ | — | | | | | | |
| 2.075 a-f | CN | — | | | | | | |
| 2.076 a-f | $NO_2$ | — | | | | | | |
| 2.077 a-f | $NH_2$ | — | | | | | | |
| 2.078 a-f | $NHCH_3$ | — | | | | | | |
| 2.079 a-f | $N(CH_3)_2$ | — | | | | | | |
| 2.080 a-f | $N(CH_3)CH_2$CH=$CH_2$ | — | | | | | | |
| 2.081 a-f | $N(CH_3)CH_2$C≡CH | — | | | | | | |
| 2.082 a-f | NH-cyclopropyl | — | | | | | | |
| 2.083 a-f | $N(CH_3)$-cyclopropyl | — | | | | | | |
| 2.084 a-f | $N(CH_2CH_3)$-cyclopropyl | — | | | | | | |
| 2.085 a-f | NHC(O)H | — | | | | | | |
| 2.086 a-f | NHC(O)$CH_3$ | — | | | | | | |
| 2.087 a-f | NHC(O)O$CH_3$ | — | | | | | | |
| 2.088 a-f | $NHSO_2CH_3$ | — | | | | | | |
| 2.089 a-f | $NHSO_2CF_3$ | — | | | | | | |
| 2.090 a-f | $NHSO_2CHF_2$ | — | | | | | | |
| 2.091 a-f | $NHSO_2CH_2F$ | — | | | | | | |
| 2.092 a-f | $OCH_3$ | — | | * | * | | | |
| 2.093 a-f | $OCH_3$ | 5-$CH_3$ | | | | | | |
| 2.094 a-f | $OCH_2CH_3$ | — | | * | | | | |
| 2.095 a-f | $O(CH_2)_2CH_3$ | — | | * | | | | |
| 2.096 a-f | $OCH(CH_3)_2$ | — | | * | | | | |
| 2.097 a-f | $OCH(CH_3)_2$ | 5-$CH_3$ | | | | | | |
| 2.098 a-f | $O(CH_2)_3CH_3$ | — | | | | | | |
| 2.099 a-f | $OCH(CH_3)CH_2CH_3$ | — | | | | | | |
| 2.100 a-f | $OCH_2CH(CH_3)_2$ | — | | | | | | |
| 2.101 a-f | $OC(CH_3)_3$ | — | | | | | | |
| 2.102 a-f | OCH=$CH_2$ | — | | | | | | |
| 2.103 a-f | $OC(CH_3)$=$CH_2$ | — | | | | | | |
| 2.104 a-f | OCH=CH($CH_3$) | — | | | | | | |
| 2.105 a-f | OCH=C($CH_3$)$_2$ | — | | | | | | |
| 2.106 a-f | $OC(CH_3)$=CH$CH_3$ | — | | | | | | |
| 2.107 a-f | $OC(CH_3)$=C($CH_3$)$_2$ | — | | | | | | |
| 2.108 a-f | OC≡CH | — | | | | | | |
| 2.109 a-f | OC≡$CCH_3$ | — | | | | | | |

TABLE 2-continued

Compounds of the general formula (II*)

(II*)

|  | R | R1 | Z* a | b | c | d | e | f |
|---|---|---|---|---|---|---|---|---|
| 2.110 a-f | OC≡CCH$_2$CH$_3$ | — | | | | | | |
| 2.111 a-f | OCH$_2$CH=CH$_2$ | — | | | | | | |
| 2.112 a-f | OCH$_2$C(CH$_3$)=CH$_2$ | — | | | | | | |
| 2.113 a-f | OCH$_2$CH=CHCH$_3$ | — | | | | | | |
| 2.114 a-f | OCH$_2$CH=C(CH$_3$)$_2$ | — | | | | | | |
| 2.115 a-f | OCH$_2$C(CH$_3$)=CHCH$_3$ | — | | | | | | |
| 2.116 a-f | OCH$_2$C(CH$_3$)=C(CH$_3$)$_2$ | — | | | | | | |
| 2.117 a-f | OCH(CH$_3$)CH=CH$_2$ | — | | | | | | |
| 2.118 a-f | OCH$_2$C≡CH | — | | | | | | |
| 2.119 a-f | OCH$_2$C≡CCH$_3$ | — | | | | | | |
| 2.120 a-f | OCH$_2$C≡CCH$_2$CH$_3$ | — | | | | | | |
| 2.121 a-f | OCH(CH$_3$)C≡CH | — | | | | | | |
| 2.122 a-f | O-cyclopropyl | — | | | | | | |
| 2.123 a-f | O-2,2-di-Cl-cyclopropyl | — | | | | | | |
| 2.124 a-f | O-2,2-di-F-cyclopropyl | — | | | | | | |
| 2.125 a-f | O-cyclobutyl | — | | | | | | |
| 2.126 a-f | O-cyclopentyl | — | | | | | | |
| 2.127 a-f | O-cyclohexyl | — | | | | | | |
| 2.128 a-f | OCH$_2$-cyclopropyl | — | | * | | | | |
| 2.129 a-f | OCH$_2$-cyclopropyl | 5-CH$_3$ | | | | | | |
| 2.130 a-f | OCH(CH$_3$)-cyclopropyl | — | | | | | | |
| 2.131 a-f | OCH$_2$-2-Me-cyclopropyl | — | | | | | | |
| 2.132 a-f | OCH$_2$-2,2-di-Me-cyclopropyl | — | | | | | | |
| 2.133 a-f | OCH$_2$-2,2-di-Cl-cyclopropyl | — | | | | | | |
| 2.134 a-f | OCH$_2$-2,2-di-F-cyclopropyl | — | | | | | | |
| 2.135 a-f | OCH$_2$-cyclobutyl | — | | | | | | |
| 2.136 a-f | OCH$_2$-cyclopentyl | — | | | | | | |
| 2.137 a-f | OCH(CH$_3$)-cyclopentyl | — | | | | | | |
| 2.138 a-f | OCH$_2$-cyclohexyl | — | | | | | | |
| 2.139 a-f | OCH(CH$_3$)-cyclohexyl | — | | | | | | |
| 2.140 a-f | OCH$_2$CCH$_3$ | — | | | | | | |
| 2.141 a-f | O(CH$_2$)$_2$OCH$_3$ | — | | | | | | |
| 2.142 a-f | OCH$_2$CCH$_2$CH$_3$ | — | | | | | | |
| 2.143 a-f | O(CH$_2$)$_2$OCH$_2$CH$_3$ | — | | | | | | |
| 2.144 a-f | OCH(CH$_3$)OCH$_3$ | — | | | | | | |
| 2.145 a-f | OPh | — | | | | | | |
| 2.146 a-f | O-2-F-Ph | — | | | | | | |
| 2.147 a-f | O-3-F-Ph | — | | | | | | |
| 2.148 a-f | O-4-F-Ph | — | | | | | | |
| 2.149 a-f | O-2,6-di-F-Ph | — | | | | | | |
| 2.150 a-f | O-2,4-di-F-Ph | — | | | | | | |
| 2.151 a-f | O-2-Cl-Ph | — | | | | | | |
| 2.152 a-f | O-3-Cl-Ph | — | | | | | | |
| 2.153 a-f | O-4-Cl-Ph | — | | | | | | |
| 2.154 a-f | O-2,6-di-Cl-Ph | — | | | | | | |
| 2.155 a-f | O-2,4-di-Cl-Ph | — | | | | | | |
| 2.156 a-f | O-2-CF$_3$-Ph | — | | | | | | |
| 2.157 a-f | O-3-CF$_3$-Ph | — | | | | | | |
| 2.158 a-f | O-4-CF$_3$-Ph | — | | | | | | |
| 2.159 a-f | O-2-MeO-Ph | — | | | | | | |
| 2.160 a-f | O-3-MeO-Ph | — | | | | | | |
| 2.161 a-f | O-4-MeO-Ph | — | | | | | | |
| 2.162 a-f | O-2,4-di-MeO-Ph | — | | | | | | |
| 2.163 a-f | O-2-Me-Ph | — | | | | | | |
| 2.164 a-f | O-3-Me-Ph | — | | | | | | |
| 2.165 a-f | O-4-Me-Ph | — | | | | | | |
| 2.166 a-f | OCH$_2$Ph | — | | | | | | |
| 2.167 a-f | OCH(CH$_3$)Ph | — | | | | | | |
| 2.168 a-f | OCH$_2$-2-F-Ph | — | | | | | | |
| 2.169 a-f | OCH$_2$-3-F-Ph | — | | | | | | |
| 2.170 a-f | OCH$_2$-4-F-Ph | — | | | | | | |
| 2.171 a-f | OCH$_2$-2,4-di-F-Ph | — | | | | | | |
| 2.172 a-f | OCH$_2$-2-Cl-Ph | — | | | | | | |

TABLE 2-continued

Compounds of the general formula (II*)

(II*)

|  | R | R1 | Z* a | b | c | d | e | f |
|---|---|---|---|---|---|---|---|---|
| 2.173 a-f | OCH$_2$-3-Cl-Ph | — | | | | | | |
| 2.174 a-f | OCH$_2$-4-Cl-Ph | — | | | | | | |
| 2.175 a-f | OCH$_2$-2,4-di-Cl-Ph | — | | | | | | |
| 2.176 a-f | OCH$_2$-2-MeO-Ph | — | | | | | | |
| 2.177 a-f | OCH$_2$-3-MeO-Ph | — | | | | | | |
| 2.178 a-f | OCH$_2$-4-MeO-Ph | — | | | | | | |
| 2.179 a-f | OCH$_2$-2-CF$_3$-Ph | — | | | | | | |
| 2.180 a-f | OCH$_2$-3-CF$_3$-Ph | — | | | | | | |
| 2.181 a-f | OCH$_2$-4-CF$_3$-Ph | — | | | | | | |
| 2.182 a-f | OCF$_3$ | — | | * | * | | | |
| 2.183 a-f | OCF$_3$ | 5-CH$_3$ | | | | | | |
| 2.184 a-f | OCHF$_2$ | — | | * | | | | |
| 2.185 a-f | OCHF$_2$ | 5-CH$_3$ | | | | | | |
| 2.186 a-f | OCH$_2$CF$_3$ | — | | * | | | | |
| 2.187 a-f | OCH$_2$CHF$_2$ | — | | * | | | | |
| 2.188 a-f | OCH$_2$CH$_2$F | — | | | | | | |
| 2.189 a-f | OCH(CH$_3$)CF$_3$ | — | | * | | | | |
| 2.190 a-f | OCH(CH$_3$)CHF$_2$ | — | | | | | | |
| 2.191 a-f | OCH(CH$_3$)CH$_2$F | — | | | | | | |
| 2.192 a-f | OCH$_2$CF$_2$CF$_3$ | — | | * | | | | |
| 2.193 a-f | OCH$_2$CF$_2$CHF$_2$ | — | | | | | | |
| 2.194 a-f | OCH$_2$CF$_2$CH$_2$F | — | | | | | | |
| 2.195 a-f | OCH(CH$_3$)CF$_2$CF$_3$ | — | | | | | | |
| 2.196 a-f | OCH(CH$_3$)CF$_2$CHF$_2$ | — | | | | | | |
| 2.197 a-f | OCH(CH$_3$)CF$_2$CH$_2$F | — | | | | | | |
| 2.198 a-f | OCH$_2$CHFCF$_3$ | — | | | | | | |
| 2.199 a-f | O(CH$_2$)$_2$CF$_3$ | — | | | | | | |
| 2.200 a-f | O(CH$_2$)$_2$CHF$_2$ | — | | | | | | |
| 2.201 a-f | O(CH$_2$)$_3$CF$_3$ | — | | | | | | |
| 2.202 a-f | O(CH$_2$)$_3$CHF$_2$ | — | | | | | | |
| 2.203 a-f | OCF=CH$_2$ | — | | | | | | |
| 2.204 a-f | OCH=CF$_2$ | — | | | | | | |
| 2.205 a-f | OCF$_2$CH=CH$_2$ | — | | | | | | |
| 2.206 a-f | OCHFCH=CH$_2$ | — | | | | | | |
| 2.207 a-f | OCH=CHCF$_3$ | — | | | | | | |
| 2.208 a-f | SCH$_3$ | — | | * | * | | | |
| 2.209 a-f | SCH$_2$CH$_3$ | — | | | | | | |
| 2.210 a-f | S(CH$_2$)$_2$CH$_3$ | — | | | | | | |
| 2.211 a-f | SCH(CH$_3$)$_2$ | — | | | | | | |
| 2.212 a-f | SC(CH$_3$)$_3$ | — | | | | | | |
| 2.213 a-f | SCH$_2$Ph | — | | | | | | |
| 2.214 a-f | SPh | — | | | | | | |
| 2.215 a-f | SCF$_3$ | — | | | | | | |
| 2.216 a-f | SCHF$_2$ | — | | | | | | |
| 2.217 a-f | SCH$_2$F | — | | | | | | |
| 2.218 a-f | SCH=CH$_2$ | — | | | | | | |
| 2.219 a-f | SCH$_2$CH=CH$_2$ | — | | | | | | |
| 2.220 a-f | SC≡CH | — | | | | | | |
| 2.221 a-f | SCH$_2$C≡CH | — | | | | | | |
| 2.222 a-f | S-cyclopropyl | — | | | | | | |
| 2.223 a-f | SCH$_2$-cyclopropyl | — | | | | | | |
| 2.224 a-f | SF$_5$ | — | | | | | | |
| 2.225 a-f | S(O)CH$_3$ | — | | | | | | |
| 2.226 a-f | S(O)CH$_2$CH$_3$ | — | | | | | | |
| 2.227 a-f | S(O)(CH$_2$)$_2$CH$_3$ | — | | | | | | |
| 2.228 a-f | S(O)CH(CH$_3$)$_2$ | — | | | | | | |
| 2.229 a-f | S(O)C(CH$_3$)$_3$ | — | | | | | | |
| 2.230 a-f | S(O)CH$_2$Ph | — | | | | | | |
| 2.231 a-f | S(O)Ph | — | | | | | | |
| 2.232 a-f | S(O)CF$_3$ | — | | | | | | |
| 2.233 a-f | S(O)CHF$_2$ | — | | | | | | |
| 2.234 a-f | S(O)CH$_2$F | — | | | | | | |
| 2.235 a-f | S(O)CH=CH$_2$ | — | | | | | | |

TABLE 2-continued

Compounds of the general formula (II*)

(II*)

|  |  |  | Z* | | | | | |
|---|---|---|---|---|---|---|---|---|
| | R | R1 | a | b | c | d | e | f |
| 2.236 a-f | S(O)CH₂CH=CH₂ | — | | | | | | |
| 2.237 a-f | S(O)C≡CH | — | | | | | | |
| 2.238 a-f | S(O)CH₂C≡CH | — | | | | | | |
| 2.239 a-f | S(O)-cyclopropyl | — | | | | | | |
| 2.240 a-f | S(O)CH₂-cyclopropyl | — | | | | | | |
| 2.241 a-f | SO₂CH₃ | — | | | | | | |
| 2.242 a-f | SO₂CH₂CH₃ | — | | | | | | |
| 2.243 a-f | SO₂(CH₂)₂CH₃ | — | | | | | | |
| 2.244 a-f | SO₂CH(CH₃)₂ | — | | | | | | |
| 2.245 a-f | SO₂C(CH₃)₃ | — | | | | | | |
| 2.246 a-f | SO₂CH₂Ph | — | | | | | | |
| 2.247 a-f | SO₂Ph | — | | | | | | |
| 2.248 a-f | SO₂CF₃ | — | | | | | | |
| 2.249 a-f | SO₂CHF₂ | — | | | | | | |
| 2.250 a-f | SO₂CH₂F | — | | | | | | |
| 2.251 a-f | SO₂CH=CH₂ | — | | | | | | |
| 2.252 a-f | SO₂OH₂CH=CH₂ | — | | | | | | |
| 2.253 a-f | SO₂C≡CH | — | | | | | | |
| 2.254 a-f | SO₂CH₂C≡CH | — | | | | | | |
| 2.255 a-f | SO₂-cyclopropyl | — | | | | | | |
| 2.256 a-f | SO₂CH₂-cyclopropyl | — | | | | | | |
| 2.257 a-f | SO₂NHCH₃ | — | | | | | | |
| 2.258 a-f | SO₂N(CH₃)₂ | — | | | | | | |
| 2.259 a-f | OSO₂CH₃ | — | | * | | | | |
| 2.260 a-f | OSO₂CH₃ | 5-CH₃ | | | | | | |
| 2.261 a-f | OSO₂CH₂CH₃ | — | | | | | | |
| 2.262 a-f | OSO₂CH(CH₃)₂ | — | | | | | | |
| 2.263 a-f | OSO₂C(CH₃)₃ | — | | | | | | |
| 2.264 a-f | OSO₂CH₂Ph | — | | | | | | |
| 2.265 a-f | OSO₂CF₃ | — | | | | | | |
| 2.266 a-f | OSO₂CHF₂ | — | | | | | | |
| 2.267 a-f | OSO₂CH₂F | — | | | | | | |
| 2.268 a-f | OSO₂CH₂CF₃ | — | | | | | | |
| 2.269 a-f | OSO₂CH₂CHF₂ | — | | | | | | |
| 2.270 a-f | OSO₂(CH₂)₂F | — | | | | | | |
| 2.271 a-f | OSO₂CH=CH₂ | — | | | | | | |
| 2.272 a-f | OSO₂CH₂CH=CH₂ | — | | | | | | |
| 2.273 a-f | OSO₂C≡CH | — | | | | | | |
| 2.274 a-f | OSO₂CH₂C≡CH | — | | | | | | |
| 2.275 a-f | OSO₂-cyclopropyl | — | | | | | | |
| 2.276 a-f | OSO₂CH₂-cyclopropyl | — | | | | | | |
| 2.277 a-f | OSO₂CH₂CN | — | | | | | | |
| 2.278 a-f | OSO₂NHCH₃ | — | | | | | | |
| 2.279 a-f | OSO₂N(CH₃)₂ | — | | * | | | | |
| 2.280 a-f | OSO₂NHCH₂CH=CH₂ | — | | | | | | |
| 2.281 a-f | OSO₂NHCH₂C≡CH | — | | | | | | |
| 2.282 a-f | OSO₂NHCF₃ | — | | | | | | |
| 2.283 a-f | OSO₂NHCHF₂ | — | | | | | | |
| 2.284 a-f | OSO₂NHCH₂F | — | | | | | | |
| 2.285 a-f | OC(O)H | — | | | | | | |
| 2.286 a-f | OC(O)CH₃ | — | | | | | | |
| 2.287 a-f | OC(O)CH₂CH₃ | — | | | | | | |
| 2.288 a-f | OC(O)OCH₃ | — | | | | | | |
| 2.289 a-f | OC(O)OCH₂CH₃ | — | | | | | | |
| 2.290 a-f | OC(O)NH₂ | — | | | | | | |
| 2.291 a-f | OC(O)NHCH₃ | — | | | | | | |
| 2.292 a-f | OC(O)N(CH₃)₂ | — | | | | | | |
| 2.293 a-f | OC(O)N(CH₂CH₃)₂ | — | | | | | | |
| 2.294 a-f | Si(CH₃)₃ | — | | | | | | |
| 2.295 a-f | 2-thienyl | — | | | | | | |
| 2.296 a-f | 3-thienyl | — | | | | | | |
| 2.297 a-f | 2-pyridyl | — | | | | | | |
| 2.298 a-f | 3-pyridyl | — | | | | | | |

TABLE 2-continued

Compounds of the general formula (II*)

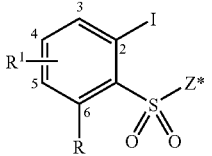

(II*)

| | R | R1 | a | b | c | d | e | f |
|---|---|---|---|---|---|---|---|---|
| 2.299 a-f | 4-pyridyl | — | * | | | | | |
| 2.300 a-f | OH | — | * | | | | | |
| 2.301 a-f | H | 3-Cl | * | * | | | | |
| 2.302 a-f | H | 3-Cl, 6-Cl | * | * | | | | |
| 2.303 a-f | H | 4-Cl, 6-Cl | * | * | | | | |
| 2.304 a-f | H | 5-CF$_3$ | * | * | | | | |
| 2.305 a-f | H | 4-CF$_3$, 6-Cl | * | * | | | | |
| 2.306 a-f | H | 3-F, 4-CH$_3$ | * | * | | | | |
| 2.307 a-f | H | 4-(CH$_2$)$_2$CH$_3$ | * | * | | | | |
| 2.308 a-f | H | 4-CH(CH$_3$)$_2$ | * | * | | | | |
| 2.309 a-f | H | 4-(CH$_2$)$_3$CH$_3$ | * | * | | | | |
| 2.310 a-f | H | 4-C(CH$_3$)$_3$ | * | * | | | | |
| 2.311 a-f | H | 4-CH$_2$CH$_3$ | * | * | | | | |

Compounds a: Z* = NH$_2$
Compounds b: Z* = NH-tert-butyl
Compounds c: z~ = NH-C(O)Ophenyl
Compounds d: Z* = NH-C(S)Ophenyl
Compounds e: Z* = NCO
Compounds f: Z* = NCS $^1$H NMR data for compounds of table 2:

Example: 2.001a (d$_6$-DMSO): 7.96 (dt, J=0.9, 7.8, 1H); 7.78 (br s, 2H); 7.43 (ddd, J=1.1, 8.3, 11.2, 1H); 7.28 (dt, J=5.4, 8.0, 1H).

Example: 2.004a (d$_6$-DMSO): 7.89 (br d, J=7.8, 1H); 7.55 (td, J=0.9, 7.6, 1H); 7.49 (br s, 2H); 7.40 (td, J=1.2, 7.9, 1H), 3.34 (s, 3H).

Example: 2.063a (d$_6$-DMSO): 8.48 (dd, J=1.0, 7.9, 1H); 7.95 (dd, J=1.0, 8.0, 1H); 7.74 (br s, 2H); 7.39 (br t, J=8.3, 1H).

Example: 2.092a (d$_6$-DMSO): 7.70 (dd, J=1.1, 7.7, 1H); 7.25 (dd, J=0.9, 8.4, 1H); 7.20 (br s, 2H); 7.17 (t, J=7.9, 1H); 3.90 (s, 3H).

Example: 2.094a (d$_6$-DMSO): 7.70 (dd, J=1.0, 7.8, 1H); 7.26 (br d, J=8.4, 1H); 7.15 (t, J=8.0, 1H); 7.03 (br s, 2H); 4.23 (q, J=7.0, 2H); 1.37 (t, J=6.9, 3H).

Example: 2.095a (d$_6$-DMSO): 7.70 (dd, J=1.0, 7.8, 1H); 7.26 (dd, J=0.9, 8.4, 1H); 7.15 (t, J=7.9, 1H); 6.98 (br s, 2H); 4.12 (t, J=6.6, 2H); 1.80 (m, 2H); 0.96 (t, J=7.4, 3H).

Example: 2.096a (d$_6$-DMSO): 7.69 (dd, J=1.0, 1H); 7.29 (br d, J=8.1, 1H); 7.14 (t, J=8.0, 1H); 6.91 (br s, 2H); 4.82 (m, 1H); 1.34 (d, J=6.0, 6H).

Example: 2.128a (d$_6$-DMSO): 7.71 (dd, J=1.1, 7.8, 1H); 7.27 (dd, J=1.1, 8.4, 1H); 7.15 (t, J=7.8, 1H); 7.01 (br s, 2H); 4.04 (d, J=7.2, 2H); 1.33 (m, 1H); 0.56 (m, 2H); 0.36 (m, 2H).

Example: 2.182a (d$_6$-DMSO): 8.19 (dd, J=1.1, 7.9, 1H); 7.67 (br s, 2H); 7.55 (dt, J=1.3, 8.3, 1H); 7.34 (t, J=8.1, 1H).

Example: 2.184a (CDCl$_3$): 7.96 (dd, J=1.2, 8.0, 1H); 7.25 (m, 1H); 7.07 (t, J=8.1, 1H); 6.51 (t, J=73.8, 1H); 6.37 (br s, 2H).

Example: 2.186a (d$_6$-DMSO): 7.84 (dd, J=0.9, 7.9, 1H); 7.40 (br d, J=8.2, 1H); 7.23 (t, J=8.0, 1H); 7.07 (br s, 2H); 4.99 (q, J=8.8, 2H).

Example: 2.187a (d$_6$-DMSO): 7.79 (dd, J=1.0, 7.8, 1H); 7.35 (dd, J=0.8, 8.4, 1H); 7.20 (t, J=7.9, 1H); 7.10 (br s, 2H); 6.53 (tt, J=3.7, 54.7, 1H); 4.51 (td, J=3.7, 14.3, 2H).

Example: 2.189a (d$_6$-DMSO): 7.83 (dd, J=0.8, 7.9, 1H); 7.46 (br d, J=8.3, 1H); 7.22 (t, J=8.1, 1H); 6.91 (br s, 2H); 5.50 (m, 1H); 1.48 (d, J=6.4, 3H).

Example: 2.192a (d$_6$-DMSO): 7.85 (dd, J=1.0, 7.9, 1H); 7.42 (br d, J=8.3, 1H); 7.24 (t, J=8.0, 1H); 7.00 (br s, 2H); 5.07 (t, J=13.9, 2H).

Example: 2.208a (d$_6$-DMSO): 7.95 (dd, J=0.9, 7.7, 1H); 7.46 (m, 3H); 7.12 (t, J=7.9, 1H); 2.41 (s, 3H).

Example: 2.259a (d$_6$-DMSO): 8.13 (dd, J=1.2, 7.9, 1H); 7.60 (br s, 2H); 7.53 (dd, J=1.2, 8.2, 1H); 7.31 (t, J=8.0, 1H); 3.53 (s, 3H).

Example: 2.279a (d$_6$-DMSO): 8.07 (dd, J=1.2, 7.9, 1H); 7.52 (dd, J=1.2, 8.2, 1H); 7.19 (t, J=8.1, 1H); 5.48 (br s, 2H); 3.10 (s, 6H).

Example 2.301a (CDCl$_3$): 7.97 (m, 1H); 7.52 (m, 1H); 7.35 (m, 1H); 6.91 (br s, 2H).

Example 2.302a (CDCl$_3$): 7.58 (d, J=8.6, 1H); 7.50 (d, J=8.6, 1H); 5.49 (br s, 2H).

Example 2.303a (CDCl$_3$): 8.15 (d, J=2.1, 1H); 7.57 (d, J=2.1, 1H); 5.36 (br s, 2H).

Example 2.304a (CDCl$_3$): 8.43 (br d, J=1.9, 1H); 8.22 (dd, J=0.5, 8.2, 1H); 7.47 (ddd, J=0.6, 2.2, 8.2, 1H); 5.21 (br s, 2H).

Example 2.305a (CDCl$_3$): 8.35 (dd, J=0.8, 1.8, 1H); 7.81 (dd, J=0.5, 1.8, 1H); 5.43 (br s, 2H).

Example 2.306a (CDCl$_3$): 7.89 (dd, J=1.0, 8.1, 1H); 7.30 (m, 1H); 5.15 (br s, 2H); 2.39 (dd, J=0.5, 2.3, 3H).

Example 2.307a (CDCl$_3$): 8.06 (d, J=8.1, 1H); 7.88 (br s, 1H); 7.28 (d, J=9.0, 1H); 5.17 (br s, 2H); 2.59 (t, J=7.4, 2H).

Example 2.308a (CDCl$_3$): 8.08 (d, J=8.2, 1H); 7.91 (d, J=1.7, 1H); 7.34 (dd, J=1.8, 8.2, 1H); 5.21 (br s, 2H); 2.92 (spt, J=7.1, 1H); 1.26 (d, J=6.9, 6H).

Example 2.309a (CDCl$_3$): 8.05 (d, J=8.0, 1H); 7.87 (br s, 1H); 7.27 (br d, J=7.3, 1H); 5.17 (br s, 2H); 2.60 (t, J=7.5, 2H); 1.59 (m, 2H); 1.34 (sxt, J=7.5, 2H); 0.92 (t, J=7.2, 3H).

Example 2.310a (d$_6$-DMSO): 8.02 (d, J=1.9, 1H); 7.92 (d, J=8.3, 1H); 7.59 (dd, J=2.0, 8.4, 1H); 7.41 (br s, 2H); 1.28 (s, 9H).

Example 2.311a (d$_6$-DMSO): 7.94 (m, 2H); 7.40 (m, 3H); 2.63 (q, J=7.6, 2H); 1.17 (t, J=7.5, 3H).

Example: 2.300a (CDCl$_3$): 9.91 (s, 1H); 7.60 (m, 1H); 7.05 (m, 2H); 5.49 (br s, 2H).

Example 2.001 b (d$_6$-DMSO): 7.99 (dt, J=0.7, 7.7, 1H); 7.79 (br s, 1H); 7.42 (ddd, J=1.1, 8.1, 11.0, 1H); 7.28 (td, J=5.1, 7.7, 1H); 1.13 (s, 9H).

Example 2.004b (d$_6$-DMSO): 7.92 (dd, J=1.1, 7.7, 1H); 7.55 (m, 2H); 7.39 (m, 1H); 3.31 (s, 3H); 1.14 (s, 9H).

Example 2.063b (d$_6$-DMSO): 8.49 (dd, J=1.1, 7.7, 1H); 7.97 (dd, J=1.1, 8.1, 1H); 7.78 (br s, 1H); 7.40 (td, J=0.7, 8.1, 1H); 1.07 (s, 9H).

Example 2.092b (CDCl$_3$): 7.80 (m, 1H); 7.06 (m, 2H); 5.28 (br s, 1H); 3.99 (s, 3H); 1.22 (s, 9H).

Example 2.182b (CDCl$_3$): 8.12 (dd, J=0.8, 8.0, 1H); 7.41 (dt, J=0.8, 8.0, 1H); 7.18 (t, J=8.0, 1H); 5.12 (br s, 1H); 1.27 (s, 9H).

Example 2.208b (CDCl$_3$): 7.96 (dd, J=1.0, 7.5, 1H); 7.35 (dd, J=0.7, 8.5, 1H); 7.00 (t, J=7.8, 1H); 5.74 (br s, 1H); 2.47 (s, 3H); 1.25 (s, 9H).

Example 2.301b (CDCl$_3$): 8.13 (dd, J=1.6, 7.9, 1H); 7.62 (dd, J=1.5, 8.0, 1H); 7.42 (t, J=7.9, 1H); 5.35 (br s, 1H); 1.23 (s, 9H).

Example 2.302b (CDCl$_3$): 7.55 (d, J=9.0, 1H); 7.49 (d, J=9.0, 1H); 5.55 (br s, 1H); 1.28 (s, 9H).

Example 2.303b (CDCl$_3$): 8.15 (d, J=2.2, 1H); 7.55 (d, J=2.2, 1H); 5.30 (br s, 2H); 1.27 (s, 9H).

Example 2.304b (CDCl$_3$): 8.45 (br d, J=2.2, 1H); 8.19 (br d, J=8.1, 1H); 7.42 (m, 1H); 5.21 (br s, 1H); 1.24 (s, 9H).

Example 2.305b (CDCl$_3$): 8.35 (dd, J=0.7, 1.8, 1H); 7.78 (dd, J=0.6, 1.9, 1H); 5.37 (s, 2H); 1.28 (s, 9H).

Example 2.306b (CDCl$_3$): 7.91 (dd, J=1.0, 8.0, 1H); 7.28 (ddd, J=0.7, 7.2, 8.0, 1H); 5.18 (br s, 1H); 2.38 (dd, J=0.6, 2.3, 3H); 1.22 (s, 9H).

Example 2.307b (CDCl$_3$): 8.09 (d, J=8.1, 1H); 7.85 (d, J=1.3, 1H); 7.27 (dd, J=1.2, 8.1, 1H); 5.14 (br s, 2H); 2.58 (t, J=7.4, 2H); 1.65 (sxt, J=7.5, 2H); 1.21 (s, 9H); 0.94 (t, J=7.3, 3H).

Example 2.308b (CDCl$_3$): 8.10 (d, J=8.2, 1H); 7.87 (d, J=1.6, 1H); 7.31 (dd, J=1.7, 8.2, 1H); 5.15 (br s, 1H); 2.90 (spt, J=6.9, 1H); 1.25 (d, J=6.9, 6H); 1.22 (s, 9H).

Example 2.309b (CDCl$_3$): 8.08 (d, J=8.1, 1H); 7.85 (d, J=1.7, 1H); 7.26 (dd, J=1.7, 8.1, 1H); 5.15 (br s, 1H); 2.60 (t, J=7.6, 2H); 1.60 (m, 2H); 1.34 (sxt, J=7.4, 2H); 1.21 (s, 9H); 0.93 (t, J=7.3, 3H).

Example 2.310b (CDCl$_3$): 8.10 (d, J=8.3, 1H); 8.00 (d, J=1.8, 1H); 7.46 (dd, J=1.9, 8.4, 1H); 5.15 (br s, 1H); 1.32 (s, 9H); 1.22 (s, 9H).

Example 2.311b (CDCl$_3$): 8.09 (d, J=8.1, 1H); 7.87 (br d, J=1.7, 1H); 7.29 (br dd, J=1.7, 8.1, 1H); 5.15 (br s, 1H); 2.65 (q, J=7.6, 2H); 1.25 (t, J=7.6, 3H); 1.22 (s, 9H).

B. Formulation Examples a) A dust is obtained by mixing 10 parts by weight of a compound of the formula (I) and/or salts thereof and 90 parts by weight of talc as inert substance and comminuting the mixture in a hammer mill.

b) A wettable powder which is readily dispersible in water is obtained by mixing 25 parts by weight of a compound of the formula (I) and/or salts thereof, 64 parts by weight of kaolin-containing quartz as inert substance, 10 parts by weight of potassium ligninsulfonate and 1 part by weight of sodium oleoylmethyltaurate as wetter and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as solvent and 10 parts by weight of oxethylated nonylphenol as emulsifier.

e) Water-dispersible granules are obtained by mixing
75 parts by weight of a compound of the formula (I) and/or salts thereof,
10 parts by weight of calcium ligninsulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spraying on Water as granulating liquid.

f) Water-dispersible granules are also obtained by homogenizing and precomminuting
25 parts by weight of a compound of the formula (I) and/or salts thereof,
5 parts by weight of sodium 2,2'-dinaphthylmethane-6,6'-disulfonate,
2 parts by weight of sodium oleoylmethyltaurate,
1 part by weight of polyvinyl alcohol,
17 parts by weight of calcium carbonate and
50 parts by weight of water
in a colloid mill, then grinding the mixture in a bead mill, and atomizing and drying the resulting suspension in a spraying tower, using a single-fluid nozzle.

C. Biological Examples

1. Pre-Emergence Effect on Weeds

Seeds or sections of rhizome from monocot and dicot broadleaf weed plants were laid out in sandy loam soil in cardboard pots, and covered with soil. The compounds of the invention, formulated as wettable powders or emulsifiable concentrates, were then applied, in the form of aqueous suspensions or emulsions, at various dosages, onto the surface of the covering earth, at an application rate of 600 to 800 l of water per hectare (converted).

Following the treatment, the pots were placed in a greenhouse and maintained under good growth conditions for the weeds. Visual scoring of the plant damage or emergence damage was made when the test plants had emerged, after a test time of 3 to 4 weeks, in comparison to untreated controls. As the results show, compounds of the invention feature good pre-emergence herbicidal activity against a broad spectrum of gramineous and broadleaf weeds. For example, compounds 1.001, 1.004, 1.005, 1.008, 1.011, 1.014, 1.021, 1.022, 1.023, 1.024, 1.027, 1.028, 1.037, 1.038, 1.039, 1.040, 1.042, 1.043, 1.044, 1.133, 1.136, 1.137, 1.138, 1.140, 1.143, 1.191, 1.194, 1.195, 1.196, 1.197, 1.198, 1.201, 1.204, 1.211, 1.214, 1.215, 1.218, 1.221, 1.231, 1.235, 1.236, 1.237, 1.238, 1.241, 1.244, 1.251, 1.254, 1.255, 1.256, 1.258, 1.261, 1.264, 1.273, 1.274, 1.275, 1.276, 1.278, 1.279, 1.280, 1.281, 1.286, 1.289, 1.290, 1.294, 1.295, 1.346, 1.349, 1.350, 1.353, 1.356, 1.359, 1.440, 1.443, 1.444, 1.447, 1.450, 1.453, 1.460, 1.463, 1.464, 1.465, 1.467, 1.470, 1.473, 1.481, 1.488, 1.501, 1.504, 1.505, 1.506, 1.508, 1.511, 1.514, 1.522, 1.525, 1.526, 1.527, 1.529, 1.532, 1.535, 1.544, 1.549, 1.550, 1.552, 1.555, 1.558, 1.579, 1.581, 1.582, 1.584, 1.585, 1.586, 1.711, 1.712, 1.713, 1.716, 1.717, 1.718, 1.749, 1.751, 1.752, 1.754, 1.755, 1.756, 1.815, 1.816, 1.817, 1.818, 1.819, 1.820, 1.821, 1.822, 1.823, 1.824, 1.825, 1.826, 1.827, 1.828, 1.829, 1.830, 1.831, 1.832, 1.833, 1.834, 1.835, 1.836, 1.837, 1.838, 1.839, 1.840, 1.841, 1.842, 1.843, 1.844, 1.845, 1.846, 1.847, 1.848, 1.849, 1.850, 1.851, 1.852, 1.853, 1.854, 1.855, 1.856, 1.857, 1.858, 1.859, 1.860, 1.861, 1.862, 1.863, 1.864, 1.865, 1.866, 1.867, 1.868, 1.869, 1.870, 1.871, 1.872, 1.873, 1.874, 1.875, 1.876, 1.877, 1.878, 1.879, 1.880, 1.881, 1.882, 1.883, 1.884, 1.885, 1.886, 1.887, 1.888, 1.889, 1.890, 1.891, 1.892, 1.893, 1.894, 1.895, 1.896, 1.997 and other compounds from table 1 have a very good herbicidal action against weed plants such as *Sinapis alba, Chrysanthemum segetum, Avena sativa, Stellaria media, Echinochloa crus-galli, Lolium multiflorum, Setaria viridis, Abutilon theophrasti, Amaranthus retroflexus* and *Panicum miliaceum* when applied pre-emergence at a rate of 0.3 kg or less of active substance per hectare.

2. Post-Emergence Effect on Weeds

Seeds or sections of rhizome from monocot and dicot broadleaf weeds were made out in sandy loam soil in plastic pots, covered with soil, and cultivated in a greenhouse under good growth conditions. Three weeks after sowing, the test plants were treated at the three-leaf stage. The compounds of the invention, formulated as sprayable powders or as emulsion concentrates, were sprayed in different dosages onto the green parts of the plants, at an application rate of 600 to 800 l of water per hectare (converted). After the test plants had stood in the greenhouse under optimum growth conditions for a period of about 3 to 4 weeks, the effect of the products was scored visually in comparison to untreated controls. Post-emergence as well, the compositions of the invention exhibit good herbicidal activity against a broad spectrum of economically important gramineous and broadleaf weeds. For example, compounds 1.001, 1.004, 1.005, 1.008, 1.011, 1.014, 1.021, 1.022, 1.023, 1.024, 1.027, 1.028, 1.037, 1.038, 1.039, 1.040, 1.042, 1.043, 1.044, 1.133, 1.136, 1.137, 1.138, 1.140, 1.143, 1.191, 1.194, 1.195, 1.196, 1.197, 1.198, 1.201, 1.204, 1.211, 1.214, 1.215, 1.218, 1.221, 1.231, 1.235, 1.236, 1.237, 1.238, 1.241, 1.244, 1.251, 1.254, 1.255, 1.256, 1.258, 1.261, 1.264, 1.273, 1.274, 1.275, 1.276, 1.278, 1.279, 1.280, 1.281, 1.286, 1.289, 1.290, 1.294, 1.295, 1.346, 1.349, 1.350, 1.353, 1.356, 1.359, 1.440, 1.443, 1.444, 1.447, 1.450, 1.453, 1.460, 1.463, 1.464, 1.465, 1.467, 1.470, 1.473, 1.481, 1.488, 1.501, 1.504, 1.505, 1.506, 1.508, 1.511, 1.514, 1.522, 1.525, 1.526, 1.527, 1.529, 1.532, 1.535, 1.544, 1.549, 1.550, 1.552, 1.555, 1.558, 1.579, 1.581, 1.582, 1.584, 1.585, 1.586, 1.711, 1.712, 1.713, 1.716, 1.717, 1.718, 1.749, 1.751, 1.752, 1.754, 1.755, 1.756, 1.815, 1.816, 1.817, 1.818, 1.819, 1.820, 1.821, 1.822, 1.823, 1.824, 1.825, 1.826, 1.827, 1.828, 1.829, 1.830, 1.831, 1.832, 1.833, 1.834, 1.835, 1.836, 1.837, 1.838, 1.839, 1.840, 1.841, 1.842, 1.843, 1.844, 1.845, 1.846, 1.847, 1.848, 1.849, 1.850, 1.851, 1.852, 1.853, 1.854, 1.855, 1.856, 1.857, 1.858, 1.859, 1.860, 1.861, 1.862, 1.863, 1.864, 1.865, 1.866, 1.867, 1.868, 1.869, 1.870, 1.871, 1.872, 1.873, 1.874, 1.875, 1.876, 1.877, 1.878, 1.879, 1.880, 1.881, 1.882, 1.883, 1.884, 1.885, 1.886, 1.887, 1.888, 1.889, 1.890, 1.891, 1.892, 1.893, 1.894, 1.895, 1.896, 1.997 and other compounds from table 1 exhibit very good herbicidal action against weed plants such as *Sinapis alba, Echinochloa crus-galli, Lolium multiflorum, Chrysanthemum segetum, Setaria viridis, Abutilon theophrasti, Amaranthus retroflexus, Panicum miliaceum* and *Avena sativa* when applied post-emergence at a rate of 0.3 kg or less of active substance per hectare.

3. Crop Plant Tolerance

In further greenhouse experiments, seeds of a very large number of crop plants and weeds were laid out in sandy loam soil and covered with soil. One lot of pots was treated immediately as described in section 1, while the remaining pots were placed in a greenhouse until the plants had developed two to three true leaves, and were then sprayed as described in section 2 with the compounds of the invention at different dosages. Four to five weeks after application and a period of standing in the greenhouse, visual scoring found that compounds of the invention left dicotyledonous crops such as soybean, cotton, oilseed rape, sugarbeet or potato undamaged both pre-emergence and post-emergence and even at high active substance dosages. Some of the substances, moreover, also protected gramineous crops such as barley, wheat, rye, millet, maize or rice. The compounds of the invention in some cases exhibit high selectivity and are therefore suitable for controlling unwanted plant growth in agricultural crops.

What is claimed is:

1. A compound of the formula (I) or salt thereof

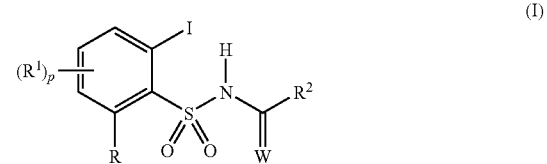

(I)

in which

R is a hydrocarbon radical or hydrocarbonoxy radical which is unsubstituted or substituted and inclusive of substituents has 1 to 30 carbon atoms, or R is a heterocyclyl radical or heterocyclyloxy radical which is unsubstituted or substituted, wherein when R is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, or R is a hydrogen atom, halogen or a radical $C(O)R^3$, $OC(O)R^3$, $S(O)_nR^3$, $OS(O)_nR^3$, OH, CN, $NO_2$, $NH_2$, $SF_5$, $NR^4R^5$ or $Si(R^6)_3$, where n is 0, 1 or 2, $R^1$ independently at each occurrence is halogen, OH, SH, a carbon-free, nitrogen-containing radical or a carbon-containing radical having 1 to 30 carbon atoms, p is 0, 1, 2 or 3, $R^2$ is an unsubstituted or substituted heterocyclyl radical having 5 ring members, wherein when $R^2$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, $R^3$ is a hydrocarbon radical or hydrocarbonoxy radical which is unsubstituted or substituted and inclusive of substituents has 1 to 30 carbon atoms, or $R^3$ is a heterocyclyl radical or heterocyclyloxy radical which is unsubstituted or substituted, or $R^3$ is a hydrogen atom, CN or $NR^4R^5$, wherein when $R^3$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, $R^4$ is a group of the formula $R^0$-$Q^0$-, in which $R^0$ is a hydrogen atom, an acyl radical, a hydrocarbon radical or a heterocyclyl radical, each of the last-mentioned two radicals being unsubstituted or substituted and inclusive of substituents having 1 to 30 carbon atoms, wherein when $R^0$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, and $Q^0$ is a direct bond or a divalent group of the formula —O— or —N($R^\#$)—, $R^\#$ being a hydrogen atom, an acyl radical or a hydrocarbon radical and the last-mentioned radical being unsubstituted or substituted and inclusive of substituents having 1 to 30 carbon atoms, or $R^0$ and $R^\#$ form with one another a nitrogen-containing heterocyclic ring, wherein when $R^\#$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, $R^5$ is a hydrogen atom, an acyl radical, a hydrocarbon radical or a heterocyclyl radical, each of the last-mentioned two radicals being unsubstituted or substituted and inclusive of substituents having 1 to 30 carbon atoms, wherein when $R^5$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, or $R^4$ and $R^5$ form with one another a nitrogen-containing heterocyclic ring, $R^6$ is a hydrocarbon radical which is unsubstituted or substituted and inclusive of substituents has 1 to 30 carbon atoms, wherein when $R^6$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, and W is an oxygen atom or a sulfur atom, wherein the salt thereof is a sodium-, potassium-, ammonium- or ethanolamine-salt.

2. A compound of the formula (I) or salt thereof as claimed in claim 1, in which R is $(C_1-C_6)$alkyl, $(C_2-C_6)$alkenyl, $(C_2-C_6)$alkynyl, $(C_3-C_6)$cycloalkyl, $(C_3-C_6)$-cycloalkenyl, $(C_3-C_6)$cycloalkynyl, $(C_1-C_6)$alkyloxy, $(C_2-C_6)$alkenyloxy, $(C_2-C_6)$-alkynyloxy, $(C_3-C_6)$cycloalkyloxy, phenyl, phenyloxy, H, F, Cl, Br, I, OH, CN, $NO_2$, $NH_2$, $SF_5$, $C(O)R^3$, $Si((C_1-C_6)alkyl)_3$, $N((C_1-C_6)alkyl)_2$, $NH(C_1-C_6)alkyl$, $N((C_2-C_6)alkenyl)_2$, $NH(C_2-C_6)alkenyl$, $N((C_2-C_6)alkynyl)_2$, $NH(C_2-C_6)alkynyl$, $NH((C_3-C_6)cycloalkyl)_2$, $NH(C_3-C_6)cycloalkyl$, $N(C_1-C_6)alkyl(C_3-C_6)cycloalkyl$, $S(O)_n(C_1-C_4)alkyl$, $S(O)_n(C_3-C_6)cycloalkyl$, $S(O)_n(C_1-C_6)alkenyl$, $S(O)_n(C_1-C_6)alkynyl$, $OSO_2(C_1-C_6)alkyl$, $OSO_2(C_3-C_6)cycloalkyl$, $OSO_2(C_1-C_6)alkenyl$, $OSO_2(C_1-C_6)alkynyl$, $OS(O)_n$phenyl, $OSO_2N((C_1-C_6)alkyl)_2$, $OSO_2NH(C_1-C_6)alkyl$, $OSO_2N((C_3-C_6)cycloalkyl)_2$, $OSO_2NH(C_3-C_6)cycloalkyl$, $OSO_2N((C_2-C_6)alkenyl)_2$, $OSO_2NH(C_2-C_6)alkenyl$, $OSO_2N((C_2-C_6)alkynyl)_2$, $OSO_2NH(C_2-C_6)alkynyl$, $OC(O)R^3$ or heterocyclyl, wherein said alkyl, alkenyl, alkynyl, cycloalkyl, cycloalkenyl, cycloalkynyl, alkyloxy, alkenyloxy, alkynyloxy, cycloalkoxy, phenyl, phenyloxy and heterocyclyl radicals are unsubstituted or substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, n is 0, 1 or 2, and $R^3$ is H, $(C_1-C_6)$alkyl, $(C_2-C_6)$alkenyl, $(C_2-C_6)$alkynyl, $(C_3-C_6)$-cycloalkyl, $(C_1-C_6)$alkyloxy, $(C_2-C_6)$alkenyloxy, $(C_2-C_6)$alkynyloxy, $(C_3-C_6)$-cycloalkyloxy, phenyl, heterocyclyl, CN, $NH(C_1-C_6)alkyl$ or $N((C_1-C_6)alkyl)_2$, wherein said alkyl, alkenyl, alkynyl, cycloalkyl, alkyloxy, alkenyloxy, alkynyloxy, cycloalkyloxy, phenyl and heterocyclyl radicals are unsubstituted or substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, $R^1$ is $(C_1-C_6)$alkyl, $(C_1-C_6)$haloalkyl, $(C_1-C_6)$alkyloxy, $(C_1-C_6)$haloalkoxy or halogen, p is 0, 1 or 2, $R^2$ is in each case selected from the group consisting of

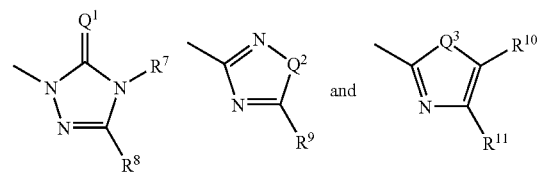

in which $Q^1$, $Q^2$ and $Q^3$ are each oxygen or sulfur, and $R^7$ is hydrogen, hydroxy, amino, cyano, is $(C_2-C_{10})$alkylideneamino, is $(C_1-C_6)$alkyl which is unsubstituted or substituted by fluorine, chlorine, bromine, cyano, $(C_1-C_4)$alkoxy, $(C_1-C_4)$alkylcarbonyl or $(C_1-C_4)$alkoxycarbonyl, is $(C_2-C_6)$alkynyl or $(C_2-C_6)$alkenyl each of which is unsubstituted or substituted by fluorine, chlorine or bromine, is $(C_1-C_6)$alkoxy, $(C_1-C_6)$alkylamino or $(C_1-C_6)$alkyl-carbonylamino each of which is unsubstituted or substituted by fluorine, chlorine, bromine, cyano, $(C_1-C_4)$alkoxy or $(C_1-C_4)$alkoxy-carbonyl, is $(C_3-C_6)$alkenyloxy, is di$((C_1-C_4)$alkyl(amino), is $(C_3-C_6)$cycloalkyl, $(C_3-C_6)$cycloalkylamino or $(C_3-C_6)$cyclo-alkyl-$(C_1-C_4)$alkyl each of which is unsubstituted or substituted by fluorine, chlorine, bromine, cyano or $(C_1-C_4)$alkyl, or is phenyl or phenyl-$(C_1-C_4)$alkyl each of which is unsubstituted or substituted by fluorine, chlorine, bromine, cyano, nitro, $(C_1-C_4)$alkyl, tri-fluoromethyl or $(C_1-C_4)$alkoxy, $R^8$ is hydrogen, hydroxy, mercapto, amino, cyano, fluorine, chlorine, bromine, iodine, is $(C_1-C_6)$alkyl unsubstituted or substituted by fluorine, chlorine, bromine, cyano, $(C_1-C_4)$alkoxy, $(C_1-C_4)$alkyl-carbonyl or $(C_1-C_4)$alkoxy-carbonyl, is $(C_2-C_6)$alkenyl or $(C_2-C_6)$alkynyl each of which is unsubstituted or substituted by fluorine, chlorine or bromine, is $(C_1-C_6)$alkoxy, $(C_1-C_6)$alkylthio, $(C_1-C_6)$alkylamino or $(C_1-C_6)$alkyl-carbonylamino each of which is unsubstituted or substituted by fluorine, chlorine, cyano $(C_1-C_4)$alkoxy or $(C_1-C_4)$alkoxy-carbonyl, is $(C_3-C_6)$alkenyloxy, $(C_3-C_6)$alkynyloxy, $(C_3-C_6)$alkenylthio, $(C_3-C_6)$alkynylthio, $(C_3-C_6)$alkenylamino or $(C_3-C_6)$alkynylamino, is di$((C_1-C_4)$alkyl)amino, is aziridino, pyrrolidino, piperidino or morpholino each of which is unsubstituted or substituted by methyl or ethyl, is $(C_{-3}-C_6)$cycloalkyl, $(C_5-C_6)$cycloalkenyl, $(C_3-C_6)$cycloalkyloxy, $(C_3-C_6)$cycloalkylthio, $(C_3-C_6)$cycloalkylamino, $(C_3-C_6)$cycloalkyl-$(C_1-C_4)$alkyl, $(C_3-C_6)$cyclo-alkyl-$(C_1-C_4)$alkoxy, $(C_3-C_6)$cycloalkyl-$(C_1-C_4)$alkylthio or $(C_3-C_6)$cyclo-alkyl-$(C_1-C_4)$alkylamino each of which is unsubstituted or substituted by fluorine, chlorine, bromine, cyano or $(C_1-C_4)$alkyl, or is phenyl, phenyl-$(C_1-C_4)$alkyl, phenoxy, phenyl-$(C_1-C_4)$alkoxy, phenylthio, phenyl-$(C_1-C_4)$alkylthio, phenylamino or phenyl-$(C_1-C_4)$alkylamino each of which is unsubstituted or substituted by fluorine, chlorine, bromine, cyano, nitro, $(C_1-C_4)$alkyl, trifluoromethyl, $(C_1-C_4)$alkoxy or $(C_1-C_4)$alkoxy-carbonyl, or $R^7$ and $R^8$ together are unbranched or branched alkanediyl having 3 to 11 carbon atoms, and additionally $R^9$, $R^{10}$ and $R^{11}$ are identical or different and are hydrogen, cyano, fluorine, chlorine, bromine, or are alkyl, alkenyl, alkynyl, alkoxy, alkenyloxy, alkynyloxy, alkylthio, alkenylthio, alkynylthio, alkylsulfynyl or alkylsulfonyl having in each case up to 6 carbon atoms and being in each case unsubstituted or substituted by fluorine, chlorine, bromine or $(C_1-C_4)$alkoxy, or are cycloalkyl having 3 to 6 carbon atoms and being unsubstituted or substituted by cyano, fluorine, chlorine, bromine or $(C_1-C_4)$alkyl, and W is an oxygen atom.

3. A compound of formula (I) or salt thereof as claimed in claim 1, in which R is $(C_1-C_4)$alkyl, $(C_2-C_4)$alkenyl, $(C_2-C_4)$alkynyl, $(C_3-C_6)$cycloalkyl, $(C_1-C_4)$-alkyloxy, $(C_2-C_4)$alkenyloxy, $(C_2-C_4)$alkynyloxy, $(C_3-C_6)$cycloalkyloxy, phenyl, phenyloxy, H, F, Cl, Br, I, C(O)$R^3$, CN, NO$_2$, NH$_2$, N((C$_1$-C$_4$)alkyl)$_2$, NH(C$_1$-C$_4$)alkyl, NH(C$_2$-C$_4$)alkenyl, NH(C$_2$-C$_4$)alkynyl, NH(C$_3$-C$_6$)cycloalkyl, N(C$_1$-C$_4$)alkyl (C$_3$-C$_6$)cycloalkyl, S(C$_1$-C$_4$)alkyl, S(C$_2$-C$_4$)alkenyl, S(C$_2$-C$_4$)alkynyl, S(C$_3$-C$_6$)cycloalkyl, S(O)(C$_1$-C$_4$)alkyl, S(O)(C$_1$-C$_4$)alkenyl, S(O)(C$_2$-C$_4$)alkynyl, S(O)(C$_3$-C$_6$)-cycloalkyl, SO$_2$(C$_1$-C$_4$)alkyl, SO$_2$(C$_2$-C$_4$)alkenyl, SO$_2$(C$_2$-C$_4$)alkynyl, SO$_2$(C$_3$-C$_6$)cycloalkyl, SO$_2$NH(C$_1$-C$_4$)alkyl, SO$_2$N((C$_1$-C$_4$)alkyl)$_2$, SO$_2$NH—(C$_3$-C$_6$)cycloalkyl, OSO$_2$(C$_1$-C$_4$)alkyl, OSO$_2$NH(C$_1$-C$_4$)alkyl, OSO$_2$N((C$_1$-C$_4$)alkyl)$_2$ or OC(O)$R^3$, $R^3$ being H, (C$_1$-C$_4$)alkyl, (C$_2$-C$_4$)alkenyl, (C$_2$-C$_4$)alkynyl, (C$_3$-C$_6$)cycloalkyl, (C$_1$-C$_4$)alkyloxy, (C$_2$-C$_4$)alkenyloxy, (C$_2$-C$_4$)alkynyloxy, (C$_3$-C$_6$)cycloalkyloxy, (C$_1$-C$_4$)haloalkyl, NH(C$_1$-C$_4$)alkyl or N((C$_1$-C$_4$)alkyl)$_2$, wherein said alkyl, alkenyl, alkynyl, cycloalkyl, alkyloxy, alkenyloxy, alkynyloxy, cycloalkyloxy, phenyl and phenyloxy radicals are unsubstituted or substituted by one or more radicals, preferably one, two or three radicals, from the group consisting of F, Cl, Br, I, (C$_1$-C$_4$)alkyl, (C$_1$-C$_4$)alkyloxy, (C$_1$-C$_4$)haloalkyl and (C$_1$-C$_4$)haloalkyloxy, $R^1$ is F, Cl, Br, I, (C$_1$-C$_4$)alkyl, (C$_1$-C$_4$)alkyloxy, (C$_1$-C$_4$)haloalkyl or (C$_1$-C$_4$)haloalkyloxy, p is 0 or 1, $R^2$ is in each case selected from the group consisting of

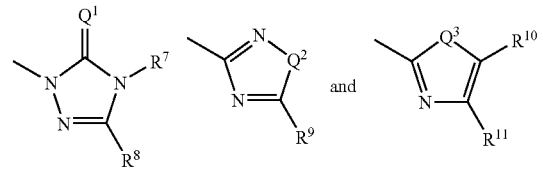

in which $Q^1$, $Q^2$ and $Q^3$ are each oxygen or sulfur and $R^7$ is hydrogen, hydroxy, amino, is $(C_3-C_8)$alkylideneamino, is methyl, ethyl, n-propyl or isopropyl, n-butyl, isobutyl, sec-butyl or tert-butyl in each case unsubstituted or substituted by fluorine, chlorine, cyano, methoxy or ethoxy, is propenyl, butenyl, propynyl or butynyl in each case unsubstituted or substituted by fluorine, chlorine or bromine, is methoxy, ethoxy, n-propoxy or isopropoxy, n-butoxy, isobutoxy, sec-butoxy or tert-butoxy, methylamino, ethylamino, n-propylamino or isopropylamino, n-butylamino, isobutylamino, sec-butylamino or tert-butylamino, in each case unsubstituted or substituted by fluorine, chlorine, cyano, methoxy or ethoxy, is propenyloxy or butenyloxy, is dimethylamino or diethylamino, is cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl in each case unsubstituted or substituted by fluorine, chlorine, methyl or ethyl, or is phenyl or benzyl in each case unsubstituted or substituted by fluorine, chlorine, methyl, trifluoromethyl or methoxy, $R^8$ is hydrogen, hydroxy, mercapto, amino, fluorine, chlorine, bromine, is methyl, ethyl, n-propyl or isopropyl, n-butyl, isobutyl, sec-butyl or tert-butyl in each case unsubstituted or substituted by fluorine, chlorine, cyano, methoxy or ethoxy, is ethenyl, propenyl, butenyl, propynyl or butynyl in each case unsubstituted or substituted by fluorine, chlorine or bromine, is methoxy, ethoxy, n-propoxy or isopropoxy, n-butoxy, isobutoxy, sec-butoxy or tert-butoxy, methylthio, ethylthio, n-propylthio or isopropythio, n-butylthio, isobutylthio, sec-butylthio or tert-butylthio, methylamino, ethylamino, n-propylamino or isopropylamino, n-butylamino, isobutylamino, sec-butylamino or tert-butylamino, in each case unsubstituted or substituted by chlorine, fluorine, cyano, methoxy or ethoxy, is propenyloxy, butenyloxy, propynyloxy, butynyloxy, propenylthio, propadienylthio, butenylthio, propynylthio, butynylthio, propenylamino, butenylamino, propynylamino or butynylamino, is dimethylamino, diethylamino or dipropylamino, is cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino , cyclobutylmethylamino, cyclopentylmethylamino or cyclohexylmethylamino in each case unsubstituted or substituted by fluorine, chlorine, methyl or ethyl, or is phenyl, benzyl, phenoxy, benzyloxy, phenylthio, benzylthio, phenylamino or benzylamino in each case unsubstituted or substituted by fluorine, chlorine, methyl, trifluoromethyl, methoxy or methoxycarbonyl, or $R^7$ and $R^8$ together are unbranched or branched alkanediyl having 3 to 11 carbon atoms, and additionally $R^9$, $R^{10}$ and $R^{11}$ are identical or different and are hydrogen, cyano, fluorine, chlorine, bromine, or are methyl, ethyl, n-propyl or isopropyl, n-butyl, isobutyl, sec-butyl or tert-butyl, propenyl, butenyl, propynyl, butynyl, methoxy, ethoxy, n-propoxy or isopropyl, n-butoxy, isobutoxy, sec-butoxy or tert-butoxy, propenyloxy, butenyloxy, propynyloxy, butynyloxy, methylthio, ethylthio, n-propylthio or isopropylthio, n-butylthio, isobutylthio, sec-butylthio or tert-butylthio, propenylthio, butenylthio, propynylthio, butynylthio, methylsulfinyl, ethylsulfinyl, methylsulfonyl or ethylsulfonyl, in each case unsubstituted or substituted by fluorine, chlorine, methoxy or ethoxy, or are cyclopropyl, and W is a hydrogen atom.

4. A compound of the formula (I) or salt thereof as claimed in claim 1, in which R is $CH_3$, $CH_2CH_3$, $(CH_2)_2CH_3$, $CH(CH_3)_2$, $C(CH_3)_3$, $CH=CH_2$, $C\equiv CH$, $CH_2CH=CH_2$, $CH_2C\equiv CH$, cyclopropyl, phenyl, H, F, Cl, Br, I, CN, $NO_2$, $NH_2$, $CH_2OCH_3$, $CF_3$, $CHF_2$, $C(O)H$, $C(O)CH_3$, $C(O)CH_2CH_3$, $C(O)OCH_3$, $C(O)OCH_2CH_3$, $NHCH_3$, $N(CH_3)_2$, NH-cyclopropyl, $N(CH_3)$-cyclopropyl, $NHC(O)H$, $NHC(O)CH_3$, $NHC(O)OCH_3$, $OCH_3$, $OCH_2CH_3$, $O(CH_2)_2CH_3$, $OCH(CH_3)_2$, $O(CH_2)_3CH_3$, $OCH_2CH(CH_3)_2$, $OCH(CH_3)CH_2CH_3$, $OC(CH_3)_3$, $OCH=CH_2$, $OC\equiv CH$, $OCH_2CH=CH_2$, $OCH_2C\equiv CH$, O-cyclopropyl, $OCH_2$-cyclopropyl, $O(CH_2)_2Cl$, $O(CH_2)_3Cl$, $OCH_2OCH_3$, Ophenyl, $OCH_2$phenyl, $OCF_3$, $OCHF_2$, $OCH_2F$, $OCH_2CF_3$, $OCH_2CHF_2$, $OCH(CH_3)CF_3$, $OCH_2CF_2CF_3$, $SCH_3$, $SCH_2CH_3$, $S(O)CH_3$, $S(O)CH_2CH_3$, $SO_2CH_3$, $SO_2CH_2CH_3$, $SO_2NHCH_3$, $SO_2N(CH_3)_2$, $SO_2NHCF_3$, $SO_2NHCHF_2$, $OSO_2CH_3$, $OSO_2CF_3$, $OSO_2CHF_2$, $OSO_2N(CH_3)_2$, $OSO_2NHCF_3$, $OSO_2NHCHF_2$, $OC(O)H$, $OC(O)CH_3$, $OC(O)OCH_3$, $OC(O)N(CH_3)_2$, p is 0, $R^2$ is of the following formula

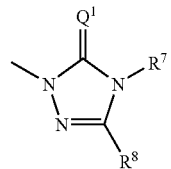

in which $Q^1$ is oxygen or sulfur, and $R^7$ is methyl, ethyl, n-propyl or isopropyl each of which is unsubstituted or substituted by fluorine, chlorine, cyano, methoxy or ethoxy, is propenyl or propynyl, is methoxy, ethoxy, n-propoxy or isopropoxy, or is cyclopropyl, $R^8$ is hydrogen, chlorine, bromine, is methyl, ethyl, n-propyl or isopropyl each of which is unsubstituted or substituted fluorine, chlorine, cyano, methoxy or ethoxy, is unsubstituted propenyl or propynyl, is propenyl or propynyl each of which is unsubstituted or substituted by fluorine or chlorine, is methoxy, ethoxy, n-propoxy or isopropoxy, methylthio, ethylthio, n-propylthio or isopropylthio, each of which is unsubstituted or substituted by fluorine, chlorine, cyano, methoxy or ethoxy, or is propenyloxy or cyclopropyl, and W is oxygen.

5. A process for preparing a compound of the formula (I) or salt thereof, as defined in claim 1, comprising (a) reacting an aminosulfonyl compound of the formula (II)

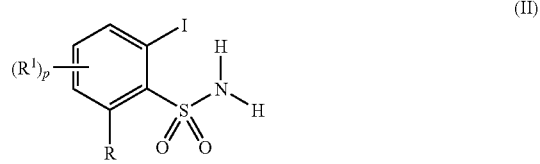

with a (thio)carboxylic acid derivative of the formula (III)

in which

R* is halogen or an unsubstituted or substituted ($C_1$-$C_{20}$) hydrocarbonoxy radical, optionally in the presence of a reaction auxiliary and optionally in the presence of a diluent, or (b) reacting a sulfonyliso(thio)cyanate of the formula (IV)

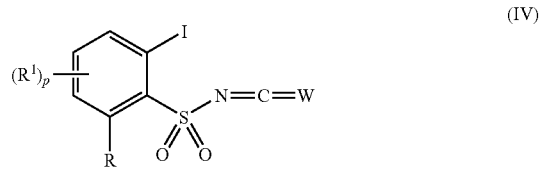

with a heterocyclyl compound of the formula (V)

H—R²      (V)

optionally in the presence of a reaction auxiliary and optionally in with or without the presence of a diluent,
or
(c) reacting a halosulfonyl compound of the formula (VI)

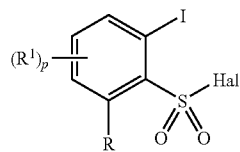
(VI)

with a heterocyclyl compound of the formula (V)

H—R²      (V)

and a metal (thio)cyanate of the formula (VII)

MWCN      (VII)

in which
M is a cation and
W is an oxygen atom or a sulfur atom,
optionally in the presence of a reaction auxiliary and optionally in the presence of a diluent,
or
(d) reacting a halosulfonyl compound of the formula (VI)

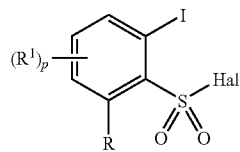
(VI)

with a (thio)carboxamide of the formula (VIII)

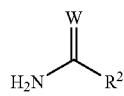
(VIII)

optionally in the presence of a reaction auxiliary and optionally in the presence of a diluent,
or
(e) reacting a sulfonylamino(thio)carbonyl compound of the formula (IX)

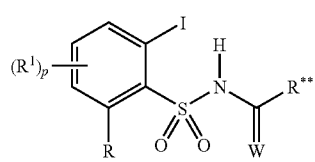
(IX)

in which
R** is halogen or an unsubstituted or substituted ($C_1$-$C_{20}$) hydrocarbon radical with a heterocyclyl compound of the formula (V)

H—R²      (V)

optionally in the presence of a reaction auxiliary and optionally in the presence of a diluent, and optionally converting the compound of the formula (I) obtained by process (a), (b), (c), (d) or (e) into a salt by customary methods, the radicals, groups, and indices R, $R^1$, $R^2$, W and 1 in the formulae (II)-(IX) being defined as in formula (I).

6. An agrochemical composition comprising a) at least one compound of the formula (I) or salt thereof, as defined in claim 1, and b) at least one crop protection auxiliary or additive selected from the group of stickers, wetters, dispersants, emulsifiers, penetrants, preservatives, frost preventives, solvents, fillers, carriers, colorants, defoamers, antievaporants, pH modifiers and viscosity modifiers.

7. A compound of formula (II*)

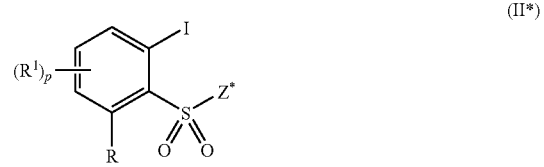
(II*)

in which
Z* is $NH_2$, NH-tert-butyl, NH—C(O)R, NH—C(S)R, NCO, NCS or halogen,
wherein
$R^1$ independently at each occurrence is halogen, OH, SH, a carbon-free, nitrogen-containing radical or a carbon-containing radical having 1 to 30 carbon atoms,
p is 0, 1, 2 or 3,
R** is halogen or an unsubstituted or substituted ($C_1$-$C_{20}$) hydrocarbon radical
R is a radical $C(O)R^3$; and
$R^3$ is a hydrocarbon radical or hydrocarbonoxy radical which is unsubstituted or substituted and inclusive of substituents has 1 to 30 carbon atoms, or $R^3$ is a heterocyclyl radical or heterocyclyloxy radical which is unsubstituted or substituted, or $R^3$ is a hydrogen atom, CN or $NR^4R^5$, wherein when $R^3$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy.

8. The compound of formula I:

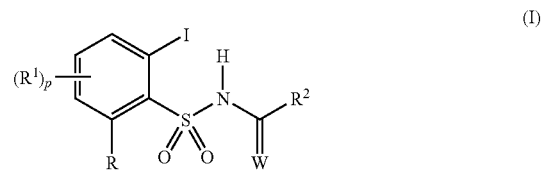
(I)

wherein R is selected from the group consisting of N($C_1$-$C_6$)alkyl $C(O)R^3$, $NHC(O)R^3$, N($C_1$-$C_6$)alkyl $S(O)_nR^3$, $NHS(O)_nR^3$, $S(O)_nNHR^3$, and $S(O)_nN(C_1$-$C_6)$alkyl $R^3$, $R^1$ independently at each occurrence is halogen, OH, SH, a carbon-free, nitrogen-containing radical or a carbon-containing radical having 1 to 30 carbon atoms, p is 0, 1, 2 or 3, $R^2$ is an unsubstituted or substituted heterocyclyl radical having 5 ring members, wherein when $R^2$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, $R^3$ is a hydrocarbon radical or hydrocarbonoxy radical which is unsubstituted or substituted and inclusive of substituents has 1 to 30 carbon atoms, or $R^3$ is a heterocyclyl radical or heterocyclyloxy radical which is unsubstituted or substituted, or $R^3$ is a hydrogen atom, CN or $NR^4R^5$, wherein when $R^3$ is substituted, it is substituted by halogen, alkoxy, haloalkoxy, alkylthio, hydroxyl, amino, nitro, carboxyl, cyano, azido, alkoxycarbonyl, alkylcarbonyl, formyl, carbamoyl, monoalkylaminocarbonyl, dialkylaminocarbonyl, acylamino, monoalkylamino, dialkylamino, alkylsulfinyl, haloalkylsulfinyl, alkylsulfonyl, haloalkylsulfonyl, cyclic alkyl, cyclic haloalkyl, alkenyl, alkynyl, alkenyloxy, or alkynyloxy, and W is an oxygen atom or a sulfur atom.

9. The compound of claim 8, wherein R is selected from the group consisting of $NHSO_2R^3$, $NHSO_2CH_3$, $NHSO_2CF_3$, and $NHSO_2CHF_2$.

10. A method of controlling weeds selected from the group consisting of *Apera spica venti*, *Avena* species, *Alopecurus* species, *Brachiaria* species, *Digitaria* species, *Lolium* species, *Echinochloa* species, *Panicum* species, *Phalaris* species, *Poa* species, *Setaria* species, *Bromus* species, annual *Cyperus* species, perennial *Cyperus* species, *Abutilon* species, *Amaranthus* species, *Chenopodium* species, *Chrysanthemum* species, *Galium* species, *Ipomoea* species, *Kochia* species, *Lamium* species, *Matricaria* species, *Pharbitis* species, *Polygonum* species, *Sida* species, *Sinapis* species, *Solanum* species, *Stellaria* species, *Veronica* species, *Viola* species, *Xanthium* species, *Convolvulus*, *Cirsium*, *Rumex*, *Artemisia*, *Echinochloa*, *Sagittaria*, *Alisma*, *Eleocharis*, *Scirpus* and *Cyperus*, comprising applying an effective amount of at least one compound of formula (I) or salt thereof, as defined in claim 1, to the weed, to the seed of the weed, or to an area on which the weed is growing.

* * * * *